US012636258B2

(12) United States Patent
Fujiwara et al.

(10) Patent No.: US 12,636,258 B2
(45) Date of Patent: May 26, 2026

(54) DRUG DELIVERY COMPOSITION

(71) Applicant: JAPAN SCIENCE AND TECHNOLOGY AGENCY, Saitama (JP)

(72) Inventors: Takayuki Fujiwara, Mishima (JP); Shunsuke Hirooka, Yokohama (JP); Shin-ya Miyagishima, Mishima (JP); Tsutomu Omatsu, Kawasaki (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 907 days.

(21) Appl. No.: 17/598,515

(22) PCT Filed: Mar. 27, 2020

(86) PCT No.: PCT/JP2020/014131
§ 371 (c)(1),
(2) Date: Sep. 27, 2021

(87) PCT Pub. No.: WO2020/203816
PCT Pub. Date: Oct. 8, 2020

(65) Prior Publication Data
US 2022/0249386 A1 Aug. 11, 2022

(30) Foreign Application Priority Data
Mar. 29, 2019 (JP) ................................. 2019-069029

(51) Int. Cl.
| | |
|---|---|
| *A61K 9/50* | (2006.01) |
| *A23K 10/30* | (2016.01) |
| *A23K 20/147* | (2016.01) |
| *A23K 40/30* | (2016.01) |
| *A23L 33/18* | (2016.01) |
| *A61K 9/00* | (2006.01) |
| *A61K 39/00* | (2006.01) |
| *C12N 1/12* | (2026.01) |

(52) U.S. Cl.
CPC ............ *A61K 9/5068* (2013.01); *A23K 10/30* (2016.05); *A23K 20/147* (2016.05); *A23K 40/30* (2016.05); *A23L 33/18* (2016.08); *A61K 9/0053* (2013.01); *C12N 1/12* (2013.01); *A23V 2002/00* (2013.01); *A61K 39/00* (2013.01); *A61K 2039/51* (2013.01); *A61K 2039/542* (2013.01); *A61K 2039/552* (2013.01)

(58) Field of Classification Search
CPC .... A61K 9/5068; A61K 9/0053; A61K 39/00; A61K 2039/51; A61K 2039/542; A61K 2039/552; A23K 20/147; A23K 40/30; A23K 10/30; A23L 33/18; C12N 1/12; A23V 2002/00
See application file for complete search history.

(56) References Cited

U.S. PATENT DOCUMENTS

| | | | |
|---|---|---|---|
| 2003/0022359 A1* | 1/2003 | Sayre ........................ | C12N 1/12 435/257.2 |
| 2003/0222359 A1* | 12/2003 | Jager ............... | B01F 23/231242 261/122.1 |
| 2011/0293659 A1 | 12/2011 | Breuing et al. | |

FOREIGN PATENT DOCUMENTS

| | | | |
|---|---|---|---|
| EP | 1790332 A1 | 5/2007 | |
| FR | 3064635 A1 * | 10/2018 | ............... A23L 5/46 |
| JP | 2012-508697 A | 4/2012 | |
| JP | 2015192598 A | 11/2015 | |
| JP | 2017506212 A | 3/2017 | |
| JP | 2017123816 A | 7/2017 | |
| WO | 2006028214 A1 | 3/2006 | |
| WO | WO-2015121863 A1 * | 8/2015 | ......... A61K 39/0275 |
| WO | 2019107385 A1 | 6/2019 | |

OTHER PUBLICATIONS

Fujiwara et al.; Gene Targeting in the Red Alga Cyanidioschyzon merolae: Single- and Multi-Copy Insertion Using Authentic and Chimeric Selection Markers; PLOS One; 2013, 8, 9, e73608 (Year: 2013).*
Google search for chlamydomonas reinhardtii rupture pH (Year: 2024).*
Google search for exogenous substances (Year: 2024).*
Goggle Search; pH of fish intestine (accessed Mar. 2025) (Year: 2025).*
Goggle Search; pH of mammal intestine (accessed Mar. 2025) (Year: 2025).*
Kwon et al.; An evaluation of microalgae as a recombinant protein oral delivery platform for fish using green fluorescent protein (GFP); Elsevier; Fish and Shellfish Immunology 87 (2019) 414-420 (Year: 2019).*
Fujiwara et al.; Gene Targeting in the Red Alga Cyanidioschyzonmerolae: Single- and Multi-Copy Insertion Using Authentic and Chimeric Selection Markers; the Public Library of Science; PLOS ONE | www.plosone.org Sep. 2013 | vol. 8 | Issue 9 | e73608 (Year: 2013).*
Machine translation of FR3064635A1 (Year: 2018).*
Google search for exogenous substances (Year: 2024) (Year: 2024).*
Google search for the Cyanidiophyceae Class (Year: 2024).*

(Continued)

*Primary Examiner* — Robert A Wax
*Assistant Examiner* — John W Lippert, III
(74) *Attorney, Agent, or Firm* — Tim Tingkang Xia, Esq.; Troutman Pepper Locke, LLP

(57) ABSTRACT

There is provided a drug delivery composition containing an acid-resistant cell that encloses a drug in the cell. In addition, there is provided an acid-resistant cell in which a drug is enclosed in the cell, where the drug is localized in the sac-shaped membrane structure included in the acid-resistant.

18 Claims, 4 Drawing Sheets
Specification includes a Sequence Listing.

(56)                    References Cited

OTHER PUBLICATIONS

Messerli et al.; Life at acidic pH imposes an increased energetic costfor a eukaryotic acidophile; The Company of Biologists; Journal of Experimental Biology Jul. 2005;208(Pt 13):2569-79. doi: 10.1242/jeb.01660. (Year: 2005).*

Google Search; does cyanidioschyzon merolae rupture at pH greater than or equal to 7 (Year: 2025).*

Google Search; is cyanidioschyzon merolae a haploid cell (Year: 2025).*

Japan Patent Office, "International Search Report for PCT Application No. PCT/JP2020/014131", Japan, Jun. 9, 2020.

J.F.S. Mann et al., Lipid vesicle size of an oral influenza vaccine delivery vehicle influences the Th1/Th2 bias in the immune response and protection against infection, Vaccine, Jun. 2, 2009, 27 (27), 3643 to 3649.

T. Nochi et al., Rice-based mucosal vaccine as a global strategy for cold-chain- and needle-free vaccination, Proc Natl Acad Sci, Jun. 26, 2007, 104 (26), 10986-10991.

J.M. Huang et al., Mucosal delivery of antigens using adsorption to bacterial spores, Vaccine, Jan. 22, 2010, 28 (4), 1021 to 1030.

S. Watanabe et al., Mitochondrial Localization of Ferrochelatase in a Red Alga Cyanidioschyzon merolae, Plant and Cell Physiology, 2013, vol. 54, No. 8.

F. Hongying et al., Oral Immunization with Recombinant lactobacillus acidophilus Expressing the Adhesin Hp0410 of Helicobacter pylori Induces Mucosal and Systemic Immune Responses, Feb. 2014, vol. 21, No. 2.

European Patent Office, "European Search Report for EP Application No. 20783288.2", Europe, Nov. 16, 2022.

Fujiwara Takayuki et al: "Gene Targeting in the Red Alga Cyanidioschyzon merolae: Single-and Multi-Copy Insertion Using Authentic and Chimeric Selection Markers", PLOS ONE, vol. 8, No. 9, Sep. 5, 2013 (Sep. 5, 2013), p. e73608, XP055822736.

Márquez-Escobar Verónica Araceli et al: "Expression of a Zika virus antigen in microalgae: Towards mucosal vaccine development", Journal of Biotechnology, Elsevier, Amsterdam NL, vol. 282, Jul. 18, 2018 (Jul. 18, 2018), pp. 86-91, XP085440270.

Elizabeth A Specht et al: "Mini Review Article Algae-based oral recombinant vaccines", Frontiers in Microbiology, vol. 5, Jan. 30, 2014 (Jan. 30, 2014), pp. 1-7, XP055357591.

Kwon Kwang-Chul et al: "An evaluation of microalgae as a recombinant protein oral delivery platform for fish using green fluorescent protein (GFP)", Fish & Shellfish Immunology, vol. 87, Jan. 28, 2019 (Jan. 28, 2019), pp. 414-420, XP085638580.

Astray Renato Mancini et al: "Rabies vaccine development by expression of recombinant viral glycoprotein", Archives of Virology, Springer Wien, AT, vol. 162, No. 2, Oct. 31, 2016 (Oct. 31, 2016), pp. 323-332, XP037121410.

Hirooka et al., Acidophilic Green Algal Genome Provides Insights Into Adaptation To An Acidic Environment, PNAS, Sep. 11, 2017, 114 (39) E8304-E8313.

* cited by examiner (A)        (B)        (C)

SEQUENCE LISTING

<160> NUMBER OF SEQ ID NOS: 66

<210> SEQ ID NO 1
<211> LENGTH: 2140
<212> TYPE: DNA
<213> ORGANISM: Rabies virus

<400> SEQUENCE: 1

```
acattttgag cctcttggat gtgaaaaaa aaaaaaaaaa aaaaaaaaaa aaaaaaaaaa        60
aaaaaaaaaa aaaaaactat taacatccct caaaagactt aaggaaagat ggttcctcag       120 gttctttgt ttgcacccct cctggttttt ccattgtgtt tcgggaagtt ccccatttac       180
acgataccag acaaacttgg tccctggagc cctattgact tacaccatct cagctgtcca       240
aataacctgg ttgtggagga cgaaggatgt accaacctgt ccgggttctc ttacatggaa       300
cttaaagtgg gatacatctc agccataaaa gtgaacgggt tcacttgcac aggtgttgtg       360
acagaggcag aaacctacac caactttgtt ggttatgtca caaccacatt caagagaaag       420
```

-continued

```
catttccgcc ccacccccaga cgcatgtaga gccgcgtata actggaagat ggccggtgac      480
cccagatatg aagagtctct acacaatccg tacccccgact accattggct tcgaactgta      540
aaaaccacca aagagtctct cgttatcata tccccaagtg tgacagattt ggacccatat       600
gacaaatccc ttcactcaag ggtcttccct ggcggaaatt gctcaggaat aacggtgtcc       660
tcgacctact gctcaactaa tcatgattac accatctgga tgcctgagaa tctgagacta       720
gggacatctt gtgacatttt tacccatagc agagggaaga gagcatccaa aggagacaag       780
acttgcggct ttgtggatga agaggcctg tataagtctt taaagggagc atgcaaactc        840
aagttatgtg gagttctcgg acttagactt atggatggaa catgggtcgc gatgcaaaca       900
tcagatgaga ccaaatggtg ccctccaggt cagttggtga atttgcacga ctttcgctca       960
gacgagattg agcatctcgt tgaggaagag ttagtcaaga aaagagagga gtgtctggat      1020
gcactagagt ccatcatgac caccaagtca gtgagtttca gacgtctcag tcacctgaga      1080
aaacttgtcc ctgggtttgg aaaagcatat accatattca acaaaaccctt gatggaggct     1140 gatgctcact acaagtctgt ccagacctgg aatgagatca tcccctcaaa agggtgtttg      1200
agagttgggg agaggtgtca tccccatgtg aacggggtgt ttttcaatgg tataatatta      1260
gggtctgacg gccatgttct aatcccagag atgcagtcat ccctcctcca gcaacatatg      1320
gagttgttgg aatcttcagt tatccccctg atgcacccct ggcagaccc ttctacagtt       1380 ttcaaagacg gtgatgaggt tgaggatttt gttgaagttc acctccccga tgtgcataaa      1440
caggtctcag gagttgacct gggtctcccg aaatgggggga agtatgtatt gatgattgca     1500
ggggccttga ttgccctgat gttgataatt ttcctgatga catgttgcag aagagtcaat      1560
cgaccagaat ctacacaaag caatcttgga gggacaggga gaaatgtgtc agtcccttcc      1620
caaagcggaa aagtcatatc ttcatgggag tcatataaga gtggaggcga gaccagactg      1680
tgaaggccgg tcatcctttt gacacctcaa gtccagagga taacctcctc tcggggttgg      1740
ggggaatctt gggatccagt agtcctcctt gaactccatc aacagggta gatttaagag        1800 tcatgagact ttcattaatc atatcagttg atcagacatg gtcgtgtaga ttctcataac       1860
acgggagatc ttctagcagt ttcagtgacc aacggtgctt tcattctcca ggaactgata       1920
ccaaaggttg tggacaagcc aagggggtgct tcggattact ctgtgcttgg gcacagaaag     1980
aggtcatagt ttgcccccttg atagcggatt caacatgaat taactaagaa aggcgatctg      2040
cctcccatga aggacataag caatagttca caatcatctt gcatctcagt gaagtgtaca      2100
taactataaa gggctgggtc atctaagcat ttcagtcgag                            2140
```

<210> SEQ ID NO 2
<211> LENGTH: 524
<212> TYPE: PRT
<213> ORGANISM: Rabies virus

<400> SEQUENCE: 2

```
Met Val Pro Gln Val Leu Leu Phe Ala Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Leu His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Val Asn Gly Phe Thr Cys
```

```
65                    70                   75                    80

Thr Gly Val Val Thr Glu Ala Glu Thr Tyr Thr Asn Phe Val Gly Tyr
                85                   90                   95

Val Thr Thr Thr Phe Lys Arg Lys His Phe Arg Pro Thr Pro Asp Ala
                100              105                  110

Cys Arg Ala Ala Tyr Asn Trp Lys Met Ala Gly Asp Pro Arg Tyr Glu
                115              120                  125

Glu Ser Leu His Asn Pro Tyr Pro Asp Tyr His Trp Leu Arg Thr Val
        130              135                  140

Lys Thr Thr Lys Glu Ser Leu Val Ile Ile Ser Pro Ser Val Thr Asp
145                  150                  155                  160

Leu Asp Pro Tyr Asp Lys Ser Leu His Ser Arg Val Phe Pro Gly Gly
                165              170                  175

Asn Cys Ser Gly Ile Thr Val Ser Ser Thr Tyr Cys Ser Thr Asn His
                180              185                  190

Asp Tyr Thr Ile Trp Met Pro Glu Asn Leu Arg Leu Gly Thr Ser Cys
        195              200                  205

Asp Ile Phe Thr His Ser Arg Gly Lys Arg Ala Ser Lys Gly Asp Lys
        210              215                  220

Thr Cys Gly Phe Val Asp Glu Arg Gly Leu Tyr Lys Ser Leu Lys Gly
225                  230                  235                  240

Ala Cys Lys Leu Lys Leu Cys Gly Val Leu Gly Leu Arg Leu Met Asp
                245              250                  255

Gly Thr Trp Val Ala Met Gln Thr Ser Asp Glu Thr Lys Trp Cys Pro
                260              265                  270

Pro Gly Gln Leu Val Asn Leu His Asp Phe Arg Ser Asp Glu Ile Glu
                275              280                  285

His Leu Val Glu Glu Glu Leu Val Lys Lys Arg Glu Glu Cys Leu Asp
        290              295                  300

Ala Leu Glu Ser Ile Met Thr Thr Lys Ser Val Ser Phe Arg Arg Leu
305                  310                  315                  320

Ser His Leu Arg Lys Leu Val Pro Gly Phe Gly Lys Ala Tyr Thr Ile
                325              330                  335

Phe Asn Lys Thr Leu Met Glu Ala Asp Ala His Tyr Lys Ser Val Gln
                340              345                  350

Thr Trp Asn Glu Ile Ile Pro Ser Lys Gly Cys Leu Arg Val Gly Glu
                355              360                  365

Arg Cys His Pro His Val Asn Gly Val Phe Phe Asn Gly Ile Ile Leu
        370              375                  380

Gly Ser Asp Gly His Val Leu Ile Pro Glu Met Gln Ser Ser Leu Leu
385                  390                  395                  400

Gln Gln His Met Glu Leu Leu Glu Ser Ser Val Ile Pro Leu Met His
                405              410                  415

Pro Leu Ala Asp Pro Ser Thr Val Phe Lys Asp Gly Asp Glu Val Glu
                420              425                  430

Asp Phe Val Glu Val His Leu Pro Asp Val His Lys Gln Val Ser Gly
        435              440                  445

Val Asp Leu Gly Leu Pro Lys Trp Gly Lys Tyr Val Leu Met Ile Ala
        450              455                  460

Gly Ala Leu Ile Ala Leu Met Leu Ile Ile Phe Leu Met Thr Cys Cys
465                  470                  475                  480

Arg Arg Val Asn Arg Pro Glu Ser Thr Gln Ser Asn Leu Gly Gly Thr
                485              490                  495
```

Gly Arg Asn Val Ser Val Pro Ser Gln Ser Gly Lys Val Ile Ser Ser
            500                 505                 510

Trp Glu Ser Tyr Lys Ser Gly Gly Glu Thr Arg Leu
        515                 520

<210> SEQ ID NO 3
<211> LENGTH: 3033
<212> TYPE: DNA
<213> ORGANISM: Cyanidioschyzon merolae

<400> SEQUENCE: 3
atgttccatg tgacgtaccc gttcacgcag agacaatgct ttctccgttc acgagaagcg      60
tgccttgcaa cgttgccagc tggtgctttt cgaaagcacc tgtggcgccc ttcgtgctgg     120
tcgttccgca cacgtcttcg taaagaggcg tcgctacgga aatccacagt tctcgctccg     180
cttactcgcc gtctgcagct gagtctcttc ggcctcccag agcggttcgt tcgcaagtcc     240
aagtcgccgg tctcggcaga gtccagtgtc gccactgagc tcacacgtga tcgggtcaaa     300
gatccgacgc tcgcgaagta ctgggataca cttctggaaa tcaatgcact ggaggcggaa     360
ctggaacaac tcaaaagcga tgaactcaga gctcgcttgg atgccctgcg agaaacgac     420 tcggtgcgga gcggggaccc gccactggcc gaggtattcg ccatcgttcg agaggccgca     480
cgtcggacgc tcagcatgcg acccttcgat gtgcaggttc ttggtggcct tgcactcttt     540
cacggttgcg tagcggagat cgccaccggt gaggggaaaa cgctcatcgc aacgatgccg     600
gcatgtgcca gcgcgctagc ggctcgcggt accgtcctgg tcgtgacggt gaacgattac     660
ctctgccgtc gcgactttga aaacatgggt ccactgtatc gctccctggg tttctctgtc     720
gggtgtgtga ccagcgccac agagcgggcg gcacgtcaac gagcatacgc ttgcgatatc     780
acctatgtga cgaatgcgga gcttggattc gactatctac gcgaccatct ggtgctgagc     840
gctgctgatc aagtgcttgt gaggcccaag cccttctact tttgtctact ggatgaggcc     900
gactcaatca tgatagatga agcgcgtaca ccgctgatca tttcccaggc tgcagaggcg     960
cccacagaga aatacgctac tgccgctaaa ctggctgcaa acctgcagcg ggatcggcac    1020
tacacggtct atgaaaagga gcgcaatgtc actttgacag gcgccggtta cgaagcatgt    1080
gaggaggcac tgcaagtgcc aacgctcttc gccgcagcgg atccgtgggc gccctttgtg    1140
ctgaatgcac tcaaggcgaa ggagctctat caacgtgata tagattatgt cgttcggggt    1200
gatcaagtgc taatcgtgga tgagtttacc ggtcgagtac tgcaaggtag gcgctggtca    1260
gagggtctgc accaggccat cgaggccaag gaggggctcg ctgtccgcac tgaaccgcgg    1320
actgtagctt ccatctcgta tcagtccttc tttcgcctgt ttcctcgtct ggcaggcatg    1380
acgggcaccg ctgctaccga tgcagcagag atacgcgaaa cgtacggact cgaggtggtc    1440
gttgtgccca ccgcgctacc tgtcgttcgc cgagactacc ccgatgtggt gtttcgaacg    1500
agtcgcggca aacttcttgc tgtggtcgca gaaattcgac gcctgcacct tcgaaaagtg    1560
cccgtcctgg ttggaaccac cagtattgaa gctagtgagc gaatcagcgc ccttttgagc    1620
gaaggcgaac gcgttccgca cgaggttctg aatgcacgtc cggagaacgc tgaacgtgag    1680
agcgaaatca tcgcccaagc aggtcgtcta ggagcggtta cgatcgcaac aaacatggct    1740
ggacgaggaa ccgatatcgt gctgggtgga aacgtgtcca gtctagcacg cgctcttctc    1800
cagagggagc tgcttgccac gttcgctctg gggcctgaat gctcctctgg ggccggcgac    1860
cgcgcatcca ccgagcattt cctctcgtgt ctcgaagagg cggagcatca ccagctgcac    1920

-continued

```
tgctttggag aaaaaatcgc tgaggcactg cgttcccagc gttcgacgga tcccggtccg        1980
cggcttatca tcgaatccat ggagcagctg catcagctga tgctgcaagc tgccgagttt        2040
caagagccaa cgttgcccttt ctctgccgag gcccaggagc tggtaagaga ggcacttcag       2100
tggctggaaa agcagctgcg tccgcggctc gatgcagagc gcgcagctgt gctggacctc        2160
ggtggcctgc acatcctcgg aactgaacga cacgagtcac gccgcatcga taaccagttg        2220
cggggtcgtg caggtcgcca aggtgacccc ggatgttcgc gtttcttcct gtcgctggag        2280
gaccccatct tcagggtgtt tgggggtgat cggatggctc gcctcgccga agcgtttcgt        2340
ctggacgaaa caaccccat cgagagcgtc caggttgcgc gtacgctgga caatgtccag         2400
cgcagcatcg agcaatatta tgcggggatt cggaagcagt tattcgctta tgatgaggtg        2460
ctttcccaac aacggaaggt actgtatcga cagcgaaacc gcttttttgga agccgatgaa       2520 gcgctcctat tcggttcgga tgcggcagca gcccgggcct ctgggggtgct tgctggcctc      2580 gcgggcgact ggatacgaac gacgattcag gatattctcc aagcaaatcg tcgagatccg        2640
gcaaaatgcg ttcagaaatt gaaagcgttc ttcccagggg cgcttctgaa cgagagcatg        2700
tgccagtccg cagcagctat cgaccaagtt gccgccgctg ttggcgtacg gctctcgcaa        2760
caccggcgga tgttgcaaca gagcgcaccg cagcaggatg ttgctgtctt tcgctatttg        2820
gcactggttc agcatgatca gctctggagt gaacatttac gaaaattagc gcttttgcgg        2880
gacatgtcgt ctttgcagac gttgcggcag gtagatccgt tgcaacagta tcagcaagat        2940
agttttcagc tctttgaaca gatgatggca caaataaggc gcaacactgt atactcgttt        3000
ttcaagtatt cgccggggcc aacggtatcc gcg                                     3033
```

```
<210> SEQ ID NO 4
<211> LENGTH: 1011
<212> TYPE: PRT
<213> ORGANISM: Cyanidioschyzon merolae

<400> SEQUENCE: 4

Met Phe His Val Thr Tyr Pro Phe Thr Gln Arg Gln Cys Phe Leu Arg
1               5                   10                  15

Ser Arg Glu Ala Cys Leu Ala Thr Leu Pro Ala Gly Ala Phe Arg Lys
            20                  25                  30

His Leu Trp Arg Pro Ser Cys Trp Ser Phe Arg Thr Arg Leu Arg Lys
        35                  40                  45

Glu Ala Ser Leu Arg Lys Ser Thr Val Leu Ala Pro Leu Thr Arg Arg
    50                  55                  60

Leu Gln Leu Ser Leu Phe Gly Leu Pro Glu Arg Phe Val Arg Lys Ser
65                  70                  75                  80

Lys Ser Pro Val Ser Ala Glu Ser Ser Val Ala Thr Glu Leu Thr Arg
                85                  90                  95

Asp Arg Val Lys Asp Pro Thr Leu Ala Lys Tyr Trp Asp Thr Leu Leu
            100                 105                 110

Glu Ile Asn Ala Leu Glu Ala Glu Leu Glu Gln Leu Lys Ser Asp Glu
        115                 120                 125

Leu Arg Ala Arg Leu Asp Ala Leu Arg Arg Asn Asp Ser Val Arg Ser
    130                 135                 140

Gly Asp Pro Pro Leu Ala Glu Val Phe Ala Ile Val Arg Glu Ala Ala
145                 150                 155                 160

Arg Arg Thr Leu Ser Met Arg Pro Phe Asp Val Gln Val Leu Gly Gly
                165                 170                 175
```

-continued

```
Leu Ala Leu Phe His Gly Cys Val Ala Glu Ile Ala Thr Gly Glu Gly
            180                 185                 190

Lys Thr Leu Ile Ala Thr Met Pro Ala Cys Ala Ser Ala Leu Ala Ala
            195                 200                 205

Arg Gly Thr Val Leu Val Val Thr Val Asn Asp Tyr Leu Cys Arg Arg
    210                 215                 220

Asp Phe Glu Asn Met Gly Pro Leu Tyr Arg Ser Leu Gly Phe Ser Val
225                 230                 235                 240

Gly Cys Val Thr Ser Ala Thr Glu Arg Ala Ala Arg Gln Arg Ala Tyr
                245                 250                 255

Ala Cys Asp Ile Thr Tyr Val Thr Asn Ala Glu Leu Gly Phe Asp Tyr
            260                 265                 270

Leu Arg Asp His Leu Val Leu Ser Ala Ala Asp Gln Val Leu Val Arg
            275                 280                 285

Pro Lys Pro Phe Tyr Phe Cys Leu Leu Asp Glu Ala Asp Ser Ile Met
    290                 295                 300

Ile Asp Glu Ala Arg Thr Pro Leu Ile Ile Ser Gln Ala Ala Glu Ala
305                 310                 315                 320

Pro Thr Glu Lys Tyr Ala Thr Ala Ala Lys Leu Ala Ala Asn Leu Gln
                325                 330                 335

Arg Asp Arg His Tyr Thr Val Tyr Glu Lys Glu Arg Asn Val Thr Leu
            340                 345                 350

Thr Gly Ala Gly Tyr Glu Ala Cys Glu Glu Ala Leu Gln Val Pro Thr
            355                 360                 365

Leu Phe Ala Ala Ala Asp Pro Trp Ala Pro Phe Val Leu Asn Ala Leu
    370                 375                 380

Lys Ala Lys Glu Leu Tyr Gln Arg Asp Ile Asp Tyr Val Val Arg Gly
385                 390                 395                 400

Asp Gln Val Leu Ile Val Asp Glu Phe Thr Gly Arg Val Leu Gln Gly
                405                 410                 415

Arg Arg Trp Ser Glu Gly Leu His Gln Ala Ile Glu Ala Lys Glu Gly
            420                 425                 430

Leu Ala Val Arg Thr Glu Pro Arg Thr Val Ala Ser Ile Ser Tyr Gln
            435                 440                 445

Ser Phe Phe Arg Leu Phe Pro Arg Leu Ala Gly Met Thr Gly Thr Ala
    450                 455                 460

Ala Thr Asp Ala Ala Glu Ile Arg Glu Thr Tyr Gly Leu Glu Val Val
465                 470                 475                 480

Val Val Pro Thr Ala Leu Pro Val Val Arg Arg Asp Tyr Pro Asp Val
                485                 490                 495

Val Phe Arg Thr Ser Arg Gly Lys Leu Leu Ala Val Val Ala Glu Ile
            500                 505                 510

Arg Arg Leu His Leu Arg Lys Val Pro Val Leu Val Gly Thr Thr Ser
            515                 520                 525

Ile Glu Ala Ser Glu Arg Ile Ser Ala Leu Leu Ser Glu Gly Glu Arg
    530                 535                 540

Val Pro His Glu Val Leu Asn Ala Arg Pro Glu Asn Ala Glu Arg Glu
545                 550                 555                 560

Ser Glu Ile Ile Ala Gln Ala Gly Arg Leu Gly Ala Val Thr Ile Ala
                565                 570                 575

Thr Asn Met Ala Gly Arg Gly Thr Asp Ile Val Leu Gly Gly Asn Val
            580                 585                 590

Ser Ser Leu Ala Arg Ala Leu Leu Gln Arg Glu Leu Leu Ala Thr Phe
```

-continued

```
                595                  600                  605

Ala Leu Gly Pro Glu Cys Ser Ser Gly Ala Gly Asp Arg Ala Ser Thr
    610                  615                  620

Glu His Phe Leu Ser Cys Leu Glu Glu Ala Glu His His Gln Leu His
625                  630                  635                  640

Cys Phe Gly Glu Lys Ile Ala Glu Ala Leu Arg Ser Gln Arg Ser Thr
                645                  650                  655

Asp Pro Gly Pro Arg Leu Ile Ile Glu Ser Met Glu Gln Leu His Gln
                660                  665                  670

Leu Met Leu Gln Ala Ala Glu Phe Gln Glu Pro Thr Leu Pro Phe Ser
            675                  680                  685

Ala Glu Ala Gln Glu Leu Val Arg Glu Ala Leu Gln Trp Leu Glu Lys
    690                  695                  700

Gln Leu Arg Pro Arg Leu Asp Ala Glu Arg Ala Ala Val Leu Asp Leu
705                  710                  715                  720

Gly Gly Leu His Ile Leu Gly Thr Glu Arg His Glu Ser Arg Arg Ile
                725                  730                  735

Asp Asn Gln Leu Arg Gly Arg Ala Gly Arg Gln Gly Asp Pro Gly Cys
                740                  745                  750

Ser Arg Phe Phe Leu Ser Leu Glu Asp Pro Ile Phe Arg Val Phe Gly
            755                  760                  765

Gly Asp Arg Met Ala Arg Leu Ala Glu Ala Phe Arg Leu Asp Glu Thr
    770                  775                  780

Thr Pro Ile Glu Ser Val Gln Val Ala Arg Thr Leu Asp Asn Val Gln
785                  790                  795                  800

Arg Ser Ile Glu Gln Tyr Tyr Ala Gly Ile Arg Lys Gln Leu Phe Ala
                805                  810                  815

Tyr Asp Glu Val Leu Ser Gln Gln Arg Lys Val Leu Tyr Arg Gln Arg
            820                  825                  830

Asn Arg Phe Leu Glu Ala Asp Glu Ala Leu Leu Phe Gly Ser Asp Ala
            835                  840                  845

Ala Ala Ala Arg Ala Ser Gly Val Leu Ala Gly Leu Ala Gly Asp Trp
    850                  855                  860

Ile Arg Thr Thr Ile Gln Asp Ile Leu Gln Ala Asn Arg Arg Asp Pro
865                  870                  875                  880

Ala Lys Cys Val Gln Lys Leu Lys Ala Phe Phe Pro Gly Ala Leu Leu
                885                  890                  895

Asn Glu Ser Met Cys Gln Ser Ala Ala Ala Ile Asp Gln Val Ala Ala
                900                  905                  910

Ala Val Gly Val Arg Leu Ser Gln His Arg Arg Met Leu Gln Gln Ser
            915                  920                  925

Ala Pro Gln Gln Asp Val Ala Val Phe Arg Tyr Leu Ala Leu Val Gln
    930                  935                  940

His Asp Gln Leu Trp Ser Glu His Leu Arg Lys Leu Ala Leu Leu Arg
945                  950                  955                  960

Asp Met Ser Ser Leu Gln Thr Leu Arg Gln Val Asp Pro Leu Gln Gln
                965                  970                  975

Tyr Gln Gln Asp Ser Phe Gln Leu Phe Glu Gln Met Met Ala Gln Ile
            980                  985                  990

Arg Arg Asn Thr Val Tyr Ser Phe  Phe Lys Tyr Ser Pro  Gly Pro Thr
            995                  1000                 1005

Val Ser  Ala
    1010
```

-continued

```
<210> SEQ ID NO 5
<211> LENGTH: 390
<212> TYPE: DNA
<213> ORGANISM: Cyanidioschyzon merolae

<400> SEQUENCE: 5
atgttccatg tgacgtaccc gttcacgcag agacaatgct ttctccgttc acgagaagcg      60
tgccttgcaa cgttgccagc tggtgctttt cgaaagcacc tgtggcgccc ttcgtgctgg     120
tcgttccgca cacgtcttcg taaagaggcg tcgctacgga aatccacagt tctcgctccg     180
cttactcgcc gtctgcagct gagtctcttc ggcctccag agcggttcgt tcgcaagtcc       240
aagtcgccgg tctcggcaga gtccagtgtc gccactgagc tcacacgtga tcgggtcaaa      300
gatccgacgc tcgcgaagta ctgggataca cttctggaaa tcaatgcact ggaggcggaa      360
ctggaacaac tcaaaagcga tgaactcaga                                     390

<210> SEQ ID NO 6
<211> LENGTH: 130
<212> TYPE: PRT
<213> ORGANISM: Cyanidioschyzon merolae

<400> SEQUENCE: 6

Met Phe His Val Thr Tyr Pro Phe Thr Gln Arg Gln Cys Phe Leu Arg
1               5                   10                  15

Ser Arg Glu Ala Cys Leu Ala Thr Leu Pro Ala Gly Ala Phe Arg Lys
            20                  25                  30

His Leu Trp Arg Pro Ser Cys Trp Ser Phe Arg Thr Arg Leu Arg Lys
        35                  40                  45

Glu Ala Ser Leu Arg Lys Ser Thr Val Leu Ala Pro Leu Thr Arg Arg
    50                  55                  60

Leu Gln Leu Ser Leu Phe Gly Leu Pro Glu Arg Phe Val Arg Lys Ser
65                  70                  75                  80

Lys Ser Pro Val Ser Ala Glu Ser Ser Val Ala Thr Glu Leu Thr Arg
                85                  90                  95

Asp Arg Val Lys Asp Pro Thr Leu Ala Lys Tyr Trp Asp Thr Leu Leu
            100                 105                 110

Glu Ile Asn Ala Leu Glu Ala Glu Leu Glu Gln Leu Lys Ser Asp Glu
        115                 120                 125

Leu Arg
    130

<210> SEQ ID NO 7
<211> LENGTH: 1389
<212> TYPE: DNA
<213> ORGANISM: Cyanidioschyzon merolae

<400> SEQUENCE: 7
atgagcgtat cttgtggacg gcggatcttt tcagacattg tgcgtcaagt acgcacgttt      60
gctaccgtgg gcgtagacgc tcgctcgctt gcaggtacac gcaacgccac ggtctggcga     120
tcgtaccgca cgacgacgtt gcagtacccg cggctttggg aactgcgcgc ttcgcgcttc     180
ctctcaggtg aggcggtgga ggcgagtgca agcaaacgca agccccatct gaatgttggc     240
ggtatgggtc acgttgacca tgggaaaact acgctcgcgg cagcgattac gaaagtgctc     300
gccgagactg tggagcccg gtacactgct tacgaagaga ttgacaaggc accggaggag      360
cgcgcccgcg ggatcacgat caacgcttcg catctcaaat acgagactcc atcacgttcg     420
```

-continued

```
tatgcacatg tcgattgccc tgggcatcga gactttgtga agaactttat cacgggtgcg      480
gcacaggtcg acaccgcgat tctcgtggtc agcggcccgg acggcccgca gccgcagact      540
caagagcacg tactgctatc gaagcaggta ggtgttccga actttgttgt atacctgaac      600
aaatgtgata tggtcgacga tccggaactt ttggacttgg tcgaattaga ggtgcgtgaa      660
ctactcagca agtacgaata cgatggcgac aacgtgccga tcgtgcgggg ctctgccctg      720
aaggcattgc agggcgatca gagcgagctt ggctgtgggt ccatccacaa gctcctggag      780
attctcgaca aggtcccaat acccaaaaga gaccttgaaa aaccgttcct gatgcccatt      840
gaagatagct ttagcattac tggccgagga acggtggtta cgggacgcgt ggagaccggt      900
atcctacgcc ctggtgatga aatcgaaatc gtcggacttc gtcctcccga ggtagcacca      960
atgcgcacga tcgtcaccgg tatcgagact ttcaagcagt cgcttcctta cgcagaggct     1020
ggcgagaatg ttggctgtct gcttcgcggg gtcaagcgcg aagacgtgtt cgcgcggtcag    1080 gttctagcga aaccgggaac ctccagagcg caccgcaagt cgaggctga cgtttacatt      1140 cttactcagg aggaaggcgg ccgccataca ccattcttca gcaactatcg tcctcaattc     1200
ttcgtgcgga ctgcagatgt cacaggacgc ttccttctgc cgccagaagt ggagatgtgc     1260
atgccaggag atcgcgtacg atgcgctgtt gagctcatct atccggtcgc gctgcaggaa     1320
ggcttacgtt tcgctgttcg tgagggcggc aggaccgtcg gtgctgggtt ggttacgaaa     1380
gtcatcgag                                                            1389
```

```
<210> SEQ ID NO 8
<211> LENGTH: 463
<212> TYPE: PRT
<213> ORGANISM: Cyanidioschyzon merolae

<400> SEQUENCE: 8

Met Ser Val Ser Cys Gly Arg Arg Ile Phe Ser Asp Ile Val Arg Gln
1               5                   10                  15

Val Arg Thr Phe Ala Thr Val Gly Val Asp Ala Arg Ser Leu Ala Gly
            20                  25                  30

Thr Arg Asn Ala Thr Val Trp Arg Ser Tyr Arg Thr Thr Thr Leu Gln
        35                  40                  45

Tyr Pro Arg Leu Trp Glu Leu Arg Ala Ser Arg Phe Leu Ser Gly Glu
    50                  55                  60

Ala Val Glu Ala Ser Ala Ser Lys Arg Lys Pro His Leu Asn Val Gly
65                  70                  75                  80

Gly Met Gly His Val Asp His Gly Lys Thr Thr Leu Ala Ala Ala Ile
                85                  90                  95

Thr Lys Val Leu Ala Glu Thr Gly Gly Ala Arg Tyr Thr Ala Tyr Glu
            100                 105                 110

Glu Ile Asp Lys Ala Pro Glu Glu Arg Ala Arg Gly Ile Thr Ile Asn
        115                 120                 125

Ala Ser His Leu Lys Tyr Glu Thr Pro Ser Arg Ser Tyr Ala His Val
    130                 135                 140

Asp Cys Pro Gly His Arg Asp Phe Val Lys Asn Phe Ile Thr Gly Ala
145                 150                 155                 160

Ala Gln Val Asp Thr Ala Ile Leu Val Val Ser Gly Pro Asp Gly Pro
                165                 170                 175

Gln Pro Gln Thr Gln Glu His Val Leu Leu Ser Lys Gln Val Gly Val
            180                 185                 190
```

-continued

```
Pro Asn Phe Val Val Tyr Leu Asn Lys Cys Asp Met Val Asp Asp Pro
        195                 200                 205

Glu Leu Leu Asp Leu Val Glu Leu Glu Val Arg Glu Leu Leu Ser Lys
    210                 215                 220

Tyr Glu Tyr Asp Gly Asp Asn Val Pro Ile Val Arg Gly Ser Ala Leu
225                 230                 235                 240

Lys Ala Leu Gln Gly Asp Gln Ser Glu Leu Gly Cys Gly Ser Ile His
                245                 250                 255

Lys Leu Leu Glu Ile Leu Asp Lys Val Pro Ile Pro Lys Arg Asp Leu
                260                 265                 270

Glu Lys Pro Phe Leu Met Pro Ile Glu Asp Ser Phe Ser Ile Thr Gly
            275                 280                 285

Arg Gly Thr Val Val Thr Gly Arg Val Glu Thr Gly Ile Leu Arg Pro
    290                 295                 300

Gly Asp Glu Ile Glu Ile Val Gly Leu Arg Pro Pro Glu Val Ala Pro
305                 310                 315                 320

Met Arg Thr Ile Val Thr Gly Ile Glu Thr Phe Lys Gln Ser Leu Pro
                325                 330                 335

Tyr Ala Glu Ala Gly Glu Asn Val Gly Cys Leu Leu Arg Gly Val Lys
                340                 345                 350

Arg Glu Asp Val Leu Arg Gly Gln Val Leu Ala Lys Pro Gly Thr Ser
            355                 360                 365

Arg Ala His Arg Lys Phe Glu Ala Asp Val Tyr Ile Leu Thr Gln Glu
    370                 375                 380

Glu Gly Gly Arg His Thr Pro Phe Phe Ser Asn Tyr Arg Pro Gln Phe
385                 390                 395                 400

Phe Val Arg Thr Ala Asp Val Thr Gly Arg Phe Leu Leu Pro Pro Glu
                405                 410                 415

Val Glu Met Cys Met Pro Gly Asp Arg Val Arg Cys Ala Val Glu Leu
                420                 425                 430

Ile Tyr Pro Val Ala Leu Gln Glu Gly Leu Arg Phe Ala Val Arg Glu
            435                 440                 445

Gly Gly Arg Thr Val Gly Ala Gly Leu Val Thr Lys Val Ile Glu
    450                 455                 460
```

```
<210> SEQ ID NO 9
<211> LENGTH: 234
<212> TYPE: DNA
<213> ORGANISM: Cyanidioschyzon merolae

<400> SEQUENCE: 9
atgagcgtat cttgtggacg gcggatcttt tcagacattg tgcgtcaagt acgcacgttt      60
gctaccgtgg gcgtagacgc tcgctcgctt gcaggtacac gcaacgccac ggtctggcga     120
tcgtaccgca cgacgacgtt gcagtacccg cggctttggg aactgcgcgc ttcgcgcttc     180
ctctcaggtg aggcggtgga ggcgagtgca agcaaacgca agccccatct gaat           234
```

```
<210> SEQ ID NO 10
<211> LENGTH: 78
<212> TYPE: PRT
<213> ORGANISM: Cyanidioschyzon merolae

<400> SEQUENCE: 10
```

```
Met Ser Val Ser Cys Gly Arg Arg Ile Phe Ser Asp Ile Val Arg Gln
1               5                   10                  15

Val Arg Thr Phe Ala Thr Val Gly Val Asp Ala Arg Ser Leu Ala Gly
```

-continued

```
                 20              25              30

Thr Arg Asn Ala Thr Val Trp Arg Ser Tyr Arg Thr Thr Thr Leu Gln
        35              40              45

Tyr Pro Arg Leu Trp Glu Leu Arg Ala Ser Arg Phe Leu Ser Gly Glu
    50              55              60

Ala Val Glu Ala Ser Ala Ser Lys Arg Lys Pro His Leu Asn
65              70              75

<210> SEQ ID NO 11
<211> LENGTH: 690
<212> TYPE: DNA
<213> ORGANISM: Cyanidioschyzon merolae

<400> SEQUENCE: 11
atgggcgttc cgcaaatcac aagcaacacc gtggcacccg tcgaacgcaa ggtggagcgc      60
ggaagctacg gtgcaactgc gccagcagcg ccggcagctg cgttcgcctc caccgagtcc     120
gagctgatca gggatagtga cccttcgctc tcaacgatgt ggttgccggt ggatctgagt     180
gtccaactca ctccgaagga gcgtctgcag ctggcgtggt cggcggcacg gccgtggcga     240
gagtgggctg cactgcacgc actagcgccg ccgccaccct cgtcgtggct ggactggagc     300
gctcgtgtgc gcacgaattt ggagctctac gcatggaact acctctttgt ggcccttgtg     360
atgttcattg tgacgggttt gttctatccg tggagtgcgc tgctcctaat atcctggctc     420
ctgctcgcgc tgtacatggg tgtacgcacg gctgatgccg tcgggggcga ggacgcttcg     480
ctgggcgcgc gcatgttcca gaactggcct ggctatatcc gatacatttt gctgggtggc     540
ttgctcacgc tcatgttgtt tctgacagac gttgtcgcct tggcgctcac cagcgcatcg     600
ttggccgcag ctgtgacgct cgcgcacgca gcgctccacg atcccgttgc cgtgctctcc     660
gcgcggaatg ccgaatatac cgtggcaccg                                      690

<210> SEQ ID NO 12
<211> LENGTH: 230
<212> TYPE: PRT
<213> ORGANISM: Cyanidioschyzon merolae

<400> SEQUENCE: 12

Met Gly Val Pro Gln Ile Thr Ser Asn Thr Val Ala Pro Val Glu Arg
1               5               10              15

Lys Val Glu Arg Gly Ser Tyr Gly Ala Thr Ala Pro Ala Ala Pro Ala
        20              25              30

Ala Ala Phe Ala Ser Thr Glu Ser Glu Leu Ile Arg Asp Ser Asp Pro
        35              40              45

Ser Leu Ser Thr Met Trp Leu Pro Val Asp Leu Ser Val Gln Leu Thr
    50              55              60

Pro Lys Glu Arg Leu Gln Leu Ala Trp Ser Ala Ala Arg Pro Trp Arg
65              70              75              80

Glu Trp Ala Ala Leu His Ala Leu Ala Pro Pro Pro Ser Ser Trp
                85              90              95

Leu Asp Trp Ser Ala Arg Val Arg Thr Asn Leu Glu Leu Tyr Ala Trp
            100             105             110

Asn Tyr Leu Phe Val Ala Leu Val Met Phe Ile Val Thr Gly Leu Phe
        115             120             125

Tyr Pro Trp Ser Ala Leu Leu Leu Ile Ser Trp Leu Leu Leu Ala Leu
    130             135             140

Tyr Met Gly Val Arg Thr Ala Asp Ala Val Gly Gly Glu Asp Ala Ser
```

-continued

```
145             150             155             160

Leu Gly Ala Arg Met Phe Gln Asn Trp Pro Gly Tyr Ile Arg Tyr Ile
                165             170             175

Leu Leu Gly Gly Leu Leu Thr Leu Met Leu Phe Leu Thr Asp Val Val
            180             185             190

Ala Leu Ala Leu Thr Ser Ala Ser Leu Ala Ala Ala Val Thr Leu Ala
            195             200             205

His Ala Ala Leu His Asp Pro Val Ala Val Leu Ser Ala Arg Asn Ala
        210             215             220

Glu Tyr Thr Val Ala Pro
225             230

<210> SEQ ID NO 13
<211> LENGTH: 1287
<212> TYPE: DNA
<213> ORGANISM: Cyanidioschyzon merolae

<400> SEQUENCE: 13
atggtgatca gcacccaggg aaacgtctca ggttccgttc cgaatacgct cagagcgaaa      60
cctgagcaaa cgcttcaggc gtcgaggcct gccaccaggg ccgtctctgc agcgcttgac     120
ttctgcgctg gagttgcagc agccgtttca ggtatatctg ttcccggggg atattttccc     180
cctttcatgt cattcagcaa ccgcttaagt ccaaaagctg gcacagatac tctttcggtg     240
agcaatcagg agtcaaccag ggaagacgcg gacgctgtgc tttcgacggc agccgcttcg     300
ctggcaacgg acctcgagta cggctccgcg acagagaggc accacgagaa catcgatcct     360
attcgcccag tgacgcgaga ctctggcgca ttcgtcgaga actatccaag tggaacacgg     420
gaggtggcaa tcgctttcga aggagtgacg ttgtctgcga gcacccaggc ggcggggacg     480
actcgaccca tacttcggaa tatctgtttc gaagtacgcg acggagagac ggtgtttatc     540
atcggcccgt caggagctgg caagtctcga cttcttcgac tggtgaaccg cttagaggag     600
ccttcaggtg gtcaagtccg gctgtggggc acaccagtgc cagcgtaccc tccaggcgag     660
ttacggggca aactagtagg ttttctgagc cagcaacctg cattgccgtg tttggcacat     720
aggaggcctg gtttgctgga ggcactccgc cgacttgtaa cgcgagaaac gctttgggag     780
ctggtcctcg gcaaacgccg acaacgctcg agcgcgaaca cggaggaacc agcaaagtcg     840
gcgctcgaga cgctcgttcg tttgggagtt gtatcgcgga cagagcttga acagcgacta     900
ccggaagcac tgcatatagc tggcttatcg cgaacgattc tggatcgacc gctagccgcc     960
ttgtcagggg gtgagcgagc tcgcctcggc ctcacgcgcg tgcttttgca gcaaccacga    1020
atcctactgc tggacgaggt cacttcaagt ctggacgcag caacagcggc tcaagtattg    1080
caacgtttat cggactggaa agaacgcatc cgggccacaa tactcatagt gacgcacaga    1140
ctctcggagg ttaccgacgg ccagctcatt cttgtgcggg acgggagct gttcttacgc    1200 ggtgacgcgc gtgcgctgct cggtaccgcc gatacagcgg ccagcattca tcggctttg    1260 actggggagt cattgggagc aacaaaa                                        1287

<210> SEQ ID NO 14
<211> LENGTH: 429
<212> TYPE: PRT
<213> ORGANISM: Cyanidioschyzon merolae

<400> SEQUENCE: 14

Met Val Ile Ser Thr Gln Gly Asn Val Ser Gly Ser Val Pro Asn Thr
1               5               10              15
```

-continued

```
Leu Arg Ala Lys Pro Glu Gln Thr Leu Gln Ala Ser Arg Pro Ala Thr
            20                  25                  30

Arg Ala Val Ser Ala Ala Leu Asp Phe Cys Ala Gly Val Ala Ala Ala
            35                  40                  45

Val Ser Gly Ile Ser Val Pro Gly Gly Tyr Phe Pro Pro Phe Met Ser
    50                  55                  60

Phe Ser Asn Arg Leu Ser Pro Lys Ala Gly Thr Asp Thr Leu Ser Val
65                  70                  75                  80

Ser Asn Gln Glu Ser Thr Arg Glu Asp Ala Asp Ala Val Leu Ser Thr
                85                  90                  95

Ala Ala Ala Ser Leu Ala Thr Asp Leu Glu Tyr Gly Ser Ala Thr Glu
            100                 105                 110

Arg His His Glu Asn Ile Asp Pro Ile Arg Pro Val Thr Arg Asp Ser
            115                 120                 125

Gly Ala Phe Val Glu Asn Tyr Pro Ser Gly Thr Arg Glu Val Ala Ile
    130                 135                 140

Ala Phe Glu Gly Val Thr Leu Ser Ala Ser Thr Gln Ala Ala Gly Thr
145                 150                 155                 160

Thr Arg Pro Ile Leu Arg Asn Ile Cys Phe Glu Val Arg Asp Gly Glu
                165                 170                 175

Thr Val Phe Ile Ile Gly Pro Ser Gly Ala Gly Lys Ser Arg Leu Leu
                180                 185                 190

Arg Leu Val Asn Arg Leu Glu Glu Pro Ser Gly Gly Gln Val Arg Leu
            195                 200                 205

Trp Gly Thr Pro Val Pro Ala Tyr Pro Pro Gly Glu Leu Arg Gly Lys
    210                 215                 220

Leu Val Gly Phe Leu Ser Gln Gln Pro Ala Leu Pro Cys Leu Ala His
225                 230                 235                 240

Arg Arg Pro Gly Leu Leu Glu Ala Leu Arg Arg Leu Val Thr Arg Glu
                245                 250                 255

Thr Leu Trp Glu Leu Val Leu Gly Lys Arg Arg Gln Arg Ser Ser Ala
                260                 265                 270

Asn Thr Glu Glu Pro Ala Lys Ser Ala Leu Glu Thr Leu Val Arg Leu
            275                 280                 285

Gly Val Val Ser Arg Thr Glu Leu Glu Gln Arg Leu Pro Glu Ala Leu
    290                 295                 300

His Ile Ala Gly Leu Ser Arg Thr Ile Leu Asp Arg Pro Leu Ala Ala
305                 310                 315                 320

Leu Ser Gly Gly Glu Arg Ala Arg Leu Gly Leu Thr Arg Val Leu Leu
                325                 330                 335

Gln Gln Pro Arg Ile Leu Leu Leu Asp Glu Val Thr Ser Ser Leu Asp
            340                 345                 350

Ala Ala Thr Ala Ala Gln Val Leu Gln Arg Leu Ser Asp Trp Lys Glu
            355                 360                 365

Arg Ile Arg Ala Thr Ile Leu Ile Val Thr His Arg Leu Ser Glu Val
    370                 375                 380

Thr Asp Gly Gln Leu Ile Leu Val Arg Asp Gly Glu Leu Phe Leu Arg
385                 390                 395                 400

Gly Asp Ala Arg Ala Leu Leu Gly Thr Ala Asp Thr Ala Ala Ser Ile
                405                 410                 415

His Arg Leu Leu Thr Gly Glu Ser Leu Gly Ala Thr Lys
            420                 425
```

-continued

<210> SEQ ID NO 15
<211> LENGTH: 1362
<212> TYPE: DNA
<213> ORGANISM: Cyanidioschyzon merolae

<400> SEQUENCE: 15
atgtcgtcca tctgggagca aatgagatct ctgctgttcg gagcgagtgg atcgtatgct        60
gatgcggccg acacacccca agggcttgct ttcgaacagc gacttgttgc gaggcacgga       120
aacacgctgc cgccttggcc gctcttcaag ctgggtgctg tatacggcgt tggaccagtg       180
cctcccaacc tgcgggccct tctagacggt tctttctttc tgataggcgc gtgtttgggg       240
actgcggcgc tgtttgactt tgccggtatc atcggtagac gcggcggcgg cgttactgca       300
gcggaagttg cgaaagagtg caactgtgcc gatgtcaatg cggtcggtcg cgttctacgg       360
gcttgcgaaa actgggctca ctttgagtcc tacgtcccgc gggactgtga ctcaaagagc       420
gtatcgaacg agcagcgctt atggcggaac acactattat cggctttatt gcgcgaggat       480
catccacaca gcgtgcgcgc tcaaataatg cacttgtacg tcgatatttt tcccgcgagt       540
gcgcttctct ttgagacgat acgtgatacg ccgtcaaacg acgtagaaac ggacggtttg       600
cgagcgcgtg ccgatgcgtc agcgacaaaa caaccgagcg cgtttgaacg cgtccatcag       660
tgtacgtttt gggaatacct gtcgagccat ccggatcgat gggatgtctt caacagggcc       720
atgcgtagct cagatgcgct cctgggatcg acgatcatga agatatcga ctggggacgc        780 tacctccggg ttatagacct cggcgcagcg gatggttcac tcgtttatca tctgctgagc       840
gctttcgcgc tgaaggcagt gattttcgat ctgccgccgg ttatcgagca tgccaaggcg       900
tactggaaca cgagtccgga gcgctcggca atggtcgcaa gtggccgcgt ccagttcgcg       960
gccggcgacc ttttcgacgc caccaccgtg ccagcagcgg aggaaggcga catctatgtg      1020
atgcgcaata tctggcacga ctggcgcgat cccgactgta tccgcattgg ccggagtgtt      1080
cgagcagcaa tcgcgacgt tcgcaatgtg aagctcgtca tcctggaggc aagcattgac      1140
cagtatccgc gcggctcact ccttgagcgc tttcgcgttg cactcgatca aatcatgttt      1200
accgcatttc gatccaagga acgcgacagg atagagtttg atgcgctctt acgtcgatgt      1260
ggttttcagc tgaccgaagt gaggcattta cgcgcatcac tcgtcgcagt gatcgccgag      1320
ccgctttcgc attgggtcca gtctcctgaa ccagcggacc aa                        1362

<210> SEQ ID NO 16
<211> LENGTH: 454
<212> TYPE: PRT
<213> ORGANISM: Cyanidioschyzon merolae

<400> SEQUENCE: 16

Met Ser Ser Ile Trp Glu Gln Met Arg Ser Leu Leu Phe Gly Ala Ser
1               5                   10                  15

Gly Ser Tyr Ala Asp Ala Ala Asp Thr Pro Gln Gly Leu Ala Phe Glu
                20                  25                  30

Gln Arg Leu Val Ala Arg His Gly Asn Thr Leu Pro Pro Trp Pro Leu
            35                  40                  45

Phe Lys Leu Gly Ala Val Tyr Gly Val Gly Pro Val Pro Pro Asn Leu
        50                  55                  60

Arg Ala Leu Leu Asp Gly Ser Phe Phe Leu Ile Gly Ala Cys Leu Gly
65                  70                  75                  80

Thr Ala Ala Leu Phe Asp Phe Ala Gly Ile Ile Gly Arg Arg Gly Gly
                85                  90                  95

```
Gly Val Thr Ala Ala Glu Val Ala Lys Glu Cys Asn Cys Ala Asp Val
            100                 105                 110

Asn Ala Val Gly Arg Val Leu Arg Ala Cys Glu Asn Trp Gly Tyr Phe
            115                 120                 125

Glu Ser Tyr Val Pro Arg Asp Cys Asp Ser Lys Ser Val Ser Asn Glu
            130                 135                 140

Gln Arg Leu Trp Arg Asn Thr Leu Leu Ser Ala Leu Leu Arg Glu Asp
145                 150                 155                 160

His Pro His Ser Val Arg Ala Gln Ile Met His Leu Tyr Val Asp Ile
                    165                 170                 175

Phe Pro Ala Ser Ala Leu Leu Phe Glu Thr Ile Arg Asp Thr Pro Ser
                    180                 185                 190

Asn Asp Val Glu Thr Asp Gly Leu Arg Ala Arg Ala Asp Ala Ser Ala
                    195                 200                 205

Thr Lys Gln Pro Ser Ala Phe Glu Arg Val His Gln Cys Thr Phe Trp
            210                 215                 220

Glu Tyr Leu Ser Ser His Pro Asp Arg Trp Asp Val Phe Asn Arg Ala
225                 230                 235                 240

Met Arg Ser Ser Asp Ala Leu Leu Gly Ser Thr Ile Met Lys Asp Ile
                    245                 250                 255

Asp Trp Gly Arg Tyr Leu Arg Val Ile Asp Leu Gly Ala Ala Asp Gly
                    260                 265                 270

Ser Leu Val Tyr His Leu Leu Ser Ala Phe Ala Leu Lys Ala Val Ile
            275                 280                 285

Phe Asp Leu Pro Pro Val Ile Glu His Ala Lys Ala Tyr Trp Asn Thr
290                 295                 300

Ser Pro Glu Arg Ser Ala Met Val Ala Ser Gly Arg Val Gln Phe Ala
305                 310                 315                 320

Ala Gly Asp Leu Phe Asp Ala Thr Thr Val Pro Ala Ala Glu Glu Gly
                    325                 330                 335

Asp Ile Tyr Val Met Arg Asn Ile Trp His Asp Trp Arg Asp Pro Asp
                    340                 345                 350

Cys Ile Arg Ile Gly Arg Ser Val Arg Ala Ala Ile Gly Asp Val Arg
            355                 360                 365

Asn Val Lys Leu Val Ile Leu Glu Ala Ser Ile Asp Gln Tyr Pro Arg
            370                 375                 380

Gly Ser Leu Leu Glu Arg Phe Arg Val Ala Leu Asp Gln Ile Met Phe
385                 390                 395                 400

Thr Ala Phe Arg Ser Lys Glu Arg Asp Arg Ile Glu Phe Asp Ala Leu
                    405                 410                 415

Leu Arg Arg Cys Gly Phe Gln Leu Thr Glu Val Arg His Leu Arg Ala
                    420                 425                 430

Ser Leu Val Ala Val Ile Ala Glu Pro Leu Ser His Trp Val Gln Ser
            435                 440                 445

Pro Glu Pro Ala Asp Gln
    450
```

```
<210> SEQ ID NO 17
<211> LENGTH: 1488
<212> TYPE: DNA
<213> ORGANISM: Cyanidioschyzon merolae

<400> SEQUENCE: 17
atggacccaa ccaagtatac accacgcgat acttttgacg tgaacgtgct taccacgaac      60
```

-continued

```
gctgggcagc cggtgacgaa caaccagtct tcacgcactg tggggccgcg tggaccggtg        120
ctgcttgagg actaccacct cttggagaag ctggctaact ttgaccgtga acggcaaccg        180
gagcgtgttg tacacgcgcg cggtgtgact gccaagggtt actttgaggt gacacacgat        240
atcacagact taacctgcgc ggacatgttc gcggaggttg tcgccgtac gccggtggct         300 gtccggtttt cgacggtcat tcactcgcgt cattcaccgg aaaccttgcg tgatccgcgc        360
ggttttgctg tcaagttcta cactcgtgaa ggaatctggg acctcgtcgg aaataatctg        420
ccggtcttct ttatcaggga tgcgatcaag ttcccggact taattcacgc gttcaaacca        480
aacccgcgga cagaggcgca ggaatcctgg aggattctcg acttttttaag caaccaacac       540 gaaagcctga atatgctcac gttccttttc gacgacgagg gtatcccgaa ggactatcgg        600
catatgcgcg gcagcggagt gcactcgttc cgccttgtaa ccagggacgg acgctcgacg        660
tacgtgcgct tccactggcg ccccaagtgc ggtatggaaa acttgttgga cgaagaggct        720
gccgttgtgt gtggtcagga ttttttctcac gcaacgcatg acttgatccg ggcaattgac      780
cgaggcgact atcccgaatg ggcgctctat atccaaacca tggacccggc aatggttgag        840
aaccacgtgt tcccgtgggg cgatccactc gacgcgacga gagagtggcc tgagaaggac       900
tttccgcttc gccctgtggg tcgcatggtg ctgaatcaga actgcgataa ccagttcttg        960
gagaatgagc aaattgcctt ctcgccggca ctcgttgtcc caggtatcta ctattcagac      1020
gataagctgt tgcagggtcg ccttttcagt tacgccgaca cgcagcgata ccgtattggt      1080
gccaattatc tgcagctgcc gatcaacgca ccaaagaatc cgttccataa taaccattat      1140
gatggccagc agaactggat gctgcgtcag ggcgaagtga actactaccc cagccgcgta      1200
gacccggtgc cggaggcgcc cccggccgca ttcccaacgc ctcgcgatga actacgtggt      1260
cagcgggtga agcagctggt tccaaatcag tgcgactttg tgcagcctgg agaacgttac      1320
cgctctttcg atccggcgcg caaggagcgg ttcgtgaacc ggatcgcgaa actgctaaca      1380
gatgagcgcg tgaccccaga gctgcgagcc atctggctgg agctctggag caaatgcgat     1440
gctgaactgg gcgcagcgct ggcgaccaga gtgaagcagt gtacaatg                  1488
```

```
<210> SEQ ID NO 18
<211> LENGTH: 496
<212> TYPE: PRT
<213> ORGANISM: Cyanidioschyzon merolae

<400> SEQUENCE: 18

Met Asp Pro Thr Lys Tyr Thr Pro Arg Asp Thr Phe Asp Val Asn Val
1               5                   10                  15

Leu Thr Thr Asn Ala Gly Gln Pro Val Thr Asn Asn Gln Ser Ser Arg
                20                  25                  30

Thr Val Gly Pro Arg Gly Pro Val Leu Leu Glu Asp Tyr His Leu Leu
                35                  40                  45

Glu Lys Leu Ala Asn Phe Asp Arg Glu Arg Gln Pro Glu Arg Val Val
        50                  55                  60

His Ala Arg Gly Val Thr Ala Lys Gly Tyr Phe Glu Val Thr His Asp
65                  70                  75                  80

Ile Thr Asp Leu Thr Cys Ala Asp Met Phe Ala Glu Val Gly Arg Arg
                85                  90                  95

Thr Pro Val Ala Val Arg Phe Ser Thr Val Ile His Ser Arg His Ser
            100                 105                 110

Pro Glu Thr Leu Arg Asp Pro Arg Gly Phe Ala Val Lys Phe Tyr Thr
```

```
              115                 120                 125
Arg Glu Gly Ile Trp Asp Leu Val Gly Asn Asn Leu Pro Val Phe Phe
    130                 135                 140

Ile Arg Asp Ala Ile Lys Phe Pro Asp Leu Ile His Ala Phe Lys Pro
145                 150                 155                 160

Asn Pro Arg Thr Glu Ala Gln Glu Ser Trp Arg Ile Leu Asp Phe Leu
                165                 170                 175

Ser Asn Gln His Glu Ser Leu Asn Met Leu Thr Phe Leu Phe Asp Asp
                180                 185                 190

Glu Gly Ile Pro Lys Asp Tyr Arg His Met Arg Gly Ser Gly Val His
                195                 200                 205

Ser Phe Arg Leu Val Thr Arg Asp Gly Arg Ser Thr Tyr Val Arg Phe
    210                 215                 220

His Trp Arg Pro Lys Cys Gly Met Glu Asn Leu Leu Asp Glu Glu Ala
225                 230                 235                 240

Ala Val Val Cys Gly Gln Asp Phe Ser His Ala Thr His Asp Leu Ile
                245                 250                 255

Arg Ala Ile Asp Arg Gly Asp Tyr Pro Glu Trp Ala Leu Tyr Ile Gln
                260                 265                 270

Thr Met Asp Pro Ala Met Val Glu Asn His Val Phe Pro Trp Gly Asp
                275                 280                 285

Pro Leu Asp Ala Thr Arg Glu Trp Pro Glu Lys Asp Phe Pro Leu Arg
    290                 295                 300

Pro Val Gly Arg Met Val Leu Asn Gln Asn Cys Asp Asn Gln Phe Leu
305                 310                 315                 320

Glu Asn Glu Gln Ile Ala Phe Ser Pro Ala Leu Val Val Pro Gly Ile
                325                 330                 335

Tyr Tyr Ser Asp Asp Lys Leu Leu Gln Gly Arg Leu Phe Ser Tyr Ala
                340                 345                 350

Asp Thr Gln Arg Tyr Arg Ile Gly Ala Asn Tyr Leu Gln Leu Pro Ile
                355                 360                 365

Asn Ala Pro Lys Asn Pro Phe His Asn Asn His Tyr Asp Gly Gln Gln
    370                 375                 380

Asn Trp Met Leu Arg Gln Gly Glu Val Asn Tyr Tyr Pro Ser Arg Val
385                 390                 395                 400

Asp Pro Val Pro Glu Ala Pro Ala Ala Phe Pro Thr Pro Arg Asp
                405                 410                 415

Glu Leu Arg Gly Gln Arg Val Lys Gln Leu Val Pro Asn Gln Cys Asp
                420                 425                 430

Phe Val Gln Pro Gly Glu Arg Tyr Arg Ser Phe Asp Pro Ala Arg Lys
                435                 440                 445

Glu Arg Phe Val Asn Arg Ile Ala Lys Leu Leu Thr Asp Glu Arg Val
    450                 455                 460

Thr Pro Glu Leu Arg Ala Ile Trp Leu Glu Leu Trp Ser Lys Cys Asp
465                 470                 475                 480

Ala Glu Leu Gly Ala Ala Leu Ala Thr Arg Val Lys Gln Cys Thr Met
                485                 490                 495
```

<210> SEQ ID NO 19
<211> LENGTH: 8157
<212> TYPE: DNA
<213> ORGANISM: Cyanidioschyzon merolae

<400> SEQUENCE: 19

-continued

```
atgggggatt tgggtgaaca tgcaccgtcg aatggctccg caaaggatag cgttcggcgc        60
tatgttgagg aacacggcgg tagtagacca attcagcgct tattggtcgc aaacaacgga       120
atcgccgccg taaagtgcat ccgatcaatg cgaagatggg catacgaagc gtttggtagt       180
gaacgagcgc tggagtttgt agcaatggcc actcccgagg atgttcaagc caacgccgac       240
tacattcgcc tcgctgacct cttcgttccc gtacctgggg gaagcaacaa ccacaactac       300
gccaacgtgg agctcatcgt cgacatcgcg gaaaggaacg agtgcgatgc agtatgggcg       360
ggttggggtc acgccagcga gaacccgctg ctgcccgctc gccttgcgga gactggtatc       420
gcattcctgg gaccggatgc cattgccatg agggcgctcg gcgacaagat ttcgtcaacg       480
ttgttagctc agtctgcgga tgttccagtc gtcagctgga acggtgatga cttgaaggta       540
acttttcacc gcgagcgcgg cggtattgat gaagaacgct atcgccgtgc ctgcgttgcg       600
aatgtcgacg aggctcgcgc tgctgccgat cgtattggct acccagtgat gattaaagcc       660
agcgaaggag gcggtggcaa aggcatccgt ctttgccgtc gaccagagga tgttcgagat       720
gcctttcgtc aggtcgccgg agagattcct ggctctccga tcttcatcat gaaaatggtg       780
gatcaagcgc gacacctgga agtgcagatt gttgccgatg aatacgggca cgcgatagcg       840
ctatatgggc gtgactgctc cgtgcagaga cggcatcaaa agatcatcga ggaagggcca       900
gttacggcaa cgccaccgca ggtttggaaa gagctcgaac atggagcggt gcgtcttgcc       960
aaaatggtcg gttacgtagg tgccggcact gttgagtatc tctacgacgg tcgacgtttc      1020
tatttcctgg aactgaatcc gcgcttgcag gtggagcacc cagtaaccga gtggatcact      1080
ggcgtgaacc tgcctgcagt ccagctgcag attgccatgg ggattccgct ccagcgtatt      1140
gcagctatcc aagcacttta cggcaataga ccggacctgg atctcgagcg acaccagccg      1200
aacccgccgc atggccacgt aatcgcctgc cgcgttaccg cagaaaatcc cgaggaagga      1260
ttccagccga caagcggctc cattcaggag ctttcgtttc gaaatacgcc caatgtgtgg      1320
ggctatttca gcgtcggcgc ctggggtggt gtccacgagt acgctgactc gcaattcggg      1380 caccttttg cctggggtgc ggatcgcgag atggcccgga ggaatatggt gctggcactg      1440
aaagagctca gcatccgcgg agatatccgc acaacggtgg agtatcttat tacgttgctg      1500
gagctcgaat cgtatcgcga aaatcgcatc cataccgtt ggctggacaa cctcattgcc      1560
tccaaagtga aaccagagcg accgccgttc catatcgctg ttgtgcttgg tgcagtccat      1620
caggcgtaca gagcctggtc tgagcgccgg cgatctttg ttgagtcgct gagtcgcggt      1680
caagtgccgc agcgtattga cgctaccttc atagaatttc agttcgagct gatctacgat      1740
gagctcaagt acgcgctcat cgtcaggcaa gcgggtccga atgccttcca cgtctcccta      1800
gcacagcatc ccgaggaacg ggtgcgtgtt gatttccgac ctctgctgga cggtggtctc      1860
ttgatcatgt gcgatggtcg ctccttcaat actcactcca aggaggattc cactggcatg      1920
cgtctgagca tcgacgggcg aacctgtgtg ttcccaggcg aaatggaccc tacgcgcatt      1980
gcagcacagg cctcggggcg tctcgtccga tacctggttg ccaacgagga acacgtcgat      2040
cagggacaag tcattgcgga gattgaagtc atgaaaatgt atctgagcgt gcaggctccc      2100
gaaccgggca ccattcactt gctgaaacca gcgggagcgg ccctggagcc aggcgaagtt      2160
tttgcgcagc tcgatctcga cgatccgagc aaagttcgac gggtgacgcc atttactggg      2220
cgctttccga caatgctgcc tccacagcga ctgggaaaga aaccgcacca gcgctttgag      2280
agcgcgaaac agcagatcga agcgctcctg gacggctacg atgttgatat ggagccgctc      2340
ggcatgcttc tgcagctggc gagcaccgaa ccggcagtac cggccgggaa actgcaggag      2400
```

-continued

```
gcgctctctt tcctagccgg tcgtattccg tcgacgttgc atgccgccct tctaggacaa    2460
gttttcgaac tgcgttccgt tgctcgtgat gatcacgagc gcctccaaca gcatttccgc    2520
gaaatgaagc gcatgatcag cgatttctgc gagcaacttg ccatcgcagc ggaccgcgag    2580
gcgctggagg ctaccctgcg cccctgacc agtatcctgg aggcgtatgt tcgcgggggc    2640
cttcgcggct accacgagca tctcgttgta tgcctcatgc aacgctatgt gaatacggag    2700
aagtattttg cgcaaggtcg gcggctcgat gaggttctat tcgatctgcg cgaacaacac    2760
cgcgagcact tggaagttgt tgcggatatc atgctcgcac atgcccagtt agcgcgaaag    2820
aaccaactga tgctcgcttt gctcgatcac atagccgcgg atgcatcgct tctgcgcagt    2880
gtcattgtcc ggcagtgcct tcacgaggtg gctgcgttca tccaccccga ctatagccaa    2940
ctggcgctgc gagcaagact cttgctggcg agttctcgtc gccgagcgct ccccgaacgt    3000
cgagagcgcc tctgcaagca gatcgaacag gctgtacatg cgcccactga agaacaatgc    3060
tatcgtctgt tgcacgcggt ggtcgagtcc caggaaagca tcctggatgc gctggtgagc    3120
ctaaccatga acccgggggt gccggtggag attcgcaaag ccgctgtcca gtgccagatc    3180
ctgcgggcct acaaagcgta ccacgtgtac gatctggttg tcgaacttga cgaggaactg    3240
ggtttcctgc gggcgttgtg gcgtttccag tatcgttcaa acctgaacgc ttttggtagt    3300
cattccagta tgcggtcgtt tccggcggca ttggtggcgg cgtcggctcc gctagcccgc    3360
cggcagctgc gtagctacga ctctgcggac aatttgcaga actggggctt tcgagtcggt    3420
atgttggtcg tctttgagac gctgcgggcg atggtgcagg gtttcgatcg tgtgctccag    3480
gtttttcgag cggaaaccgg cggcgaaacg ctggcttcgc ctcgtaccaa gtcgagcgcc    3540
gcagtcgatt ccagtgcaga ctccagtgct gaaggtattg gtgtcaatgt actgaccatc    3600
gccattccct ggacggccgt ggaggtcgct gattttgcga aatacctggg cgttgcagac    3660
gcggacgacc gtctgcaggc aagtaatgcg aacgactcgg agcaggttgt cgccctgctc    3720
acgcgtttct gtcgctcttc cgcggagcgc aaagcctcga tgcgcgctgc cggtatcaaa    3780
cttgtgacct ttttggtggc acccggtgaa ctgtgccagc gcacgctggg ctccagtctg    3840
cctcgtgaaa gcacttatcc gggtttctat acgttgcggg catcgctcga gtacgccgag    3900
gatcccattt atcgccacat tgatccacca gcggctttcc agctggagct gaatcgattg    3960
gcgaactttc gtatcacccg ctttgaacat ccgaaccgct ccattcacgt cttctacgcg    4020
gaagatcgaa ccgacaaggg cgacgctcgc ttcttcgtgc gcgcttttgt acggcaagcg    4080
gaagtctacg ccagtcccag cgatacagca gcggtttcga tcccggaagc ggagaggact    4140
tttgtggcct gtctggatgc cttggaaacc gcccgttgtg ataggcgctt ccgacgaacg    4200
gactttaatc atctcttctt gcacctgatt ccccgggtct ccatcgatgt ggatgacgtc    4260
gaggcgatct gtacgcgcct cttttatcgg ttctcctcac gttgctggcg tttgcgcgtg    4320
ttcatggtag agatcaaagt ccatgtggaa aaaatgggcc cgaaaccgct tcgatttatt    4380
ctctataatc caaccggaca ctcgttacgc gttgaaggct acgtggaaca gggagatcgt    4440
ctcctgtcgt tggattccag cgatccgggt catttacatg gtacaccgt cgatgagccg    4500 taccaggtac tgaaccgtat ccagcgccgg cgagttgttg cccagacgct cgaaacaact    4560
tacgtctacg attaccagga gctttcacc aaagcactcc atgagcagtg cggcgttat    4620 tcgcaggaac gacttttggg aggatttcgc cgccacaaga taccgctgaa actgctgacc    4680
tgcacggagc tcgttctcca ggatgaagat catgacgaga gcgagctgat agagaccaac    4740
```

-continued

```
cgccccgccg gggagaatga aatcggtatg gtcgcctggc gctacacctt cttcacgccc   4800
gagtatcccc agggtcgcga tgcgatcgtc attgccaacg atatcacgta cctgagtgga   4860
tcgtttggac ctcgagagga tcgcctcttt gccaaggcgt ctcagcaggc gagaaagctc   4920
ggtataccgc gcatctacat cgctgcgaat agcggagccc gaatcggcct cgcggaagaa   4980
ctgcgcaacg tcttccaagt tcagtggaag gatgcacatg acccgagccg aggcttcgac   5040
tacctctacc tgggactggc ggataagctc aagtacgagg atgaactcgg catcgtgcga   5100
acgcgagacg tcggcggcgg caagtacgct ctagttgata tctatggcgc tgaggatggc   5160
attggtgtcg agaacctcat gggttcagcg tgcatcgctg ccgagacctc agccgcctac   5220
aatgactgct tcaccatcac gtacgtcgca gcgcgctgtg tggggatcgg tgcgtacctc   5280
gtgcgcctgg ggcagcgcgt tatccagcgc gagcacaatg caccgatcat cctcactggc   5340
tactcagcgc tgaataagct tctgggtcgc gaagtctaca ccagccacga acagctgggc   5400
ggtacgaaga tcatgtatcc gaacggggtt acccatctgc gcgtatccaa tgactacgag   5460
ggtgttcggg caattctgga ctggctcgct tttgtgcctc gtatgcaagg ggaacgacct   5520
ccgatgatcg actccatcga tgctgtggta cgcgaagtcg actacgatcc acgagtggct   5580
aacgaggata ttcgatacgc cattgaaggc aagtgggtcg gacccttcgc tcccgacggg   5640
gcaagtgtgg tctcgtcgtc gggctcgtcg gtgtcgtcca atggtccggt tgcgacaggt   5700
gcgagcgctg gactgccgcc cgtcaacatg gagagtgtcg gcggtgaagt tcggtatcgt   5760
tcgcggtcgc ggacggcttc gtatgcgggt gcgaatgcag caacagcagc agcaccagga   5820
gcaagtagct tggcgacctc tggagcggca cttgcgaatg ctacgggacg agcagcggct   5880
cgggtgagcc tcgtatcgac caagcctgca accggtgtcg aggaggttcc cgcggcgttg   5940
ccttcgggtt cgagttcact ggcgctccgc tcgaccgctg tcgctgcgcc tgtacctcag   6000
gagagagcaa agacggatgc ggatgcggat gcggatgcgg atgcggatgc cttggaggcc   6060
actggaactg cccgaggcgc agataccagc ggtgctgggg cgcacgcaag ccctgacacc   6120
cggcagccgc ccacactgga tgccctgaag actgcgaggt ttgcaccagc gcccgctgca   6180
ttgccgacga caggtttacg ctcgccacca cagtccccgg gttctgtttc tgcgtatagc   6240
ccgttggaga gtggctctcc attggagccg tcccttgacg aggatcacat cgctttcacg   6300
gacaccgatc ggatgcggat cgggtcgcct ttggtacacg cgaccgacgc ctgggatacg   6360
agcaacagcg ttcactcgag tagcgcgacg acgatggctg caggtgccgt ccggggctcg   6420
cgactgttca ctgcgtcatc gagtacgtcg gcggctgcgg gagcaagcgc cagcaatagc   6480
agcaacaacg gtagcagcaa tgcgaatacg aataccatga acaatgctgg gagtagcgtg   6540
gcatcggcag gcgcaccgct caacaccacc ggtagcatca ataccaatac caatgccaat   6600
gccaatacca acaatatctt gggtagcggt ggtgttggtg cgacagcttc gctgaccgct   6660
tggagcggta accttccgcc gctaccgtac gttccaaata cgctcatggt ggtggacaac   6720
caagggtacg tgttcctggc aggcctcttc gaccgtcact cgtttcgaga gacgctcgct   6780
ggctgggcga gtccgttgt ggttggtaga gcacgccttg gtggtatccc cgtgggcgtt   6840
attgcgacac agacggtgac cacagagaag gttattcccc cggatccagc ggcgccagac   6900
tcgcgtgagc ttcgtgaaca gcaggccggt caagtctggt atccagattc atccttcaag   6960
actgcccaaa gtattcgtga ttttgatcgc gagggtttgc ctctgtttgt tctggccagc   7020
tggcgcggtt tctctggcgg agcacacgac atgttccagg aaatactcaa gtttggttca   7080
gagatcgttg acgcgcttcg cgagtactcg aaaccgtct ttgtgtacat accaccggga   7140
```

-continued

```
ggcgagcttc gaggcggtgc ctgggtcgtc ctcgataccg ccatcaatcc ccgctttatc        7200
gaaatgtacg ccgatgaaag tgcacgtggt ggtgtgctcg aacctgccgg taccgtggat        7260
atcaagttcc gcaccagaga tttgctgaag accatgcagc gcctgctacc atcgtctaga        7320
cgtgatgaga gcgattcgag tgcgtccgac gttgtcggca tgctgtcttt ggacgcatca        7380
tcatcatcag cagcagcaac agcagcaaca acaacaacaa caacaacaac aacaacaaca        7440
gcaggtaccg ctgggacgtc ctcttcgact gctgggcgta gcgagtcgcg ggtcacaaag        7500
tcaacggcgg acggcttgcc agccttcgag gcagacggtc ggagttcgct cgagcaaaca        7560
ctcttgccca tctttcagca gatagccatg acgtttgcgg atctgcacga tacagcgggt        7620
cggatgcaac ataagcgcgc gattcgccga gtggtaccct ggcgaacaag tcgcacgttt        7680
ttctactggc gccttcgacg tcggctcgcc gaggaggaac tgcggagtcg cgtttcacaa        7740
gcggatccgc aactcagcga cgcggagatc gatgcgctgc tgcggaaatg ggcaagagca        7800
catgaccccg ctctggacgg tgatatttac gaacttgatg atcctcgtgt cgtgcaatgg        7860
ctcgaggacg aattggatag ccagttggag cggcgtttgc acaaactccg cgaagcacgc        7920
gccacctggc aagctgtgga actggggaat acagcacccg aggcgttgct tgcggcaatt        7980
gagcgtattc tcgtacaaat ggatgaagtt ggtcgcaacg aatggttacg aacgcttagt        8040
gcgcgactcg agaacacctc atccggtttg ggtgatctcg aggcgcccag ctcgggtgag        8100
caggccgcac cacgacgtgt cttgtcgggt cgtggtctgc tgcgacgctt cctcggg          8157
```

```
<210> SEQ ID NO 20
<211> LENGTH: 2719
<212> TYPE: PRT
<213> ORGANISM: Cyanidioschyzon merolae

<400> SEQUENCE: 20

Met Gly Asp Leu Gly Glu His Ala Pro Ser Asn Gly Ser Ala Lys Asp
1               5                   10                  15

Ser Val Arg Arg Tyr Val Glu Glu His Gly Gly Ser Arg Pro Ile Gln
                20                  25                  30

Arg Leu Leu Val Ala Asn Asn Gly Ile Ala Ala Val Lys Cys Ile Arg
            35                  40                  45

Ser Met Arg Arg Trp Ala Tyr Glu Ala Phe Gly Ser Glu Arg Ala Leu
        50                  55                  60

Glu Phe Val Ala Met Ala Thr Pro Glu Asp Val Gln Ala Asn Ala Asp
65                  70                  75                  80

Tyr Ile Arg Leu Ala Asp Leu Phe Val Pro Val Pro Gly Gly Ser Asn
                85                  90                  95

Asn His Asn Tyr Ala Asn Val Glu Leu Ile Val Asp Ile Ala Glu Arg
            100                 105                 110

Asn Glu Cys Asp Ala Val Trp Ala Gly Trp Gly His Ala Ser Glu Asn
        115                 120                 125

Pro Leu Leu Pro Ala Arg Leu Ala Glu Thr Gly Ile Ala Phe Leu Gly
        130                 135                 140

Pro Asp Ala Ile Ala Met Arg Ala Leu Gly Asp Lys Ile Ser Ser Thr
145                 150                 155                 160

Leu Leu Ala Gln Ser Ala Asp Val Pro Val Val Ser Trp Asn Gly Asp
                165                 170                 175

Asp Leu Lys Val Thr Phe His Arg Glu Arg Gly Gly Ile Asp Glu Glu
                180                 185                 190
```

-continued

```
Arg Tyr Arg Arg Ala Cys Val Ala Asn Val Asp Glu Ala Arg Ala Ala
        195                 200                 205

Ala Asp Arg Ile Gly Tyr Pro Val Met Ile Lys Ala Ser Glu Gly Gly
    210                 215                 220

Gly Gly Lys Gly Ile Arg Leu Cys Arg Arg Pro Glu Asp Val Arg Asp
225                 230                 235                 240

Ala Phe Arg Gln Val Ala Gly Glu Ile Pro Gly Ser Pro Ile Phe Ile
            245                 250                 255

Met Lys Met Val Asp Gln Ala Arg His Leu Glu Val Gln Ile Val Ala
            260                 265                 270

Asp Glu Tyr Gly His Ala Ile Ala Leu Tyr Gly Arg Asp Cys Ser Val
        275                 280                 285

Gln Arg Arg His Gln Lys Ile Ile Glu Glu Gly Pro Val Thr Ala Thr
    290                 295                 300

Pro Pro Gln Val Trp Lys Glu Leu Glu His Gly Ala Val Arg Leu Ala
305                 310                 315                 320

Lys Met Val Gly Tyr Val Gly Ala Gly Thr Val Glu Tyr Leu Tyr Asp
                325                 330                 335

Gly Arg Arg Phe Tyr Phe Leu Glu Leu Asn Pro Arg Leu Gln Val Glu
            340                 345                 350

His Pro Val Thr Glu Trp Ile Thr Gly Val Asn Leu Pro Ala Val Gln
        355                 360                 365

Leu Gln Ile Ala Met Gly Ile Pro Leu Gln Arg Ile Ala Ala Ile Gln
    370                 375                 380

Ala Leu Tyr Gly Asn Arg Pro Asp Leu Asp Leu Glu Arg His Gln Pro
385                 390                 395                 400

Asn Pro Pro His Gly His Val Ile Ala Cys Arg Val Thr Ala Glu Asn
            405                 410                 415

Pro Glu Glu Gly Phe Gln Pro Thr Ser Gly Ser Ile Gln Glu Leu Ser
            420                 425                 430

Phe Arg Asn Thr Pro Asn Val Trp Gly Tyr Phe Ser Val Gly Ala Trp
    435                 440                 445

Gly Gly Val His Glu Tyr Ala Asp Ser Gln Phe Gly His Leu Phe Ala
    450                 455                 460

Trp Gly Ala Asp Arg Glu Met Ala Arg Arg Asn Met Val Leu Ala Leu
465                 470                 475                 480

Lys Glu Leu Ser Ile Arg Gly Asp Ile Arg Thr Thr Val Glu Tyr Leu
                485                 490                 495

Ile Thr Leu Leu Glu Leu Glu Ser Tyr Arg Glu Asn Arg Ile His Thr
            500                 505                 510

Arg Trp Leu Asp Asn Leu Ile Ala Ser Lys Val Lys Pro Glu Arg Pro
        515                 520                 525

Pro Phe His Ile Ala Val Val Leu Gly Ala Val His Gln Ala Tyr Arg
    530                 535                 540

Ala Trp Ser Glu Arg Arg Arg Ser Phe Val Glu Ser Leu Ser Arg Gly
545                 550                 555                 560

Gln Val Pro Gln Arg Ile Asp Ala Thr Phe Ile Glu Phe Gln Phe Glu
            565                 570                 575

Leu Ile Tyr Asp Glu Leu Lys Tyr Ala Leu Ile Val Arg Gln Ala Gly
            580                 585                 590

Pro Asn Ala Phe His Val Ser Leu Ala Gln His Pro Glu Glu Arg Val
        595                 600                 605

Arg Val Asp Phe Arg Pro Leu Leu Asp Gly Gly Leu Leu Ile Met Cys
```

```
           610               615               620

Asp Gly Arg Ser Phe Asn Thr His Ser Lys Glu Asp Ser Thr Gly Met
625               630               635               640

Arg Leu Ser Ile Asp Gly Arg Thr Cys Val Phe Pro Gly Glu Met Asp
              645               650               655

Pro Thr Arg Ile Ala Ala Gln Ala Ser Gly Arg Leu Val Arg Tyr Leu
              660               665               670

Val Ala Asn Glu Glu His Val Asp Gln Gly Gln Val Ile Ala Glu Ile
              675               680               685

Glu Val Met Lys Met Tyr Leu Ser Val Gln Ala Pro Glu Pro Gly Thr
690               695               700

Ile His Leu Leu Lys Pro Ala Gly Ala Ala Leu Glu Pro Gly Glu Val
705               710               715               720

Phe Ala Gln Leu Asp Leu Asp Asp Pro Ser Lys Val Arg Arg Val Thr
              725               730               735

Pro Phe Thr Gly Arg Phe Pro Thr Met Leu Pro Pro Gln Arg Leu Gly
              740               745               750

Lys Lys Pro His Gln Arg Phe Glu Ser Ala Lys Gln Gln Ile Glu Ala
              755               760               765

Leu Leu Asp Gly Tyr Asp Val Asp Met Glu Pro Leu Gly Met Leu Leu
              770               775               780

Gln Leu Ala Ser Thr Glu Pro Ala Val Pro Ala Gly Lys Leu Gln Glu
785               790               795               800

Ala Leu Ser Phe Leu Ala Gly Arg Ile Pro Ser Thr Leu His Ala Ala
              805               810               815

Leu Leu Gly Gln Val Phe Glu Leu Arg Ser Val Ala Arg Asp Asp His
              820               825               830

Glu Arg Leu Gln Gln His Phe Arg Glu Met Lys Arg Met Ile Ser Asp
              835               840               845

Phe Cys Glu Gln Leu Ala Ile Ala Ala Asp Arg Glu Ala Leu Glu Ala
850               855               860

Thr Leu Arg Pro Leu Thr Ser Ile Leu Glu Ala Tyr Val Arg Gly Gly
865               870               875               880

Leu Arg Gly Tyr His Glu His Leu Val Val Cys Leu Met Gln Arg Tyr
              885               890               895

Val Asn Thr Glu Lys Tyr Phe Ala Gln Gly Arg Arg Leu Asp Glu Val
              900               905               910

Leu Phe Asp Leu Arg Glu Gln His Arg Glu His Leu Glu Val Val Ala
              915               920               925

Asp Ile Met Leu Ala His Ala Gln Leu Ala Arg Lys Asn Gln Leu Met
              930               935               940

Leu Ala Leu Leu Asp His Ile Ala Ala Asp Ala Ser Leu Leu Arg Ser
945               950               955               960

Val Ile Val Arg Gln Cys Leu His Glu Val Ala Ala Phe Ile His Pro
              965               970               975

Asp Tyr Ser Gln Leu Ala Leu Arg Ala Arg Leu Leu Leu Ala Ser Ser
              980               985               990

Arg Arg Arg Ala Leu Pro Glu Arg  Arg Glu Arg Leu Cys  Lys Gln Ile
              995               1000               1005

Glu Gln  Ala Val His Ala Pro  Thr Glu Glu Gln Cys  Tyr Arg Leu
              1010               1015               1020

Leu His  Ala Val Val Glu Ser  Gln Glu Ser Ile Leu  Asp Ala Leu
              1025               1030               1035
```

-continued

```
Val Ser  Leu Thr Met Asn Pro  Gly Val Pro Val Glu  Ile Arg Lys
    1040                 1045              1050

Ala Ala  Val Gln Cys Gln Ile  Leu Arg Ala Tyr Lys  Ala Tyr His
    1055                 1060              1065

Val Tyr  Asp Leu Val Val Glu  Leu Asp Glu Glu Leu  Gly Phe Leu
    1070                 1075              1080

Arg Ala  Leu Trp Arg Phe Gln  Tyr Arg Ser Asn Leu  Asn Ala Phe
    1085                 1090              1095

Gly Ser  His Ser Ser Met Arg  Ser Phe Pro Ala Ala  Leu Val Ala
    1100                 1105              1110

Ala Ser  Ala Pro Leu Ala Arg  Arg Gln Leu Arg Ser  Tyr Asp Ser
    1115                 1120              1125

Ala Asp  Asn Leu Gln Asn Trp  Gly Phe Arg Val Gly  Met Leu Val
    1130                 1135              1140

Val Phe  Glu Thr Leu Arg Ala  Met Val Gln Gly Phe  Asp Arg Val
    1145                 1150              1155

Leu Gln  Val Phe Arg Ala Glu  Thr Gly Gly Glu Thr  Leu Ala Ser
    1160                 1165              1170

Pro Arg  Thr Lys Ser Ser Ala  Ala Val Asp Ser Ser  Ala Asp Ser
    1175                 1180              1185

Ser Ala  Glu Gly Ile Gly Val  Asn Val Leu Thr Ile  Ala Ile Pro
    1190                 1195              1200

Trp Thr  Ala Val Glu Val Ala  Asp Phe Ala Lys Tyr  Leu Gly Val
    1205                 1210              1215

Ala Asp  Ala Asp Asp Arg Leu  Gln Ala Ser Asn Ala  Asn Asp Ser
    1220                 1225              1230

Glu Gln  Val Val Ala Leu Leu  Thr Arg Phe Cys Arg  Ser Ser Ala
    1235                 1240              1245

Glu Arg  Lys Ala Ser Met Arg  Ala Ala Gly Ile Lys  Leu Val Thr
    1250                 1255              1260

Phe Leu  Val Ala Pro Gly Glu  Leu Cys Gln Arg Thr  Leu Gly Ser
    1265                 1270              1275

Ser Leu  Pro Arg Glu Ser Thr  Tyr Pro Gly Phe Tyr  Thr Leu Arg
    1280                 1285              1290

Ala Ser  Leu Glu Tyr Ala Glu  Asp Pro Ile Tyr Arg  His Ile Asp
    1295                 1300              1305

Pro Pro  Ala Ala Phe Gln Leu  Glu Leu Asn Arg Leu  Ala Asn Phe
    1310                 1315              1320

Arg Ile  Thr Arg Phe Glu His  Pro Asn Arg Ser Ile  His Val Phe
    1325                 1330              1335

Tyr Ala  Glu Asp Arg Thr Asp  Lys Gly Asp Ala Arg  Phe Phe Val
    1340                 1345              1350

Arg Ala  Phe Val Arg Gln Ala  Glu Val Tyr Ala Ser  Pro Ser Asp
    1355                 1360              1365

Thr Ala  Ala Val Ser Ile Pro  Glu Ala Glu Arg Thr  Phe Val Ala
    1370                 1375              1380

Cys Leu  Asp Ala Leu Glu Thr  Ala Arg Cys Asp Arg  Arg Phe Arg
    1385                 1390              1395

Arg Thr  Asp Phe Asn His Leu  Phe Leu His Leu Ile  Pro Arg Val
    1400                 1405              1410

Ser Ile  Asp Val Asp Asp Val  Glu Ala Ile Cys Thr  Arg Leu Phe
    1415                 1420              1425
```

```
Tyr Arg Phe Ser Ser Arg Cys Trp Arg Leu Arg Val Phe Met Val
    1430            1435            1440

Glu Ile Lys Val His Val Glu Lys Met Gly Pro Lys Pro Leu Arg
    1445            1450            1455

Phe Ile Leu Tyr Asn Pro Thr Gly His Ser Leu Arg Val Glu Gly
    1460            1465            1470

Tyr Val Glu Gln Gly Asp Arg Leu Leu Ser Leu Asp Ser Ser Asp
    1475            1480            1485

Pro Gly His Leu His Gly Thr Pro Val Asp Glu Pro Tyr Gln Val
    1490            1495            1500

Leu Asn Arg Ile Gln Arg Arg Arg Val Val Ala Gln Thr Leu Glu
    1505            1510            1515

Thr Thr Tyr Val Tyr Asp Tyr Gln Glu Leu Phe Thr Lys Ala Leu
    1520            1525            1530

His Glu Gln Trp Arg Arg Tyr Ser Gln Glu Arg Leu Leu Gly Gly
    1535            1540            1545

Phe Arg Arg His Lys Ile Pro Leu Lys Leu Leu Thr Cys Thr Glu
    1550            1555            1560

Leu Val Leu Gln Asp Glu Asp His Asp Glu Ser Glu Leu Ile Glu
    1565            1570            1575

Thr Asn Arg Pro Ala Gly Glu Asn Glu Ile Gly Met Val Ala Trp
    1580            1585            1590

Arg Tyr Thr Phe Phe Thr Pro Glu Tyr Pro Gln Gly Arg Asp Ala
    1595            1600            1605

Ile Val Ile Ala Asn Asp Ile Thr Tyr Leu Ser Gly Ser Phe Gly
    1610            1615            1620

Pro Arg Glu Asp Arg Leu Phe Ala Lys Ala Ser Gln Gln Ala Arg
    1625            1630            1635

Lys Leu Gly Ile Pro Arg Ile Tyr Ile Ala Ala Asn Ser Gly Ala
    1640            1645            1650

Arg Ile Gly Leu Ala Glu Glu Leu Arg Asn Val Phe Gln Val Gln
    1655            1660            1665

Trp Lys Asp Ala His Asp Pro Ser Arg Gly Phe Asp Tyr Leu Tyr
    1670            1675            1680

Leu Gly Leu Ala Asp Lys Leu Lys Tyr Glu Asp Glu Leu Gly Ile
    1685            1690            1695

Val Arg Thr Arg Asp Val Gly Gly Gly Lys Tyr Ala Leu Val Asp
    1700            1705            1710

Ile Tyr Gly Ala Glu Asp Gly Ile Gly Val Glu Asn Leu Met Gly
    1715            1720            1725

Ser Ala Cys Ile Ala Ala Glu Thr Ser Ala Ala Tyr Asn Asp Cys
    1730            1735            1740

Phe Thr Ile Thr Tyr Val Ala Ala Arg Cys Val Gly Ile Gly Ala
    1745            1750            1755

Tyr Leu Val Arg Leu Gly Gln Arg Val Ile Gln Arg Glu His Asn
    1760            1765            1770

Ala Pro Ile Ile Leu Thr Gly Tyr Ser Ala Leu Asn Lys Leu Leu
    1775            1780            1785

Gly Arg Glu Val Tyr Thr Ser His Glu Gln Leu Gly Gly Thr Lys
    1790            1795            1800

Ile Met Tyr Pro Asn Gly Val Thr His Leu Arg Val Ser Asn Asp
    1805            1810            1815

Tyr Glu Gly Val Arg Ala Ile Leu Asp Trp Leu Ala Phe Val Pro
```

-continued

```
         1820              1825              1830

Arg Met Gln Gly Glu Arg Pro  Pro Met Ile Asp Ser  Ile Asp Ala
    1835              1840              1845

Val Val Arg Glu Val Asp Tyr  Asp Pro Arg Val Ala  Asn Glu Asp
    1850              1855              1860

Ile Arg Tyr Ala Ile Glu Gly  Lys Trp Val Gly Pro  Phe Ala Pro
    1865              1870              1875

Asp Gly Ala Ser Val Val Ser  Ser Ser Gly Ser Ser  Val Ser Ser
    1880              1885              1890

Asn Gly Pro Val Ala Thr Gly  Ala Ser Ala Gly Leu  Pro Pro Val
    1895              1900              1905

Asn Met Glu Ser Val Gly Gly  Glu Val Arg Tyr Arg  Ser Arg Ser
    1910              1915              1920

Arg Thr Ala Ser Tyr Ala Gly  Ala Asn Ala Ala Thr  Ala Ala Ala
    1925              1930              1935

Pro Gly Ala Ser Ser Leu Ala  Thr Ser Gly Ala Ala  Leu Ala Asn
    1940              1945              1950

Ala Thr Gly Arg Ala Ala Ala  Arg Val Ser Leu Val  Ser Thr Lys
    1955              1960              1965

Pro Ala Thr Gly Val Glu Glu  Val Pro Ala Ala Leu  Pro Ser Gly
    1970              1975              1980

Ser Ser Ser Leu Ala Leu Arg  Ser Thr Ala Val Ala  Ala Pro Val
    1985              1990              1995

Pro Gln Glu Arg Ala Lys Thr  Asp Ala Asp Ala Asp  Ala Asp Ala
    2000              2005              2010

Asp Ala Asp Ala Leu Glu Ala  Thr Gly Thr Ala Arg  Gly Ala Asp
    2015              2020              2025

Thr Ser Gly Ala Gly Ala His  Ala Ser Pro Asp Thr  Arg Gln Pro
    2030              2035              2040

Pro Thr Leu Asp Ala Leu Lys  Thr Ala Arg Phe Ala  Pro Ala Pro
    2045              2050              2055

Ala Ala Leu Pro Thr Thr Gly  Leu Arg Ser Pro Pro  Gln Ser Pro
    2060              2065              2070

Gly Ser Val Ser Ala Tyr Ser  Pro Leu Glu Ser Gly  Ser Pro Leu
    2075              2080              2085

Glu Pro Ser Leu Asp Glu Asp  His Ile Ala Phe Thr  Asp Thr Asp
    2090              2095              2100

Arg Met Arg Ile Gly Ser Pro  Leu Val His Ala Thr  Asp Ala Trp
    2105              2110              2115

Asp Thr Ser Asn Ser Val His  Ser Ser Ser Ala Thr  Thr Met Ala
    2120              2125              2130

Ala Gly Ala Val Arg Gly Ser  Arg Leu Phe Thr Ala  Ser Ser Ser
    2135              2140              2145

Thr Ser Ala Ala Ala Gly Ala  Ser Ala Ser Asn Ser  Ser Asn Asn
    2150              2155              2160

Gly Ser Ser Asn Ala Asn Thr  Asn Thr Met Asn Asn  Ala Gly Ser
    2165              2170              2175

Ser Val Ala Ser Ala Gly Ala  Pro Leu Asn Thr Thr  Gly Ser Ile
    2180              2185              2190

Asn Thr Asn Thr Asn Ala Asn  Ala Asn Thr Asn Asn  Ile Leu Gly
    2195              2200              2205

Ser Gly Gly Val Gly Ala Thr  Ala Ser Leu Thr Ala  Trp Ser Gly
    2210              2215              2220
```

-continued

```
Asn Leu Pro Pro Leu Pro Tyr  Val Pro Asn Thr Leu  Met Val Val
    2225             2230              2235

Asp Asn Gln Gly Tyr Val Phe  Leu Ala Gly Leu Phe  Asp Arg His
    2240             2245              2250

Ser Phe Arg Glu Thr Leu Ala  Gly Trp Ala Lys Ser  Val Val Val
    2255             2260              2265

Gly Arg Ala Arg Leu Gly Gly  Ile Pro Val Gly Val  Ile Ala Thr
    2270             2275              2280

Gln Thr Val Thr Thr Glu Lys  Val Ile Pro Pro Asp  Pro Ala Ala
    2285             2290              2295

Pro Asp Ser Arg Glu Leu Arg  Glu Gln Gln Ala Gly  Gln Val Trp
    2300             2305              2310

Tyr Pro Asp Ser Ser Phe Lys  Thr Ala Gln Ser Ile  Arg Asp Phe
    2315             2320              2325

Asp Arg Glu Gly Leu Pro Leu  Phe Val Leu Ala Ser  Trp Arg Gly
    2330             2335              2340

Phe Ser Gly Gly Ala His Asp  Met Phe Gln Glu Ile  Leu Lys Phe
    2345             2350              2355

Gly Ser Glu Ile Val Asp Ala  Leu Arg Glu Tyr Ser  Lys Pro Val
    2360             2365              2370

Phe Val Tyr Ile Pro Pro Gly  Gly Glu Leu Arg Gly  Gly Ala Trp
    2375             2380              2385

Val Val Leu Asp Thr Ala Ile  Asn Pro Arg Phe Ile  Glu Met Tyr
    2390             2395              2400

Ala Asp Glu Ser Ala Arg Gly  Gly Val Leu Glu Pro  Ala Gly Thr
    2405             2410              2415

Val Asp Ile Lys Phe Arg Thr  Arg Asp Leu Leu Lys  Thr Met Gln
    2420             2425              2430

Arg Leu Leu Pro Ser Ser Arg  Arg Asp Glu Ser Asp  Ser Ser Ala
    2435             2440              2445

Ser Asp Val Val Gly Met Leu  Ser Leu Asp Ala Ser  Ser Ser Ser
    2450             2455              2460

Ala Ala Ala Thr Ala Ala Thr  Thr Thr Thr Thr Thr  Thr Thr Thr
    2465             2470              2475

Thr Thr Ala Gly Thr Ala Gly  Thr Ser Ser Ser Thr  Ala Gly Arg
    2480             2485              2490

Ser Glu Ser Arg Val Thr Lys  Ser Thr Ala Asp Gly  Leu Pro Ala
    2495             2500              2505

Phe Glu Ala Asp Gly Arg Ser  Ser Leu Glu Gln Thr  Leu Leu Pro
    2510             2515              2520

Ile Phe Gln Gln Ile Ala Met  Thr Phe Ala Asp Leu  His Asp Thr
    2525             2530              2535

Ala Gly Arg Met Gln His Lys  Arg Ala Ile Arg Arg  Val Val Pro
    2540             2545              2550

Trp Arg Thr Ser Arg Thr Phe  Phe Tyr Trp Arg Leu  Arg Arg Arg
    2555             2560              2565

Leu Ala Glu Glu Glu Leu Arg  Ser Arg Val Ser Gln  Ala Asp Pro
    2570             2575              2580

Gln Leu Ser Asp Ala Glu Ile  Asp Ala Leu Leu Arg  Lys Trp Ala
    2585             2590              2595

Arg Ala His Asp Pro Ala Leu  Asp Gly Asp Ile Tyr  Glu Leu Asp
    2600             2605              2610
```

-continued

```
Asp Pro  Arg Val Val Gln Trp  Leu Glu Asp Glu Leu  Asp Ser Gln
    2615                 2620                 2625

Leu Glu  Arg Arg Leu His Lys  Leu Arg Glu Ala Arg  Ala Thr Trp
    2630                 2635                 2640

Gln Ala  Val Glu Leu Gly Asn  Thr Ala Pro Glu Ala  Leu Leu Ala
    2645                 2650                 2655

Ala Ile  Glu Arg Ile Leu Val  Gln Met Asp Glu Val  Gly Arg Asn
    2660                 2665                 2670

Glu Trp  Leu Arg Thr Leu Ser  Ala Arg Leu Glu Asn  Thr Ser Ser
    2675                 2680                 2685

Gly Leu  Gly Asp Leu Glu Ala  Pro Ser Ser Gly Glu  Gln Ala Ala
    2690                 2695                 2700

Pro Arg  Arg Val Leu Ser Gly  Arg Gly Leu Leu Arg  Arg Phe Leu
    2705                 2710                 2715

Gly

<210> SEQ ID NO 21
<211> LENGTH: 1596
<212> TYPE: DNA
<213> ORGANISM: Cyanidioschyzon merolae

<400> SEQUENCE: 21
atgcttctgg cggaaagcct cggcggcgtc gcttttgtca ccgttcacac ggtgctgtgc      60
gtcgctgtac tgtacttacc gtggaaccgc ggcgaccgag aaagcttccg tgtcacttgt     120
ctaggggctt tgagcacttg cgctgttatc gctctgagcc tggtgaatct tcagttgttc     180
ttcactggct tgacctggcg ggagctgtcg cggacgtatc actggctgag gccgtggcac     240
agctggcaag tctatctact ggactctggc ggtttttttgg tgctcctttt tctgcacgag     300
tacagaaaaa gacagcagac tccagttaag agttcgtcat cgagcacgtg tgcatcgacg     360
tcgcagtccg cttgcccgaa tgcggagaac ggcatctatc gaaacgagag gcgaaatacc     420
tggtgcatgt tccgaagcct gctgatcgca ccgataacag aggagctcct cttccgttgt     480
gtattcgatg cagcaatgag atcagctcaa gtccctgaac ttgccagcat gattttcaac     540
ggagtcatgt ttgccgtagc gcacgcgcat cactatttcc ggcaccagag caggtcactt     600
ctcggaaagc agcttcttgt aacgtttttgc tttggttgcg tccaagtcgt ttgcctgaga     660
cggacggatt actccctgtg ggcctgcatc gcaacgcacg ctttggcgaa cgcgctcgat     720
ctgcagaaag ttttcagtga taggggagcg tcacatttttc tctacggcga cgtaggccat     780
cagttaggag ccctgctgca agctgcagca ccgctcgtat tcatcttgcg ctatgcgctt     840
gacatggcca tgcaagcgag tccgttccgg tcctcgatcc tccaggtgca tgcggacccg     900
gggctgctcg aggaacggcg tgaaatcatg cgtccaacga cgccgttttc gctcttcttg     960
atagaatatc atcagcgtga tccgatcttc gggcgcttca tggctctctg ctccatgctg    1020
cctcaacttt tattcgccgc agaggtcaca gctgtctact gttggcgaag tccgcgcgca    1080
ttgctcctag ctgttggcca gattgtgaac gagacgctga gctacgcact caagcgatcg    1140
tgtcggatac ctcgcccgcc aatcgctcga ctggaagcag atgcgttcgg ttggccctct    1200
tcacacgctc agttcatgtc ctacttgtac gtttttctacg tactctatgt gtctaggcca    1260
cagcgcaagg catcatcgag ccacaacggt gaaatgatgc accagacgct tccgaagcgg    1320
aggaagacga ccgattcaat ttcggaaacc gtggcagtga tgtttttgct aggtctgtca    1380
tccgttctgg tggctgcctc aagagtatac ctggcatatc attatcccag tcaggtttgg    1440
```

-continued

```
tatggaatca tcatgggcac tattttcgcg ataacctggt ccttgcgag tgaaaacgtt     1500 ttcttatcct acgttcgatc attgcggatt ctcgtatggc tcgggttcgg cgaagatgac     1560
tctgacctgt ttcgcagtat actcagagat gtgcat                              1596
```

<210> SEQ ID NO 22
<211> LENGTH: 532
<212> TYPE: PRT
<213> ORGANISM: Cyanidioschyzon merolae

<400> SEQUENCE: 22

```
Met Leu Leu Ala Glu Ser Leu Gly Gly Val Ala Phe Val Thr Val His
1               5                   10                  15

Thr Val Leu Cys Val Ala Val Leu Tyr Leu Pro Trp Asn Arg Gly Asp
            20                  25                  30

Arg Glu Ser Phe Arg Val Thr Cys Leu Gly Ala Leu Ser Thr Cys Ala
        35                  40                  45

Val Ile Ala Leu Ser Leu Val Asn Leu Gln Leu Phe Phe Thr Gly Leu
    50                  55                  60

Thr Trp Arg Glu Leu Ser Arg Thr Tyr His Trp Leu Arg Pro Trp His
65                  70                  75                  80

Ser Trp Gln Val Tyr Leu Leu Asp Ser Gly Gly Phe Leu Val Leu Leu
                85                  90                  95

Phe Leu His Glu Tyr Arg Lys Arg Gln Gln Thr Pro Val Lys Ser Ser
            100                 105                 110

Ser Ser Ser Thr Cys Ala Ser Thr Ser Gln Ser Ala Cys Pro Asn Ala
            115                 120                 125

Glu Asn Gly Ile Tyr Arg Asn Glu Arg Arg Asn Thr Trp Cys Met Phe
    130                 135                 140

Arg Ser Leu Leu Ile Ala Pro Ile Thr Glu Glu Leu Leu Phe Arg Cys
145                 150                 155                 160

Val Phe Asp Ala Ala Met Arg Ser Ala Gln Val Pro Glu Leu Ala Ser
            165                 170                 175

Met Ile Phe Asn Gly Val Met Phe Ala Val Ala His Ala His His Tyr
            180                 185                 190

Phe Arg His Gln Ser Arg Ser Leu Leu Gly Lys Gln Leu Leu Val Thr
            195                 200                 205

Phe Cys Phe Gly Cys Val Gln Val Val Cys Leu Arg Arg Thr Asp Tyr
    210                 215                 220

Ser Leu Trp Ala Cys Ile Ala Thr His Ala Leu Ala Asn Ala Leu Asp
225                 230                 235                 240

Leu Gln Lys Val Phe Ser Asp Arg Gly Ala Ser His Phe Leu Tyr Gly
            245                 250                 255

Asp Val Gly His Gln Leu Gly Ala Leu Leu Gln Ala Ala Ala Pro Leu
            260                 265                 270

Val Phe Ile Leu Arg Tyr Ala Leu Asp Met Ala Met Gln Ala Ser Pro
    275                 280                 285

Phe Arg Ser Ser Ile Leu Gln Val His Ala Asp Pro Gly Leu Leu Glu
    290                 295                 300

Glu Arg Arg Glu Ile Met Arg Pro Thr Thr Pro Phe Ser Leu Phe Leu
305                 310                 315                 320

Ile Glu Tyr His Gln Arg Asp Pro Ile Phe Gly Arg Phe Met Ala Leu
            325                 330                 335

Cys Ser Met Leu Pro Gln Leu Leu Phe Ala Ala Glu Val Thr Ala Val
            340                 345                 350
```

-continued

```
Tyr Cys Trp Arg Ser Pro Arg Ala Leu Leu Leu Ala Val Gly Gln Ile
        355                 360                 365

Val Asn Glu Thr Leu Ser Tyr Ala Leu Lys Arg Ser Cys Arg Ile Pro
    370                 375                 380

Arg Pro Pro Ile Ala Arg Leu Glu Ala Asp Ala Phe Gly Trp Pro Ser
385                 390                 395                 400

Ser His Ala Gln Phe Met Ser Tyr Leu Tyr Val Phe Tyr Val Leu Tyr
                405                 410                 415

Val Ser Arg Pro Gln Arg Lys Ala Ser Ser Ser His Asn Gly Glu Met
                420                 425                 430

Met His Gln Thr Leu Pro Lys Arg Arg Lys Thr Thr Asp Ser Ile Ser
                435                 440                 445

Glu Thr Val Ala Val Met Phe Leu Leu Gly Leu Ser Ser Val Leu Val
    450                 455                 460

Ala Ala Ser Arg Val Tyr Leu Ala Tyr His Tyr Pro Ser Gln Val Trp
465                 470                 475                 480

Tyr Gly Ile Ile Met Gly Thr Ile Phe Ala Ile Thr Trp Phe Leu Ala
                485                 490                 495

Ser Glu Asn Val Phe Leu Ser Tyr Val Arg Ser Leu Arg Ile Leu Val
                500                 505                 510

Trp Leu Gly Phe Gly Glu Asp Asp Ser Asp Leu Phe Arg Ser Ile Leu
                515                 520                 525

Arg Asp Val His
    530
```

```
<210> SEQ ID NO 23
<211> LENGTH: 1251
<212> TYPE: DNA
<213> ORGANISM: Cyanidioschyzon merolae

<400> SEQUENCE: 23
atgagctgca aaggtgcagc ttttgggttc gccactctaa atggcttgtc agttcggagg        60
catttgtttt gtaggagttc ggcaaatcgt agagtctgcg ggaagctttt tactggttca       120
caatgtccac gtgctccaag gtattttttg gtgcacactg acaagagtgc cggcaacact       180
ccaagtacac gaggtgggga ggaatatgcg ggaaacttta ttttcaggcc tccgcacgtt       240
atcgtaaggc cctcacagcg cacagcctac gggactggaa acggtacacc gctgccacca       300
aaagctctcg ttcactttct cggggggtgcc ttcgttggag ccgcgccgca ggttgcgtat       360
cgatggtttc tcgaacagtt ggctttagag ggcttcgtag tagtcgcgac gccgtaccga       420
ctttctttcg atcacctttg acgatggat gacgtgctca ccaggttttc agcagcagcg       480
ggaatgctcg ctctcgatta cggtcccatc cctgttgttg aatcggtca ctccctgggc       540 gctctcctgc acacccttgg aggcagcttg ttttgcaacg cggatgggta caaggctgcc       600
aacgtactga ttgcattcaa taatcgccgc gcggaagatg cgataccttt attcagagag       660
tttatcgcgc ccgtggttaa gacggttgcc caaactggtg aactctctga tgtgatcgag       720
cggctcgtga tcgatgggcc tgcgacgttt gacacgctgt cgacactgt tacagatgtt       780 gtgtttcctg gttctcggga tagtgagctt ttcgccttgg tgcgacagtc aagggcgctt       840
gcgcagcaga ttccaccttt atttgctgag gtcgctgatg gagcttttgc attcaaccct       900
gatcctatcg aggtcatgga ggcaattcgc acactataca agttcgtca aacgcttatt       960 gtgagcttca aaaacgacat cctcgatgac tcgcgttcgc ttcagaaagc actagaccct      1020
```

-continued

```
gagcgaggcg ctacagtaat tcgtctcggc ggaactcact taaccccctg cgcacaggat      1080
ttcctcgacc cacggctccg gcaaagcagc tttttctctt catttacgtg cgaaaaggat      1140
aacgacacat cctacatact ccgcgaagct atgcgcagaa ttgtgcttcg cgaagcaatg      1200
ctcatgaaaa acagtgttgt ggcgtattta gatcgcgctc tcggaatgga a              1251
```

```
<210> SEQ ID NO 24
<211> LENGTH: 417
<212> TYPE: PRT
<213> ORGANISM: Cyanidioschyzon merolae

<400> SEQUENCE: 24

Met Ser Cys Lys Gly Ala Ala Phe Gly Phe Ala Thr Leu Asn Gly Leu
1               5                   10                  15

Ser Val Arg Arg His Leu Phe Cys Arg Ser Ser Ala Asn Arg Arg Val
                20                  25                  30

Cys Gly Lys Leu Phe Thr Gly Ser Gln Cys Pro Arg Ala Pro Arg Tyr
            35                  40                  45

Phe Leu Val His Thr Asp Lys Ser Ala Gly Asn Thr Pro Ser Thr Arg
        50                  55                  60

Gly Trp Glu Glu Tyr Ala Gly Asn Phe Ile Phe Arg Pro Pro His Val
65                  70                  75                  80

Ile Val Arg Pro Ser Gln Arg Thr Ala Tyr Gly Thr Gly Asn Gly Thr
                85                  90                  95

Pro Leu Pro Pro Lys Ala Leu Val His Phe Leu Gly Gly Ala Phe Val
                100                 105                 110

Gly Ala Ala Pro Gln Val Ala Tyr Arg Trp Phe Leu Glu Gln Leu Ala
            115                 120                 125

Leu Glu Gly Phe Val Val Val Ala Thr Pro Tyr Arg Leu Ser Phe Asp
        130                 135                 140

His Leu Trp Thr Met Asp Asp Val Leu Thr Arg Phe Ser Ala Ala Ala
145                 150                 155                 160

Gly Met Leu Ala Leu Asp Tyr Gly Pro Ile Pro Val Val Gly Ile Gly
                165                 170                 175

His Ser Leu Gly Ala Leu Leu His Thr Leu Gly Gly Ser Leu Phe Cys
            180                 185                 190

Asn Ala Asp Gly Tyr Lys Ala Ala Asn Val Leu Ile Ala Phe Asn Asn
            195                 200                 205

Arg Arg Ala Glu Asp Ala Ile Pro Leu Phe Arg Glu Phe Ile Ala Pro
        210                 215                 220

Val Val Lys Thr Val Ala Gln Thr Gly Glu Leu Ser Asp Val Ile Glu
225                 230                 235                 240

Arg Leu Val Ile Asp Gly Pro Ala Thr Phe Asp Thr Leu Phe Asp Thr
                245                 250                 255

Val Thr Asp Val Val Phe Pro Gly Ser Arg Asp Ser Glu Leu Phe Ala
            260                 265                 270

Leu Val Arg Gln Ser Arg Ala Leu Ala Gln Gln Ile Pro Pro Leu Phe
            275                 280                 285

Ala Glu Val Ala Asp Gly Ala Phe Ala Phe Asn Pro Asp Pro Ile Glu
        290                 295                 300

Val Met Glu Ala Ile Arg Thr Leu Tyr Lys Val Arg Gln Thr Leu Ile
305                 310                 315                 320

Val Ser Phe Lys Asn Asp Ile Leu Asp Asp Ser Arg Ser Leu Gln Lys
                325                 330                 335
```

-continued

```
Ala Leu Asp Pro Glu Arg Gly Ala Thr Val Ile Arg Leu Gly Gly Thr
            340                 345                 350

His Leu Thr Pro Cys Ala Gln Asp Phe Leu Asp Pro Arg Leu Arg Gln
            355                 360                 365

Ser Ser Phe Phe Ser Ser Phe Thr Cys Glu Lys Asp Asn Asp Thr Ser
            370                 375                 380

Tyr Ile Leu Arg Glu Ala Met Arg Arg Ile Val Leu Arg Glu Ala Met
385                 390                 395                 400

Leu Met Lys Asn Ser Val Val Ala Tyr Leu Asp Arg Ala Leu Gly Met
                405                 410                 415

Glu

<210> SEQ ID NO 25
<211> LENGTH: 447
<212> TYPE: DNA
<213> ORGANISM: Cyanidioschyzon merolae

<400> SEQUENCE: 25
atgaacgact accaaaagat tggggttact ttgagcgcaa tttccgtttt attttatggg         60
ctcggtgttg tactcttttt tgatacgggg ctgatctcca tagcaagtgt tctttcacc         120 tcgtcgctct ttttcatcct gggcttcaag agagccgccc gtttcttctt ctcaagaaga         180
aaacttcgcg cgagtgcgct cttcttcggc ggctttggcc tggtgctgtt gcgctggcca         240
gtgctgggga ctctggtcca agcggtcggt gcgctctggc tattcctgag cttcattccg         300
atcgcgatga cgtttcttcg acaggttccg gttctgggtc agcttgtcga caccagcatt         360
gttcggcgga tactgcgccg cctatcggca gcctctggat acctggaaac gaacggtggc         420
atcggtttcg aaccgaaact cccggta                                           447

<210> SEQ ID NO 26
<211> LENGTH: 149
<212> TYPE: PRT
<213> ORGANISM: Cyanidioschyzon merolae

<400> SEQUENCE: 26

Met Asn Asp Tyr Gln Lys Ile Gly Val Thr Leu Ser Ala Ile Ser Val
1               5                   10                  15

Leu Phe Tyr Gly Leu Gly Val Val Leu Phe Phe Asp Thr Gly Leu Ile
            20                  25                  30

Ser Ile Ala Ser Val Leu Phe Thr Ser Ser Leu Phe Phe Ile Leu Gly
            35                  40                  45

Phe Lys Arg Ala Ala Arg Phe Phe Phe Ser Arg Arg Lys Leu Arg Ala
        50                  55                  60

Ser Ala Leu Phe Phe Gly Gly Phe Gly Leu Val Leu Leu Arg Trp Pro
65                  70                  75                  80

Val Leu Gly Thr Leu Val Gln Ala Val Gly Ala Leu Trp Leu Phe Leu
                85                  90                  95

Ser Phe Ile Pro Ile Ala Met Thr Phe Leu Arg Gln Val Pro Val Leu
            100                 105                 110

Gly Gln Leu Val Asp Thr Ser Ile Val Arg Arg Ile Leu Arg Arg Leu
            115                 120                 125

Ser Ala Ala Ser Gly Tyr Leu Glu Thr Asn Gly Gly Ile Gly Phe Glu
        130                 135                 140

Pro Lys Leu Pro Val
145
```

-continued

```
<210> SEQ ID NO 27
<211> LENGTH: 2118
<212> TYPE: DNA
<213> ORGANISM: Cyanidioschyzon merolae

<400> SEQUENCE: 27
atgcatcagc aggaccctga cgagataccg ctttctgaac tccttgggaa ctctggagaa        60
tcggtgccga gagttgtttc agttgccaga caaggtggct tcggcgcacc gtcgatacag       120
gttgccaaga agtcttcctc agctgcactt tcggaagatg aactgcctct agctctactt       180
attggtacgg aaagaaagaa ggagtgcagt agaaggaagg gcaaagtcga accatgtcga       240
aaagcgccga aaaggaaatg cgaacgaatg aaagccgaaa agcaccgcaa ggcgaaaaag       300
ttgcaggcaa caagtactaa acatagagcg gaagatgaat cgatcaagtg gtgcagcctc       360
gaacataacg gagtcttatt ccctccggaa tatgaaccgc acggacggcc tctactctac       420
gatggctgcg aaatagcgct cccgcccgag gccgaagaag tggccacctt ttatgcgtcg       480
aagttgggaa ctgtttattt agaaaaggaa acatttcgga aaaactttt tgacgactt      540 cggaagacct tgcccgttga tttacggaag cgcatcgtga aactcgaaca ctgtgacttc       600
agccgtatcc gggagtatct cgacgagctg aaagaacgaa aacaaagcat gcctccaagc       660
aaacggaaag agttacgaga gcggaagcg caaagagttg cgcattacac ggttgcaatc        720
gttgatggac gcaaggagaa agtggccaat tatcgtgtcg agcctccggg tctcttcctg        780
gggcgcggtg accatccgct aatgggccga gtcaaacgtc gcatattccc agaggatgtc       840
acactgaatc ttggtcgtga cgcacctatt ccgccgtgtc catttaaagg ccatgactgg       900
ggatccatcg tgcacaacca gagggtcacg tggctggctt gctggcgaga tccaatctcc       960
gatgagtaca gtacgtctg gctgagtgcg tcttcgcact tcaaggcgat gagcgatcaa      1020
gaaaaatttg agaaggcgca gcagctgagc aagcatatca cgaagatacg caatgagtac      1080
acgaaaggat tagaatctgc tgataggcac acgcagcaga gatccgtcgc actgtatctt       1140
attgataagc ttgcactccg agtcgggaac gagaaaggag aagacgaagc ggacactgtt      1200
ggttgctgct ccctgcgggt agaacacata acccttcaag agcctaatat agtgcagctc      1260
gactttctcg gcaaggattc gatgcgatac tttaacagag tgcgagtcga agcgctagtt      1320
tttcatcgcc tgcgagagtt cttgaaagga aaacgagtat cagataatgt attcgacgaa      1380
ctgaaagtcg aggaacttaa tgactatttg aaaagcctaa tgccgggcct atctgcgaaa      1440 gttttttcgca cctacaatgc atcttacacc cttgataagc ttttgcacag cgtgaaaacc      1500
cctggaccgg atattcattc gcgccttctg ttctacaatg aggcgaacaa agatgtagct      1560
gtattatgta accatcagcg atcccttcca aagactcatt cgttaatgct tgaaagactg      1620
cgcgataagc tagaggagag cagagcgtat cttgaggcgc tcaaaatggc tcgaggaaag      1680
gctcaggcat ctccagacag ccgcgcacaa gtaacacgct ggcgacggcc agtagttgag      1740
attcccgagg actgctccct cgctgagcga aagcgcattc gcgaggaggc cgaaaagcga      1800
ccgaaagaaa aacaggtagt gaacatgggg ctcgcgtcta tcacacgagg aatagcgcaa      1860
acacaggaaa aaatcaggcg cctagaggct gacctgaaaa cgagggattc gctcgctacg      1920
gtgtcgttga gcacctctaa gatcaactat ttagatccgc gaataacagt tgcttggtgc      1980
aaaagacatg aggttcctat tgagcgaata ttccctcgcg cgctacagga aaagtttatg      2040
tggagtatgg gggtaagcga ggactttcgt ttcccaatca gcaacgtcgt ttcgaacgat      2100
ccctcagggg cttccaca                                                    2118
```

```
<210> SEQ ID NO 28
<211> LENGTH: 706
<212> TYPE: PRT
<213> ORGANISM: Cyanidioschyzon merolae

<400> SEQUENCE: 28

Met His Gln Gln Asp Pro Asp Glu Ile Pro Leu Ser Glu Leu Leu Gly
1               5                   10                  15

Asn Ser Gly Glu Ser Val Pro Arg Val Val Ser Val Ala Arg Gln Gly
                20                  25                  30

Gly Phe Gly Ala Pro Ser Ile Gln Val Ala Lys Lys Ser Ser Ser Ala
            35                  40                  45

Ala Leu Ser Glu Asp Glu Leu Pro Leu Ala Leu Leu Ile Gly Thr Glu
        50                  55                  60

Arg Lys Lys Glu Cys Ser Arg Arg Lys Gly Lys Val Glu Pro Cys Arg
65                  70                  75                  80

Lys Ala Pro Lys Arg Lys Cys Glu Arg Met Lys Ala Glu Lys His Arg
                85                  90                  95

Lys Ala Lys Lys Leu Gln Ala Thr Ser Thr Lys His Arg Ala Glu Asp
            100                 105                 110

Glu Ser Ile Lys Trp Cys Ser Leu Glu His Asn Gly Val Leu Phe Pro
            115                 120                 125

Pro Glu Tyr Glu Pro His Gly Arg Pro Leu Leu Tyr Asp Gly Cys Glu
        130                 135                 140

Ile Ala Leu Pro Pro Glu Ala Glu Glu Val Ala Thr Phe Tyr Ala Ser
145                 150                 155                 160

Lys Leu Gly Thr Val Tyr Leu Glu Lys Glu Thr Phe Arg Lys Asn Phe
                165                 170                 175

Phe Asp Asp Phe Arg Lys Thr Leu Pro Val Asp Leu Arg Lys Arg Ile
            180                 185                 190

Val Lys Leu Glu His Cys Asp Phe Ser Arg Ile Arg Glu Tyr Leu Asp
            195                 200                 205

Glu Leu Lys Glu Arg Lys Gln Ser Met Pro Pro Ser Lys Arg Lys Glu
        210                 215                 220

Leu Arg Glu Ala Glu Ala Gln Arg Val Ala His Tyr Thr Val Ala Ile
225                 230                 235                 240

Val Asp Gly Arg Lys Glu Lys Val Ala Asn Tyr Arg Val Glu Pro Pro
                245                 250                 255

Gly Leu Phe Leu Gly Arg Gly Asp His Pro Leu Met Gly Arg Val Lys
            260                 265                 270

Arg Arg Ile Phe Pro Glu Asp Val Thr Leu Asn Leu Gly Arg Asp Ala
            275                 280                 285

Pro Ile Pro Pro Cys Pro Phe Lys Gly His Asp Trp Gly Ser Ile Val
        290                 295                 300

His Asn Gln Arg Val Thr Trp Leu Ala Cys Trp Arg Asp Pro Ile Ser
305                 310                 315                 320

Asp Glu Tyr Lys Tyr Val Trp Leu Ser Ala Ser Ser His Phe Lys Ala
                325                 330                 335

Met Ser Asp Gln Glu Lys Phe Glu Lys Ala Gln Gln Leu Ser Lys His
            340                 345                 350

Ile Thr Lys Ile Arg Asn Glu Tyr Thr Lys Gly Leu Glu Ser Ala Asp
            355                 360                 365

Arg His Thr Gln Gln Arg Ser Val Ala Leu Tyr Leu Ile Asp Lys Leu
```

-continued

```
              370             375             380
Ala Leu Arg Val Gly Asn Glu Lys Gly Glu Asp Glu Ala Asp Thr Val
385                 390             395                 400

Gly Cys Cys Ser Leu Arg Val Glu His Ile Thr Leu Gln Glu Pro Asn
                405             410             415

Ile Val Gln Leu Asp Phe Leu Gly Lys Asp Ser Met Arg Tyr Phe Asn
                420             425             430

Arg Val Arg Val Glu Ala Leu Val Phe His Arg Leu Arg Glu Phe Leu
                435             440             445

Lys Gly Lys Arg Val Ser Asp Asn Val Phe Asp Glu Leu Lys Val Glu
        450             455             460

Glu Leu Asn Asp Tyr Leu Lys Ser Leu Met Pro Gly Leu Ser Ala Lys
465             470             475             480

Val Phe Arg Thr Tyr Asn Ala Ser Tyr Thr Leu Asp Lys Leu Leu His
                485             490             495

Ser Val Lys Thr Pro Gly Pro Asp Ile His Ser Arg Leu Leu Phe Tyr
                500             505             510

Asn Glu Ala Asn Lys Asp Val Ala Val Leu Cys Asn His Gln Arg Ser
            515             520             525

Leu Pro Lys Thr His Ser Leu Met Leu Glu Arg Leu Arg Asp Lys Leu
        530             535             540

Glu Glu Ser Arg Ala Tyr Leu Glu Ala Leu Lys Met Ala Arg Gly Lys
545                 550             555                 560

Ala Gln Ala Ser Pro Asp Ser Arg Ala Gln Val Thr Arg Trp Arg Arg
                565             570             575

Pro Val Val Glu Ile Pro Glu Asp Cys Ser Leu Ala Glu Arg Lys Arg
                580             585             590

Ile Arg Glu Glu Ala Glu Lys Arg Pro Lys Glu Lys Gln Val Val Asn
                595             600             605

Met Gly Leu Ala Ser Ile Thr Arg Gly Ile Ala Gln Thr Gln Glu Lys
            610             615             620

Ile Arg Arg Leu Glu Ala Asp Leu Lys Thr Arg Asp Ser Leu Ala Thr
625                 630             635                 640

Val Ser Leu Ser Thr Ser Lys Ile Asn Tyr Leu Asp Pro Arg Ile Thr
                645             650             655

Val Ala Trp Cys Lys Arg His Glu Val Pro Ile Glu Arg Ile Phe Pro
                660             665             670

Arg Ala Leu Gln Glu Lys Phe Met Trp Ser Met Gly Val Ser Glu Asp
                675             680             685

Phe Arg Phe Pro Ile Ser Asn Val Val Ser Asn Asp Pro Ser Gly Ala
        690             695             700

Ser Thr
705
```

```
<210> SEQ ID NO 29
<211> LENGTH: 600
<212> TYPE: DNA
<213> ORGANISM: Cyanidioschyzon merolae

<400> SEQUENCE: 29
cgacgagaac gtataaggag tgcgcacggc gttttgttac aataccgata gatgagtttc        60
gaacatcgca ttcacaccat gagcgggggc gcacgctcca gagagtggag atggaaaagt       120
gccagcggag ccctgaggat gcaaaaaagt acgaccgct gacggaagag caaatggaaa       180
```

```
ggagggcgaa acttcgaggg ctacttgcat tagtaagtac aaccaacgat ggtaagaaac        240
gtatggagtt tgcgaaccga gactttaacg ctgccatcaa tatcaggaga tgtgcggtgc        300
tggagacgag acctccagag tgaacaagaa ggtacttttt tggacaacct tctaaggtcg        360
aactatatga gataaaattg gaagaagtag ttggtggccg gtccaaaaag acggggaggc        420
gtctgcacat cagttggaga cgttttgtcc aaggcgcgcc gatcgccact actgtacacg        480
gccggcgaga acgtggcgag aatacgcaag cgagctcgcc ggctgcgctc gctgcaccac        540
cgtcttttga ctcacaactt cgcgatatct ttgttctctg tgtttcttcg ttcgttgacc        600

<210> SEQ ID NO 30
<211> LENGTH: 599
<212> TYPE: DNA
<213> ORGANISM: Cyanidioschyzon merolae

<400> SEQUENCE: 30
gcctcgaggg cctctctgcg tcgtcgccga agagctgaca gaaagcgttc caggtgcgcg         60
agcctcactt gggcatatac cagtgagtgg gtgcgggcac cactagtccg gtgaactcgg        120
ccggtcagcc aaatcctcca cccggaaggt tcgcaccgtc actgcagcga gcgcagtcca        180
agcttctagg cgcggtaggc gtgcaggatg cgcgtccaat tcggcaagat gcgctgccgg        240
catgcccgcc catgtgtcgg acccattccg tgcaagcgag gcacgtcgag cgatttgggg        300
cgcgtgcata ggcccgcgca cgatgaatga tctggttgca tgcgtacaca aacaggactt        360
ttctgaccat gatatcccta ttcggacatg acgcatcgcg cacttccgca cacctcgtt        420 gctgggcgca gccggccgcg gcacctcgcg agcacgccgg cctcggcagc gcgagcgcat        480
tagcgagatc tccgacgacg gacgtgggtc gagattcgat ttcggaggcc gcacgacgca        540
aaaaggtcat tcgagtttgt gtctgcggac tctgaacgtt cctcgtaaag cacttctga        599

<210> SEQ ID NO 31
<211> LENGTH: 500
<212> TYPE: DNA
<213> ORGANISM: Cyanidioschyzon merolae

<400> SEQUENCE: 31
ccctcactgg catggcaaag ccgttctgtc tccgtgccgc atctgctcca ggggtgtaag         60
cgcgattgcg aatgctcaag gaaggttacg tgcacagtgg aatgcacgaa ataaccagta        120
catccgaaag gaagtacaag taatggaacc tgaaggtagg gtccagcagc atgatgggcg        180
ctttcccgaa tgtcaatacc gatctatcgc gcaatctggc ctccatggtc catagaagcg        240
ctttggcatc ggcgggagaa ccgggcgtcg ccccgcgctg cgctccatgg aacaatgctc        300
aaatcacgaa taaattgtac tttattaaat ctgtatgtac tatgatgtac aaaatagcat        360
tccaggaatc ccgagatcac acacgcgctc gagacgtgaa ctgtctcgtc actctcggct        420
acggcttcat cttcctcgta tttcttcgcc attagatacg agtgcggtaa gattctgggc        480
tgaagttttc aatattagtg                                                    500

<210> SEQ ID NO 32
<211> LENGTH: 4700
<212> TYPE: DNA
<213> ORGANISM: Artificial sequence
<220> FEATURE:
<223> OTHER INFORMATION: pQE80

<400> SEQUENCE: 32
tagctgagct tggactcctg ttgatagatc cagtaatgac ctcagaactc catctggatt         60
```

-continued

```
tgttcagaac gctcggttgc cgccgggcgt tttttattgg tgagaatcca agctagcttg      120
gcgagatttt caggagctaa ggaagctaaa atggagaaaa aaatcactgg atataccacc      180
gttgatatat cccaatggca tcgtaaagaa cattttgagg catttcagtc agttgctcaa      240
tgtacctata accagaccgt tcagctggat attacggcct ttttaaagac cgtaaagaaa      300
aataagcaca agttttatcc ggcctttatt cacattcttg cccgcctgat gaatgctcat      360
ccggaatttc gtatggcaat gaaagacggt gagctggtga tatgggatag tgttcaccct      420
tgttacaccg ttttccatga gcaaactgaa acgttttcat cgctctggag tgaataccac      480
gacgatttcc ggcagtttct acacatatat tcgcaagatg tggcgtgtta cggtgaaaac      540
ctggcctatt tccctaaagg gtttattgag aatatgtttt tcgtctcagc caatccctgg      600
gtgagtttca ccagttttga tttaaacgtg gccaatatgg acaacttctt cgcccccgtt      660
ttcaccatgg gcaaatatta tacgcaaggc gacaaggtgc tgatgccgct ggcgattcag      720
gttcatcatg ccgtttgtga tggcttccat gtcggcagaa tgcttaatga attacaacag      780
tactgcgatg agtggcaggg cggggcgtaa ttttttttaag gcagttattg gtgcccttaa      840
acgcctgggg taatgactct ctagcttgag gcatcaaata aaacgaaagg ctcagtcgaa      900
agactgggcc tttcgtttta tctgttgttt gtcggtgaac gctctcctga gtaggacaaa      960
tccgccctct agattacgtg cagtcgatga taagctgtca aacatgagaa ttgtgcctaa     1020
tgagtgagct aacttacatt aattgcgttg cgctcactgc ccgctttcca gtcgggaaac     1080
ctgtcgtgcc agctgcatta atgaatcggc caacgcgcgg ggagaggcgg tttgcgtatt     1140
gggcgccagg gtggtttttc ttttcaccag tgagacgggc aacagctgat tgcccttcac     1200
cgcctggccc tgagagagtt gcagcaagcg gtccacgctg gtttgcccca gcaggcgaaa     1260
atcctgtttg atggtggtta acggcgggat ataacatgag ctgtcttcgg tatcgtcgta     1320
tcccactacc gagatatccg caccaacgcg cagcccggac tcggtaatgg cgcgcattgc     1380
gcccagcgcc atctgatcgt tggcaaccag catcgcagtg ggaacgatgc cctcattcag     1440
catttgcatg gtttgttgaa aaccggacat ggcactccag tcgccttccc gttccgctat     1500
cggctgaatt tgattgcgag tgagatattt atgccagcca gccagacgca gacgcgccga     1560
gacagaactt aatgggcccg ctaacagcgc gatttgctgg tgacccaatg cgaccagatg     1620
ctccacgccc agtcgcgtac cgtcttcatg ggagaaaata atactgttga tgggtgtctg     1680
gtcagagaca tcaagaaata cgccggaac attagtgcag gcagcttcca cagcaatggc      1740
atcctggtca tccagcggat agttaatgat cagcccactg acgcgttgcg cgagaagatt     1800
gtgcaccgcc gctttacagg cttcgacgcc gcttcgttct accatcgaca ccaccacgct     1860
ggcacccagt tgatcggcgc gagatttaat cgccgcgaca atttgcgacg cgcgtgcag      1920 ggccagactg gaggtggcaa cgccaatcag caacgactgt ttgcccgcca gttgttgtgc     1980
cacgcggttg ggaatgtaat tcagctccgc catcgccgct tccacttttt cccgcgtttt     2040
cgcagaaacg tggctggcct ggttcaccac gcgggaaacg gtctgataag agacaccggc     2100
atactctgcg acatcgtata acgttactgg tttcacattc accaccctga attgactctc     2160
ttccgggcgc tatcatgcca taccgcgaaa ggttttgcac cattcgatgg tgtcggaatt     2220
tcgggcagcg ttgggtcctg gccacgggtg cgcatgatct agagctgcct cgcgcgtttc     2280
ggtgatgacg gtgaaaacct ctgacacatg cagctcccgg agacggtcac agcttgtctg     2340
taagcggatg ccgggagcag acaagcccgt cagggcgcgt cagcgggtgt tggcgggtgt     2400
```

-continued

```
cggggcgcag  ccatgaccca  gtcacgtagc  gatagcggag  tgtatactgg  cttaactatg    2460
cggcatcaga  gcagattgta  ctgagagtgc  accatatgcg  gtgtgaaata  ccgcacagat    2520
gcgtaaggag  aaaataccgc  atcaggcgct  cttccgcttc  ctcgctcact  gactcgctgc    2580
gctcggtcgt  tcggctgcgg  cgagcggtat  cagctcactc  aaaggcggta  atacggttat    2640
ccacagaatc  aggggataac  gcaggaaaga  acatgtgagc  aaaaggccag  caaaaggcca    2700
ggaaccgtaa  aaaggccgcg  ttgctggcgt  ttttccatag  gctccgcccc  cctgacgagc    2760
atcacaaaaa  tcgacgctca  agtcagaggt  ggcgaaaccc  gacaggacta  taaagatacc    2820
aggcgtttcc  ccctggaagc  tccctcgtgc  gctctcctgt  tccgaccctg  ccgcttaccg    2880
gatacctgtc  cgcctttctc  ccttcgggaa  gcgtggcgct  ttctcatagc  tcacgctgta    2940
ggtatctcag  ttcggtgtag  gtcgttcgct  ccaagctggg  ctgtgtgcac  gaacccccccg   3000 ttcagcccga  ccgctgcgcc  ttatccggta  actatcgtct  tgagtccaac  ccggtaagac    3060
acgacttatc  gccactggca  gcagccactg  gtaacaggat  tagcagagcg  aggtatgtag    3120
gcggtgctac  agagttcttg  aagtggtggc  ctaactacgg  ctacactaga  aggacagtat    3180
ttggtatctg  cgctctgctg  aagccagtta  ccttcggaaa  aagagttggt  agctcttgat    3240
ccggcaaaca  aaccaccgct  ggtagcggtg  gttttttttgt  ttgcaagcag  cagattacgc   3300
gcagaaaaaa  aggatctcaa  gaagatcctt  tgatctttc  tacggggtct  gacgctcagt     3360
ggaacgaaaa  ctcacgttaa  gggattttgg  tcatgagatt  atcaaaaagg  atcttcacct    3420
agatcctttt  aaattaaaaa  tgaagtttta  aatcaatcta  aagtatatat  gagtaaactt    3480
ggtctgacag  ttaccaatgc  ttaatcagtg  aggcacctat  ctcagcgatc  tgtctatttc     3540
gttcatccat  agttgcctga  ctccccgtcg  tgtagataac  tacgatacgg  gagggcttac    3600
catctggccc  cagtgctgca  atgataccgc  gagacccacg  ctcaccggct  ccagatttat    3660
cagcaataaa  ccagccagcc  ggaagggccg  agcgcagaag  tggtcctgca  actttatccg    3720
cctccatcca  gtctattaat  tgttgccggg  aagctagagt  aagtagttcg  ccagttaata    3780
gtttgcgcaa  cgttgttgcc  attgctacag  gcatcgtggt  gtcacgctcg  tcgtttggta    3840
tggcttcatt  cagctccggt  tcccaacgat  caaggcgagt  tacatgatcc  cccatgttgt    3900
gcaaaaaagc  ggttagctcc  ttcggtcctc  cgatcgttgt  cagaagtaag  ttggccgcag    3960
tgttatcact  catggttatg  gcagcactgc  ataattctct  tactgtcatg  ccatccgtaa    4020
gatgcttttc  tgtgactggt  gagtactcaa  ccaagtcatt  ctgagaatag  tgtatgcggc    4080
gaccgagttg  ctcttgcccg  gcgtcaatac  gggataatac  cgcgccacat  agcagaactt    4140
taaaagtgct  catcattgga  aaacgttctt  cggggcgaaa  actctcaagg  atcttaccgc    4200
tgttgagatc  cagttcgatg  taacccactc  gtgcacccaa  ctgatcttca  gcatctttta    4260
ctttcaccag  cgtttctggg  tgagcaaaaa  caggaaggca  aaatgccgca  aaaaagggaa    4320
taagggcgac  acggaaatgt  tgaatactca  tactcttcct  tttttcaatat  tattgaagca   4380 tttatcaggg  ttattgtctc  atgagcggat  acatatttga  atgtatttag  aaaaataaac    4440
aaataggggt  tccgcgcaca  tttccccgaa  aagtgccacc  tgacgtctaa  gaaaccatta    4500
ttatcatgac  attaacctat  aaaaataggc  gtatcacgag  gccctttcgt  cttcacctcg    4560
agaaatcata  aaaaatttat  ttgctttgtg  agcggataac  aattataata  gattcaattg    4620
tgagcggata  acaatttcac  acagaattca  ttaaagagga  gaaattaact  atgagaggat    4680
cgcatcacca  tcaccatcac                                                   4700
```

```
<210> SEQ ID NO 33
<211> LENGTH: 1986
<212> TYPE: DNA
<213> ORGANISM: Cyanidioschyzon merolae

<400> SEQUENCE: 33
gcgtgagtca gttcactgac aataagggaa acttgcgctt caaatgggag ccagccgagg        60
ccgtgttggc ggtggcattc gatgttcctg tgcccgggta tgatacatac aattgcatca       120
atctgcgctt gtgggacagt aagcctgcgc gtgagttcga tcttagctct ttcaacgttg       180
gcgactatta taagattctt gaaatgcggc agacgagtga gacgctctcc gccgtcctgt       240
acccgaacga tagcactgaa gcaggcaagg agctgcgcct caagcaacag tatttcttcg       300
tttcggcgac gctgcaggac atcattcgga ggttcctgaa gaaggaccga ccactcacgc       360
aacttgccga aaaagtgtgc attcagctga acgacacgca tccgacgatc gggattgttg       420
aaatgatgcg ccttctcctg gacgagtacg cattgggctg gacggatgcg tggaaaaccg       480
tcaaagcggt gttctcgtac acgaatcaca cggtgctgcc ggaggccttg gaaaagtggc       540
ctgtgccact catggaacgg ctcttgcctc gccacatgca gctcatcttc gaaatcaact       600
ttcgtcatct ccaggagtat gctcgtctaa gcaacaacga tggccatctg ttggagcgag       660
tgagcatcat cgaggagggt tttccaaaaa tggtgcgcat ggcccagctg gccgtcgttg       720
gctcacatac tgtcaatggt gtcgcggaaa tacactcgga actcgtgcga acccgtctct       780
tccctgattt taaccgcttc gagccgaaaa agtttgtgaa catcacaaac ggtgtgaccc       840
ctcgacgctg gatactggaa gcaaatcccg ccttgagtgc ggtgttttcc cgctggacgg       900
agagcgatga atggattttg gatttgaacc agatccgcca gttggaacag tacgccgaga       960
accctgacct gcaacgggaa ttttccgaag ccaaaaagga aaataagcgg cgtctcgctg      1020
aatacattcg agaaagaat ggcgtccacg tggatgtgaa tgccctcttc gacatccagg      1080
tcaagcgaat tcacgagtac aagcgccagt tgttgaatat tctcggtgtg attgcgcgct      1140
acaatttgat caagtcgggc aagcgtgatc tcgtgccgcg ggtcttcatc ttcggaggca      1200
aagcagcggc tggttacgca caagccaagc gcatcattcg tctcattaat ggtgtagcag      1260
acgtggtcaa caatgatcca gatgttggcg acctcctgaa agttgtattt ctcgaaaact      1320
acagcgtgtc tcttgccgag atcatcattc cggcgagcga cattagcgag catatatcga      1380
ctgccggcat ggaggcgtca ggaacagca acatgaagtt tgtgatgaac ggcggtctca      1440
tcatcggcac tatggacgga gcgaacattg aaatccgaga agaaatcggg ccggagaaca      1500
tctttatttt cggtctgttg gctcaagaag ttgaccaggc gcgcaatgaa ctcaagtacc      1560
atggctggaa atgtaccgat gggcgcttcc agaacgcact gggtcagctc agtcgcggta      1620
tgtactgcgg tcaagacact tttcaggaaa ttgtacgagc cctcgatcca gccaacgact      1680
actacctgat cagtcgcgac tttacctcgt atatggaagc ccaggatcgc gtcgacgctg      1740 cctatagga ccagcgctcg tggctggcta agtgtattgt gagcacggct cgcatgggta      1800
agttcagttc tgatcgcagt atccatgagt acgcggagcg catttggcgc attgagccat      1860
gtgcctatac accgtccagc atcacataca aggaaccagt tgagggtgtc tcagagccca      1920
ccgcagacgg tacagcgccg aagacgacgc tccgaggaac gtaaacatca agtcccgagg      1980
gtgacg                                                                  1986

<210> SEQ ID NO 34
<211> LENGTH: 600
<212> TYPE: DNA
```

<213> ORGANISM: Cyanidioschyzon merolae

<400> SEQUENCE: 34
cgacgagaac gtataaggag tgcgcacggc gttttgttac aataccgata gatgagtttc        60
gaacatcgca ttcacaccat gagcgggggc gcacgctcca gagagtggag atggaaaagt       120
gccagcggag ccctgaggat gcaaaaaagt acggaccgct gacggaagag caaatggaaa       180
ggagggcgaa acttcgaggg ctacttgcat tagtaagtac aaccaacgat ggtaagaaac       240
gtatggagtt tgcgaaccga gactttaacg ctgccatcaa tatcaggaga tgtgcggtgc       300
tggagacgag acctccagag tgaacaagaa ggtacttttt tggacaacct tctaaggtcg       360
aactatatga gataaaattg gaagaagtag ttggtggccg gtccaaaaag acggggaggc       420
gtctgcacat cagttggaga cgttttgtcc aaggcgcgcc gatcgccact actgtacacg       480
gccggcgaga acgtggcgag aatacgcaag cgagctcgcc ggctgcgctc gctgcaccac       540 cgtctttttga ctcacaactt cgcgatatct ttgttctctg tgtttcttcg ttcgttgacc       600

<210> SEQ ID NO 35
<211> LENGTH: 717
<212> TYPE: DNA
<213> ORGANISM: Cyanidioschyzon merolae

<400> SEQUENCE: 35
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccctgaccta cggcgtgcag tgcttcagcc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac       600
tacctgagca cccagtccgc cctgagcaaa gaccccaacg agaagcgcga tcacatggtc       660
ctgctggagt tcgtgaccgc cgccgggatc actctcggca tggacgagct gtacaag       717

<210> SEQ ID NO 36
<211> LENGTH: 200
<212> TYPE: DNA
<213> ORGANISM: Cyanidioschyzon merolae

<400> SEQUENCE: 36
taaactagct atttatctgg tacatatcat tcataagcac atgtttttgc gttgaaaccc        60
ggtaaaacac tcatgacgtt ttgtgttgaa ttgcaaccag cacgttatcg accagctctc       120
gaacaaaaca tcgctttata cgggagaagt tgctgcggta ttgaccagag cgtacgaaaa       180
cttgtgcagg caaaaagtgt                                                    200

<210> SEQ ID NO 37
<211> LENGTH: 2757
<212> TYPE: DNA
<213> ORGANISM: Cyanidioschyzon merolae

<400> SEQUENCE: 37

-continued

```
gaactgaggg gcgaacgcag tcctccttgc attgttaagc aaaaaatatt ctctacaagc      60
aatttgtgta caatctatat ggtacgctgc gtagagattt gcatgtcctg ctctacagtg     120
cgaagaagca ttctatttta cgcagcggga gtaaagcaaa atcgagttga acgactatct     180
gacgcctacg caaagcgatt ccgcgtaccg tgtatctgca aagtagcact tcttaatggt     240
agagccgcaa ttgagaacgt tcggagtgtt ttcctggttc tgctggatgg atttttggta     300
aactatattt aatcttctag tgggaggatg attgcgcggg caaaaccata ttttccagga     360
tgagtcgtac tgaaagaagc acagtattca ctatgccggg cgaggtaggt gctagtttgg     420
gtttgacctc acgcgatgcg cacaacggct gcggaatacg cacaactcga tactgatcgt     480
cgagtcggca agactgcaac atgctcatgg ctcaggtcat ccgaagagaa acctcaccat     540
aaataccgtg ttcatacttc acatcgtaca taagaaaaat tacttttcag gccctctaca     600
ataaataaaa ttggattcca cttatcgcgt ttattgagag atttaccgga cgcttccgtc     660
gcaaaaaaaa gaagagacat aagaaacttg acccactgtg tagaaggaga gcaaacaccg     720
caaagccctg cgaaaacctc atgcggtgat gtcgcgccct gctgcgatcg taacgaaggc     780
cattcgtcgc cacgcgcaac gcagggcaag agacggcttg cgtacggtgc agaacaccga     840
actggctgtg aagaggatct cttctttgtc agtactaaaa ggcgtcgctt tctgggaatg     900
gagcagcttg ccaaggatct ttttgagata ggtgcggtca agtttggcac gttcaaactc     960
aagtctggga tagcgtctcc attctatgtc gatctgcgcg ttgctgtctc gtatcctcga    1020
gttctgagaa gcattgcggc tctgtaccta gagtgcttgc aggacttttc tggcgctttc    1080
gacgttattt gcggggttcc atacactgcg ctccctttg cgacagcaat ggctgtgcag    1140
ggagacttac ctatggttat gtgtcgaaag gaggtcaaag accatggaac acggcgagtt    1200
gttgaaggtg ctttcacaca aggctctcgt tgcttaataa tcgaggacgt tgttacaagt    1260
ggttcaagta ttctggaagt tgtgggcgca ttgcgcgcag agggtctcaa agtggatcac    1320
gcgatcgtct tgcttgatag ggagcaaggc gggtgtgagg cgcttctcgg ccagggaata    1380
gggctccgat ctgtttttccg catcagcgac ctcgttggga cgctgcggaa tttgaacttg    1440
cttgagccgg ggaaggtgga tatgattcta gattttattc gcacggcccg cgcagcatca    1500
gatgttaagc gccccgaaac aaacgttcca tccgcattgc cagtcgccgc atcaagttct    1560
tccccggtgc gagatcaact ttactcaatc gcagaaaaaa agagaagcat attatgcgtt    1620
gcggcagacg tacaatcgac taaggagctt cttggaattg cagatgcagt aggccccac    1680 atctgtgttc tgaagttgca cgccgatatt atccaggact ggacgacgga cacatcaaga    1740
cgccttcgag agctcgcgga caaacacagt ttcatgcttt ttgaggatcg aaaattcgct    1800
gacataggaa acacggttgt tgcacagttc agcgcaggcg tacatcggat ctcttcctgg    1860
gcggacattg tcaatgcaca cgccatcccg ggccctggac tgattgaggg cctgcgccac    1920
gcttgcgcaa tttccggcag aatgattggc ctcctgttag tcgcacaaat gtccagcaaa    1980
gggaacttga ttgacgagag atacactgct acatgcctgc ggatggcccg cgaagcgttt    2040
ccgttctgta tcggcttcat tgcccaggag cgtctggacc cgacagggaa gctctttgtg    2100
atggcgcctg gtgtgcaact ggattcaaag ggcgatcaat taggccaaca gtacaattca    2160
ccacagtatc tgctgaagcg caagggtgtc gacttcctta tcgttggccg cggtatctac    2220
gggagtgaag agccagcaaa ggcggcccag atgtacaaag agttgtcgtg gagcgtcctt    2280
cacggctaat tcctaatggg cagaagcaag cgtcggctcc cacaaagttc agtagaacgg    2340
```

-continued

```
cgggggtcag ttgccacgaa cgctttacgt gcggcatcaa gatgatattt cattgcgaat   2400
ggagttcgtc gacgtcagtt gcatccgcag aatgcttctt tgtttcggat atgtccgcgg   2460
cctgtgcccg caacgaatgt tcctagaagt acatttcacg gcgccttgaa catgtagtta   2520
agataagcgc tcgaaatcgt ccctgattcg gcagtgactg tccctagagc tggatcctat   2580
ggtttcttga ccctgtggct acaatatgcg ctcgacaccg tcgaagatca gggaatcgct   2640
ctagtgtcgg cctgatttcc accaagtgca ctctgcactt tttgaaattt ttggaggacc   2700
cattaaaaaa ataaatgcaa ggattcctaa gaatagagat acagtcagct gctaggg     2757
```

```
<210> SEQ ID NO 38
<211> LENGTH: 1853
<212> TYPE: DNA
<213> ORGANISM: Cyanidioschyzon merolae

<400> SEQUENCE: 38
```

```
gaaaccgctc agcgaccaag cgactcgagc tcgccacctc gtcgcgtggt ctcgtcgatg    60
acctccttca tcgctaccaa gtagttcacg cgacgcaact tgcgcagatc ttttctcaga   120
agaaacctca ggtcactcac atcggggtac tttcggccac gcgtgttcgc aacttcaaca   180
cagcgctgca cgacagcggt gaggtacgtc cgcaacaagt cctcgacaag ctcagccgta   240
tcacgccgcg gctgccgcgc atccccgaaa ccgtacagca tctggcgaat ttcattctgg   300
aataagcgct tcgaagcgtc ttcttcgggg tcgttcgcga aaaaagcatc ccagtcgttt   360
ccatcgctgg actgcatcgc actcgccgac tcggttccta gcacgaggcc gctgcctaga   420
caacgcgacg tacgcagata ctgtaagcaa taatagtgct gatgctgcca ctaacgaacc   480
tcgagcgcgt gtcagggcgc atacacgtcg ttaacgtacc gcggtggcag gcacggcgag   540
cttggcgtat gcgcgatacg taaatacatg ctgcgttgga tagcgactct gctgccgcat   600
ggcgacgctt tcatcagatg cggcgctgct gggaagaagg ccgtatccgg tgcatctgga   660
tggtagtttt gtataataat aggcttaaat gtcgttgcgt tcaaaggatg tgcaatcttt   720
ctggaagaaa tggaatatat gggacaaaaa agtacggaag gaaaagcatc tttaggtcca   780
tatatgaata gattggacac tgcatttcct gggtccaata acgccatcga acaaaatgga   840
tatatcggac aaaacatgta cggaacgtga agcaccgttc cctacgtcat caacactaga   900
cctcgtgttc tctcgccgat gctccggagc tatatgtacg ggatcgggcg tgcgcctgcg   960
cgttcctctt ctggacaggg cagcatctcg gtagcaacta ctgcagtgac tcacgcgtga   1020
tggtgtttgt tgcacctgtt ctacgacacg tgagcaagca ccgggcaagg agcaagcgac   1080
tggtgcgcgc aagcgtcagc acgacggaat ggtacgtgcc ggcgacactg gcccccaggg   1140
tgtcggtgaa taacacccag aatcttcgca actggagcgc gccagtgcga accgttcgcg   1200
tccctgtggc tacggtaggc gttggttccg ttgaacagca ccaaaagcac ctcggacacc   1260
gcatagcgtt ttggcttcgg cgcgagaccc gtctgccgga ctgggctacc ttgatgttgg   1320
tgtcagcgct tcctgttgtt gagctacgcg gtggcgtgcc ggtagggctc tggctcggtt   1380
tgtcgccggc cgagactttt ctcttctgcg ttatcggcaa catgcttcca ataccgtttc   1440
tagtttttgg tcttcgacac gagcggatgc gtcgcctcgc gcgccccctg ttggactctg   1500
tggcgcggcg cctgccgagt catgcgaata ccccgtcgag tcaggcgctg gccctggcct   1560
tgtttgttgg cgtaccattg ccgggcactg gagcgtggtc tggcgctatt gccgcgttcc   1620
ttctgcaaat ggacatctgg cttgcgctgg tctccatcgc ggcgggcgtc gcgatcgctg   1680
gctgcatcat gattgcactc gttctaatgg gacgcatcgg tggactcatt gtcgcgtttg   1740
``` cgctttttagg agttggtgct agtgcgctgt ggcgcatgct gaaaccaccg tcgtcggcgg      1800
aaaactcgtg acatcaacgc cgccgcatct gagtgggtaa ggtcagcaag ctg             1853

<210> SEQ ID NO 39
<211> LENGTH: 200
<212> TYPE: DNA
<213> ORGANISM: Cyanidioschyzon merolae

<400> SEQUENCE: 39
cttatagctt acgtggcgga ttcgcagcga ttcgcgagat ttcccgaatc gccgatctcg       60
cgcgagatcc tcggcgaaga ttcgcggcgc atcatcgaac ggatcgcaga tgctgaaata      120
ccgcgcgcag cgaaattttt ccaacactag atttccattt gtgttctagc cgtggaaacc      180
tgtgagagaa ccagggattc                                                  200

<210> SEQ ID NO 40
<211> LENGTH: 1209
<212> TYPE: DNA
<213> ORGANISM: Cyanidioschyzon merolae

<400> SEQUENCE: 40
atggtgttta cgtgtgctgc tttcgtagct ccagttggtg gttttcgcgg cacggcggtg       60
cgcgctacga gccgcgaggc cgtcggaccc cggctgcagg ctggtgacca gcctggtgcc      120
ttcactgcac gtacgcgaag cttaggtgtg ccgctgacgc ggagccggca acgtgctgcg      180
cactcgaatc ttgtgatgaa ggtgcgggta gcggtttccg ggttcggtcg catcggacgc      240
aactttgtgc gctgcctgca agcgaccccg aatgcgaacc tggagctggt ggggatcaac      300
gatacggctg gcatcaaaac tgccgctcat ctgctgaagt acgactctat tctgggaatt      360
gcaccgtttg acgtgaaggt tagcgggggag agtaccatgc tcattgacgg gaagccggtt      420
accgttgtca gcaaccgcga tccgacccag ctgccttgga gggacctcaa cgtcgacatc      480
gtcatcgagg caacgggtgt ctttatctca agggacgggg caggcaagca catcgaagcg      540
ggtgccaaaa aggtggtcat cacagcgcca gcgaaaggcg aaggcgtccc gacctttgtc      600
atgggtctga caacacccca gtataaccac gccaccgacc atgtggtgag caacgcgtcg      660
tgcaccacca acggcatggc accgttcgtg aaggtgctcg acgaggaatt cggcatcgtt      720
tccggcatga tgaccacgac gcattcgtat accgggggacc agcgtctgct ggatgcatcg      780
catcgcgacc tgcgtcgcgc ccgtgcggcc gcgttgaaca tcgtgccgac ctcgacgggt      840
gccgcgcagg cggttgcgct ggtgtatcca ccagtgaagg gcaagctcac cggcattgcc      900
ctgcgagtgc cgacccgcaa cgtttctatc gtcgactttg tctgcacggt gaagaaacca      960
acgttcaagg aggaagtgaa tgcagctttc gtacgagcag cggaagggcc aatgaagggt     1020
atcctggcgg tgagcgatga gccgctcgtc tcatcggatt atcggatgaa cgtcaactca     1080
agcattgtgg atgcagcgct gacgacggtg atgggtgata cgctcgtcaa gtggtagcc      1140 tggtacgaca acgagtatgg ctacagtcaa cgggttgtgg acttggccaa ctacatagcg     1200
cagcatttc                                                            1209

<210> SEQ ID NO 41
<211> LENGTH: 1572
<212> TYPE: DNA
<213> ORGANISM: Artificial sequence
<220> FEATURE:
<223> OTHER INFORMATION: codon optimized GP -continued

```
<400> SEQUENCE: 41
atggttccac aagcactgtt gctcgtgcct attctaggct tttccctgtg tttcgggaag      60
tttccgattt acaccattcc tgacacgttg ggcccatgga gtccgatcga catccatcac     120
ctgagctgcc caaacaactt ggtggttgag gatgaaggtt gcacgaatct ttccggtttc     180
tcgtatatgg aactgaaggt tggttacact agtgcgatca aggtgaacgg ttttacatgc     240
acaggagtcg ttaccgaagc ggagacatat accaactttg taggctacgt gaccactacg     300
ttcaaacgga agcactttcg cccgactcct gatgcctgca gagctgctta caactggaag     360
atggcaggag atccgcgtta tgaggagtcg ctccactccc cgtatccaga ttaccattgg     420
ctgcgaacag tgaagacgac taaggagagc ctggtcatca tatcgccctc agttgctgac     480
ctcgacccct atgacaatag cctgcattcg cgggtctttc ctagtggcaa atgcagcggg     540
ataacccgct cttcggtgta ctgctccact aaccacgact acacggtgtg gatgcctgag     600
atcttgcgac tcggcacgtc atgcgacatt ttcaccaaca gtcgaggcaa acgcgtgagc     660
aaagggagta cgacgtgtgg cttcatcgac gagaggggcc tctacaagtc actcaaaggg     720
gcctgcaagc tcaagctgtg tggcgttctt ggcctacgct tgatggatgg aacctgggta     780
tcaatgcaga catccaatga gacgaagtgg tgtccaccaa atcagctcgt aaatctccac     840
gacttacgct ccgatgaact ggaacatctg gtgattgaag agctcgtcaa gaaacgcgaa     900
gagtgcttag atgcgctcga gtccatcatt acgacgaaaa gcgtcagctt ccgccggctt     960
tcacacctgc gaaagctggt tcccggcttt ggtaaggcct acacgatctt caacaagacc    1020
ttgatggagg cagaagccca ctacaaatcg gtgcgtacct ggaacgagat catacccctct   1080 aaagggtgtc ttcgggtcgg aggtcgttgt catccgcatg tcaatggggt gtttttcaac    1140
ggcattatcc ttggtcccga tggtcacgtc ctgattccgg agatgcagtc gagcctcttg    1200
cagcagcata tcgagctcct ggagtcgtct gtgattccgc ttatgcatcc actcgcggat    1260 cccttttaccg tgttcaagga cggtgacgaa actgaggact tcatcgaggt ccacttaccg   1320
gacgtccacg aacaggtatc gggagtggat ctggggctgc ctaactgggg aaagtatgtg    1380
ctgcttagcg caggaacgct aatcgcgctc gtttttgatca ttttcctaat gacctgttgc   1440
cgcaaggttg accggccgga aagtacgcaa cgctctctgc gtggtacagg ccgtaacgtc    1500
tcggttacgt cacaatcggg caaattcatc aacagctggg agtcgtacaa atccggtggc    1560
gaaacaggcc tt                                                       1572

<210> SEQ ID NO 42
<211> LENGTH: 717
<212> TYPE: DNA
<213> ORGANISM: Aequorea victoria

<400> SEQUENCE: 42
atgagcaagg gcgaggagct gttcaccggg gtggtgccca tcctggtcga gctggacggc      60
gacgtaaacg gccacaagtt cagcgtgcgt ggcgagggcg agggcgatgc caccaacggc     120
aagctgaccc tgaagttcat ctgcaccacc ggcaagctgc ccgtgccctg gcccaccctc     180
gtgaccaccc tgacctacgg cgtgcagtgc ttcagccgct accccgacca catgaagcgt     240
cacgacttct tcaagtccgc catgcccgaa ggctacgtcc aggagcgcac catctcgttc     300
aaggacgacg gcacatacaa gacccgcgcc gaggtgaagt tcgagggcga caccctggtg     360
aaccgcatcg agctgaaggg catcgacttc aaggaggacg gcaacatcct ggggcacaag     420
ctggagtaca actttaacag ccacaacgtc tatatcacag ccgacaagca gaagaacggc     480
```

```
atcaaggcaa acttcaagat ccgccacaac gttgaggacg gcagcgtgca gctcgccgac      540
cactaccagc agaacacccc catcggcgac ggccccgtgc tgctgcccga caaccactac      600
ctgagcaccc agtccgttct gagcaaagac cccaacgaga agcgcgatca catggtcctg      660
ctggagttcg tgaccgccgc cgggatcact cacggcatgg acgagctgta caagtaa        717
```

```
<210> SEQ ID NO 43
<211> LENGTH: 12
<212> TYPE: PRT
<213> ORGANISM: Artificial sequence
<220> FEATURE:
<223> OTHER INFORMATION: Col peptide

<400> SEQUENCE: 43

Ser Phe His Gln Leu Pro Ala Arg Ser Pro Leu Pro
1               5                   10
```

```
<210> SEQ ID NO 44
<211> LENGTH: 2781
<212> TYPE: DNA
<213> ORGANISM: Cyanidioschyzon merolae

<400> SEQUENCE: 44
gaactgaggg gcgaacgcag tcctccttgc attgttaagc aaaaaatatt ctctacaagc      60
aatttgtgta caatctatat ggtacgctgc gtagagattt gcatgtcctg ctctacagtg      120
cgaagaagca ttctatttta cgcagcggga gtaaagcaaa atcgagttga acgactatct      180
gacgcctacg caaagcgatt ccgcgtaccg tgtatctgca aagtagcact tcttaatggt      240
agagccgcaa ttgagaacgt tcggagtgtt ttcctggttc tgctggatgg attttttggta     300 aactatattt aatcttctag tgggaggatg attgcgcggg caaaaccata ttttccagga      360
tgagtcgtac tgaaagaagc acagtattca ctatgccggg cgaggtaggt gctagtttgg      420
gtttgacctc acgcgatgcg cacaacggct gcggaatacg cacaactcga tactgatcgt      480
cgagtcggca agactgcaac atgctcatgg ctcaggtcat ccgaagagaa acctcaccat      540
aaataccgtg ttcatacttc acatcgtaca taagaaaaat tactttttcag gccctctaca     600 ataaataaaa ttggattcca cttatcgcgt ttattgagag atttaccgga cgcttccgtc      660
gcaaaaaaaa gaagagacat aagaaacttg acccactgtg tagaaggaga gcaaacaccg      720
caaagccctg cgaaaacctc atgcggtgat gtcgcgccct gctgcgatcg taacgaaggc      780
cattcgtcgc cacgcgcaac gcagggcaag agacggcttg cgtacggtgc agaacaccga      840
actggctgtg aagaggatct cttctttgtc agtactaaaa ggcgtcgctt tctgggaatg      900
gagcagcttg ccaaggatct ttttgagata ggtgcggtca agtttggcac gttcaaactc      960
aagtctggga tagcgtctcc attctatgtc gatctgcgcg ttgctgtctc gtatcctcga      1020
gttctgagaa gcattgcggc tctgtaccta gagtgcttgc aggacttttc tggcgctttc      1080
gacgttattt gcggggttcc atacactgcg ctcccttttg cgacagcaat ggctgtgcag      1140
ggagacttac ctatggttat gtgtcgaaag gaggtcaaag accatggaac acggcgagtt      1200
gttgaaggtg ctttcacaca aggctctcgt tgcttaataa tcgaggacgt tgttacaagt      1260
ggttcaagta ttctggaagt tgtgggcgca ttgcgcgcag agggtctcaa agtggatcac      1320
gcgatcgtct tgcttgatag ggagcaaggc gggtgtgagg cgcttctcgg ccagggaata      1380
gggctccgat ctgtttttccg catcagcgac cttgtcggaa cactccgcca ctcaggtcgg      1440
ttatcagttg aacaagtaac cgagttgttt gattatttcc actcaaccaa agtatcatcg      1500
```

```
agtcctctga gtaactctat tcaaagtgga tataaagtgc atcctctttc ctttgaacaa       1560
cgtctttcat tgattcgaaa caaagttggc cgtcggctat tggaaattat gttaaagaag       1620
cagtcgaacc ttgcagtggc agcggatgta acaaccagtg aagaattatt atccattgcc       1680
aatgaagtgg gtccacaaat atgcatttta aagacacata tggatattat tcaagattgg       1740
acggaaagcg tatctgaaaa actcgttcat ttagctaagt tgcatcactt tttgatattt       1800
gaagacagaa agtttgcaga tattggcaat actgtggaat tacagttgac tggaggtata       1860
tttcatattg cacagtgggc agacatagtg aatgctcata tcattgctgg tcctggaact       1920
attcaagcgc taagtcgatc tgctgaacat tgcggtattt tgttattagc acaaatgagt       1980
agcaaaggga acttggcagt acaagaatat acgcaaaagg cattagaatt tgctcaacaa       2040
tatgaagatg ctgttttttgg ttttatatca ttgggttgta ttggagatcc aaactttctt      2100
tattttactc ctggagtgaa gttagaagga ggaggtgact ctttaggtca acaatatacg       2160
gatcctaaga cagttattgc tattcaagga agcgatgtag ctattgtagg gaggggaatt      2220
attcagtctt ctaatcgacg tgaagcagca tcaacttatc gaaaagcctg ttgggatgct       2280
tatttacaac gacttgaaga atacgttgaa taattcctaa tgggcagaag caagcgtcgg       2340
ctcccacaaa gttcagtaga acggcggggg tcagttgcca cgaacgcttt acgtgcggca       2400
tcaagatgat atttcattgc gaatggagtt cgtcgacgtc agttgcatcc gcagaatgct       2460
tctttgtttc ggatatgtcc gcggcctgtg cccgcaacga atgttcctag aagtacattt      2520
cacggcgcct tgaacatgta gttaagataa gcgctcgaaa tcgtccctga ttcggcagtg       2580
actgtcccta gagctggatc ctatggtttc ttgaccctgt ggctacaata tgcgctcgac       2640
accgtcgaag atcagggaat cgctctagtc tcggcctgat ttccaccaag tgcactctgc       2700 acttttttgaa atttttggag gacccattaa aaaaataaat gcaaggattc ctaagaatag       2760
agatacagtc agctgctagg g                                                 2781
```

<210> SEQ ID NO 45
<211> LENGTH: 390
<212> TYPE: DNA
<213> ORGANISM: Cyanidioschyzon merolae

<400> SEQUENCE: 45

```
atgttccatg tgacgtaccc gttcacgcag agacaatgct ttctccgttc acgagaagcg        60
tgccttgcaa cgttgccagc tggtgctttt cgaaagcacc tgtggcgccc ttcgtgctgg       120
tcgttccgca cacgtcttcg taaagaggcg tcgctacgga aatccacagt tctcgctccg       180
cttactcgcc gtctgcagct gagtctcttc ggcctcccag agcggttcgt tcgcaagtcc       240
aagtcgccgg tctcggcaga gtccagtgtc gccactgagc tcacacgtga tcgggtcaaa       300
gatccgacgc tcgcgaagta ctgggataca cttctggaaa tcaatgcact ggaggcggaa       360
ctggaacaac tcaaaagcga tgaactcaga                                        390
```

<210> SEQ ID NO 46
<211> LENGTH: 90
<212> TYPE: DNA
<213> ORGANISM: Artificial sequence
<220> FEATURE:
<223> OTHER INFORMATION: HA tag

<400> SEQUENCE: 46

```
atgtacccat acgatgttcc tgactatgcg ggctatccct atgacgtccc ggactatgca        60
```

-continued ggatacccctt atgacgttcc agattacgct                                      90

<210> SEQ ID NO 47
<211> LENGTH: 30
<212> TYPE: DNA
<213> ORGANISM: Artificial sequence
<220> FEATURE:
<223> OTHER INFORMATION: d184(+25)R

<400> SEQUENCE: 47
cgtcaccctc gggacttgat gtttacgttc                                       30

<210> SEQ ID NO 48
<211> LENGTH: 43
<212> TYPE: DNA
<213> ORGANISM: Artificial sequence
<220> FEATURE:
<223> OTHER INFORMATION: bT3'(+1)F

<400> SEQUENCE: 48
taaactagct atttatctgg tacatatcat tcataagcac atg                        43

<210> SEQ ID NO 49
<211> LENGTH: 39
<212> TYPE: DNA
<213> ORGANISM: Artificial sequence
<220> FEATURE:
<223> OTHER INFORMATION: HS(-200)Fd184

<400> SEQUENCE: 49
gtcccgaggg tgacgcttat agcttacgtg gcggattcg                             39

<210> SEQ ID NO 50
<211> LENGTH: 22
<212> TYPE: DNA
<213> ORGANISM: Artificial sequence
<220> FEATURE:
<223> OTHER INFORMATION: HS(-1)R

<400> SEQUENCE: 50
gaatccctgg ttctctcaca gg                                               22

<210> SEQ ID NO 51
<211> LENGTH: 35
<212> TYPE: DNA
<213> ORGANISM: Artificial sequence
<220> FEATURE:
<223> OTHER INFORMATION: J042(1)Fhs

<400> SEQUENCE: 51
gagaaccagg gattcatggt gtttacgtgt gctgc                                 35

<210> SEQ ID NO 52
<211> LENGTH: 41
<212> TYPE: DNA
<213> ORGANISM: Artificial sequence
<220> FEATURE:
<223> OTHER INFORMATION: J042(1209)R-link3

<400> SEQUENCE: 52
ggcgcctgca ccggatccga aatgctgcgc tatgtagttg g                          41

<210> SEQ ID NO 53
<211> LENGTH: 35
<212> TYPE: DNA
<213> ORGANISM: Artificial sequence
<220> FEATURE:
<223> OTHER INFORMATION: GP(1)F-linker3

<400> SEQUENCE: 53
tccggtgcag gcgccatggt tccacaagca ctgtt                                35

<210> SEQ ID NO 54
<211> LENGTH: 32
<212> TYPE: DNA
<213> ORGANISM: Artificial sequence
<220> FEATURE:
<223> OTHER INFORMATION: GP(1572)R-linker2

<400> SEQUENCE: 54
tccaccgcct ccaccaaggc ctgtttcgcc ac                                   32

<210> SEQ ID NO 55
<211> LENGTH: 35
<212> TYPE: DNA
<213> ORGANISM: Artificial sequence
<220> FEATURE:
<223> OTHER INFORMATION: sfGFP(1)F-linker2

<400> SEQUENCE: 55
ggtggaggcg gtggaggcat gagcaagggc gagga                                35

<210> SEQ ID NO 56
<211> LENGTH: 35
<212> TYPE: DNA
<213> ORGANISM: Artificial sequence
<220> FEATURE:
<223> OTHER INFORMATION: sfGFP(714)Rbt

<400> SEQUENCE: 56
taaatagcta gtttacttgt acagctcgtc catgc                                35

<210> SEQ ID NO 57
<211> LENGTH: 28
<212> TYPE: DNA
<213> ORGANISM: Artificial sequence
<220> FEATURE:
<223> OTHER INFORMATION: D184(1200)F

<400> SEQUENCE: 57
cgccttctcc tggacgagta cgcattgg                                        28

<210> SEQ ID NO 58
<211> LENGTH: 21
<212> TYPE: DNA
<213> ORGANISM: Artificial sequence
<220> FEATURE:
<223> OTHER INFORMATION: D184(+1400)R

<400> SEQUENCE: 58
ccagagccct accggcacgc c                                               21

<210> SEQ ID NO 59
<211> LENGTH: 23
<212> TYPE: DNA
<213> ORGANISM: Artificial sequence
<220> FEATURE:
<223> OTHER INFORMATION: APCC(-1)R

<400> SEQUENCE: 59
ggtcaacgaa cgaagaaaca cag                                             23

-continued

<210> SEQ ID NO 60
<211> LENGTH: 43
<212> TYPE: DNA
<213> ORGANISM: Artificial sequence
<220> FEATURE:
<223> OTHER INFORMATION: bT3'(+1)

<400> SEQUENCE: 60
taaactagct atttatctgg tacatatcat tcataagcac atg                          43

<210> SEQ ID NO 61
<211> LENGTH: 35
<212> TYPE: DNA
<213> ORGANISM: Artificial sequence
<220> FEATURE:
<223> OTHER INFORMATION: SecA(1)Fapcc

<400> SEQUENCE: 61
cttcgttcgt tgaccatgtt ccatgtgacg taccc                                   35

<210> SEQ ID NO 62
<211> LENGTH: 90
<212> TYPE: DNA
<213> ORGANISM: Artificial sequence
<220> FEATURE:
<223> OTHER INFORMATION: SecA(390)R-linker-ha

<400> SEQUENCE: 62
atcgtatggg tacatcccgg tgaacagctc ctcgcccttg ctcataccac cacctccgcc        60
acctctgagt tcatcgcttt tgagttgttc                                         90

<210> SEQ ID NO 63
<211> LENGTH: 32
<212> TYPE: DNA
<213> ORGANISM: Artificial sequence
<220> FEATURE:
<223> OTHER INFORMATION: HA(1)F

<400> SEQUENCE: 63
atgtacccat acgatgttcc tgactatgcg gg                                      32

<210> SEQ ID NO 64
<211> LENGTH: 32
<212> TYPE: DNA
<213> ORGANISM: Artificial sequence
<220> FEATURE:
<223> OTHER INFORMATION: HA(90)R

<400> SEQUENCE: 64
agcgtaatct ggaacgtcat aagggtatcc tg                                      32

<210> SEQ ID NO 65
<211> LENGTH: 37
<212> TYPE: DNA
<213> ORGANISM: Artificial sequence
<220> FEATURE:
<223> OTHER INFORMATION: GP(1)Fha

<400> SEQUENCE: 65
gttccagatt acgctatggt tccacaagca ctgttgc                                 37

<210> SEQ ID NO 66
<211> LENGTH: 69
<212> TYPE: DNA
<213> ORGANISM: Artificial sequence -continued

```
<220> FEATURE:
<223> OTHER INFORMATION: Co1-GP(1680)Rbt

<400> SEQUENCE: 66
taaatagcta gtttatggga gcggcgagcg cgccggcagc tggtggaagc taaggcctgt          60
ttcgccacc                                                                  69
```

DRUG DELIVERY COMPOSITION

CROSS-REFERENCE TO RELATED PATENT APPLICATION

This application claims priority to Japanese Patent Application No. 2019-069029, filed Mar. 29, 2019, the content of which is incorporated herein by reference.

FIELD OF THE INVENTION

The present invention relates to a drug delivery composition. In addition, the present invention relates to an acid-resistant cell and a drug carrier, which can be used in the drug delivery composition, and a method of producing the acid-resistant cell.

BACKGROUND OF THE INVENTION

In animals such as humans, which have a digestive tract, what is fed from the mouth is sent to the stomach through the esophagus. For example, in oral administration of a drug, there is a high possibility of the drug being enzymatically degraded in the stomach, particularly in a case where the drug contains a peptide or a protein as the main component. In addition, since the inside of the stomach is strongly acidic, there is a concern of even a low molecular weight compound drug being non-enzymatically degraded in the stomach. Moreover, even in a case where an acidic compound is desired to be absorbed in the intestine, it may be absorbed in the stomach. For this reason, oral administration using a capsule that does not dissolve in the stomach but dissolves in the intestine is useful.

As methods of realizing the delivery of a drug to the intestine, a technique called bilosome (Non Patent Document 1) utilizing a property that stability in the stomach is obtained in a case where a protein B is introduced into a lipid, a rice vaccine (Non Patent Document 2) utilizing the fact that a protein body that is a rice organelle exhibits resistance to a digestive enzyme, and a spore vaccine utilizing a spore that is resistant to a digestive enzyme, a temperature change, a pH change, and the like (Non Patent Document 3) are known.

As a vaccine aimed at use as an industrial oral vaccine, a vaccine using yeast is known. For example, Patent Document 1 describes an oral vaccine in which an antigenic protein is expressed in the body of the yeast. Patent Document 1 shows that in the case of being freeze-dried, yeast cells are not digested in the stomach or the jejunum but are digested and degraded in the ileum; however, the release of the antigenic protein from the yeast depends on the function of a digestive enzyme in the small intestine. Patent Document 2 suggests transmucosal or oral administration of a yeast strain into which an exogenous gene is incorporated is to induce immunity; however, it also describes that the protein which is derived from the used yeast is also antigenic.

CITATION LIST

Patent Documents

Patent Document 1: PCT International Publication No. WO2006/028214.
Patent Document 2: Published Japanese Translation No. 2012-508697 of the PCT international Publication.

Non Patent Documents

Non Patent Document 1: Mann J F et al., Lipid vesicle size of an oral influenza vaccine delivery vehicle influences the Th1/Th2 bias in the immune response and protection against infection. Vaccine. 2009 Jun. 2; 27 (27): 3643 to 3649.
Non Patent Document 2: Nochi T et al., Rice-based mucosal vaccine as a global strategy for cold-chain- and needle-free vaccination. Proc Natl Acad Sci USA. 2007 Jun. 26; 104(26): 10986 to 10991.
Non Patent Document 3: Huang J M et al., Mucosal delivery of antigens using adsorption to bacterial spores. Vaccine. 2010 Jan. 22; 28(4): 1021 to 1030.

SUMMARY OF THE INVENTION

Technical Problem

In the livestock industry, in a case where an infectious disease occurs, it is difficult to control the spread of the infectious disease, and a large amount of livestock is sometimes slaughtered. Some infectious diseases are said to be preventable by intestinal immunity, and thus the development of a technique for establishing immunity against a pathogen in the intestinal tract of a livestock animal is an urgent issue. In addition, in a case where intestinal immunity is imparted, there is a possibility that other mucosal immunity and systemic immunity can also be imparted. As a result, there is a need for the development of an enteric composition that can be orally administered and delivered directly to the intestine. However, the techniques described in Non Patent Documents 1 to 3 have a problem in terms of cost in the case of being used in the livestock industry.

An object of the present invention is to provide a novel drug delivery composition with which a drug can be delivered to the intestine, an acid-resistant cell and a drug carrier, which can be used in the drug delivery composition, and a method of producing the acid-resistant cell.

Solution to the Problem

The present invention includes the following aspects.
(1) A drug delivery composition containing an acid-resistant cell that encloses a drug.
(2) The drug delivery composition according to (1), in which the drug is localized in a sac-shaped membrane structure included in the acid-resistant cell.
(3) The drug delivery composition according to (2), in which the sac-shaped membrane structure is at least one selected from the group consisting of an exogenous liposome and an organelle.
(4) The drug delivery composition according to (3), in which the organelle is at least one selected from the group consisting of a mitochondrion, a chloroplast, an endoplasmic reticulum, a vacuole, a cell nucleus, a peroxisome, and a Golgi apparatus.
(5) The drug delivery composition according to any one of (1) to (4), in which the drug is at least one selected from the group consisting of a low molecular weight compound, a peptide, a protein, and a nucleic acid.
(6) The drug delivery composition according to any one of (1) to (5), in which the drug is a drug that acts in an intestine.
(7) The drug delivery composition according to any one of (1) to (6), in which the drug is a drug that has immunogenicity.

(8) The drug delivery composition according to any one of (1) to (7), in which the acid-resistant cell is a cell in which cell rupture is caused at pH 7 or higher.

(9) The drug delivery composition according to any one of (1) to (8), in which the acid-resistant cell is a cell that is resistant to acidic conditions of pH 1 to 3.

(10) The drug delivery composition according to any one of (1) to (9), in which the acid-resistant cell is a cell of algae that belong to the class Cyanidiophyceae.

(11) A feed containing the drug delivery composition according to any one of (1) to (10).

(12) A pharmaceutical product containing the drug delivery composition according to any one of (1) to (10).

(13) A food containing the drug delivery composition according to any one of (1) to (10).

(14) An acid-resistant cell that encloses a drug inside the cell.

(15) The acid-resistant cell according to (14), in which the drug is localized in a sac-shaped membrane structure included in the acid-resistant cell.

(16) The acid-resistant cell according to (14), in which the drug is localized outside the sac-shaped membrane structure included in the acid-resistant cell.

(17) The acid-resistant cell according to any one of (14) to (16), in which the drug is at least one selected from the group consisting of a low molecular weight compound, a peptide, a protein, and a nucleic acid.

(18) A method of producing the acid-resistant cell according to (15), the method including a step of introducing into the acid-resistant cell a gene encoding a fusion protein that contains a peptide or protein as a drug and contains a peptide or protein localizable to a cell membrane or an organelle.

In addition, the present invention also includes the following aspects.

(19) A drug carrier containing an acid-resistant cell.

(20) The drug carrier according to (19), in which the acid-resistant cell is a cell in which cell rupture is caused at pH 7 or higher.

(21) The drug carrier according to (19) or (20), in which the acid-resistant cell is a cell that is resistant to acidic conditions of pH 1 to 3.

(22) The drug carrier according to any one of (19) to (21), in which the acid-resistant cell is a cell of algae that belong to the class Cyanidiophyceae.

(23) A drug capsule obtained by encapsulating a drug in the drug carrier according to any one of (19) to (22).

(24) The drug carrier according to (23), in which the drug is localized in a sac-shaped membrane structure included in the acid-resistant cell.

In addition, the present invention also includes the following aspects.

(25) An acid-resistant cell containing an exogenous substance.

(26) The acid-resistant cell according to (25), in which the exogenous substance is localized in a sac-shaped membrane structure included in the acid-resistant cell.

(27) The acid-resistant cell according to (25) or (26), in which the exogenous substance is at least one selected from the group consisting of a low molecular weight compound, a peptide, a protein, a nucleic acid, and a synthetic high molecular weight compound.

(28) The acid-resistant cell according to any one of (25) to (27), in which the exogenous substance is a substance that acts in an intestine.

(29) The acid-resistant cell according to any one of (25) to (28), in which the exogenous substance is a substance that has immunogenicity.

(30) The acid-resistant cell according to any one of (26) to (29), in which the sac-shaped membrane structure is at least one selected from the group consisting of an exogenous liposome, a cell membrane, and an organelle.

(31) The acid-resistant cell according to (30), in which the organelle is at least one selected from the group consisting of a mitochondrion, a chloroplast, an endoplasmic reticulum, a vacuole, a cell nucleus, a peroxisome, and a Golgi apparatus.

(32) The acid-resistant cell according to any one of (25) to (31), in which the acid-resistant cell is a cell in which cell rupture is caused at pH 7 or higher.

(33) The acid-resistant cell according to any one of (25) to (32), in which the acid-resistant cell is a cell that is resistant to acidic conditions of pH 1 to 3.

(34) The acid-resistant cell according to any one of (25) to (33), in which the acid-resistant cell is a cell of algae that belong to the class Cyanidiophyceae.

(35) A feed containing the acid-resistant cell according to any one of (25) to (34).

(36) A pharmaceutical product containing the acid-resistant cell according to any one of (25) to (34).

(37) A food containing the acid-resistant cell according to any one of (25) to (34).

(38) A method of administering the exogenous substance, including orally administering the acid-resistant cell according to any one of (25) to (34) to a subject.

(39) A method of rearing an animal, including feeding an animal with the acid-resistant cell according to any one of (25) to (34).

(40) A method of imparting intestinal immunity, including orally administering the acid-resistant cell according to any one of (25) to (34).

Advantageous Effects of the Invention

According to the present invention, it is possible to provide a novel drug delivery composition with which a drug can be delivered to the intestine, an acid-resistant cell and a drug carrier, which can be used in the drug delivery composition, and a method of producing the acid-resistant cell.

DETAILED DESCRIPTION OF THE INVENTION

Definitions

Figure 1:
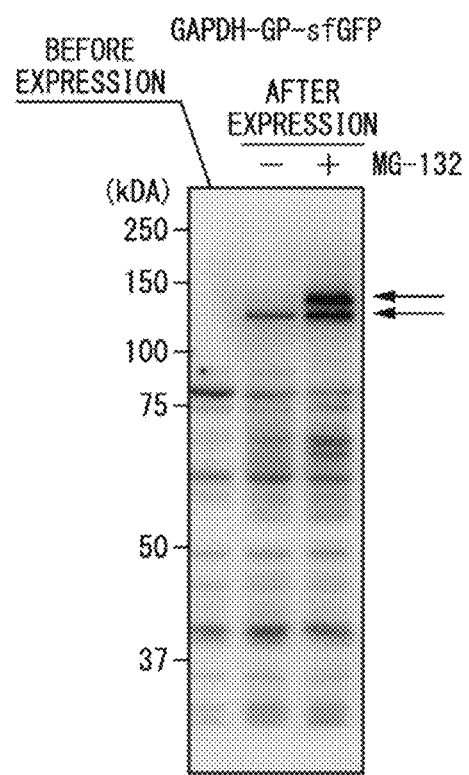
FIG. 1 is a figure showing a result of immunoblotting using an anti-GFP antibody in a GAPDH-GP-sfGFP expressing strain cultured in the presence and absence of MG-132. In the figure, arrowheads indicate bands of a GAPDH-GP-sfGFP protein.

In the present specification, the terms "peptide" and "protein" are used interchangeably and refer to polymers of amino acids bonded by an amide bond. The "peptide" or the "protein" may be a polymer of natural amino acids, may be a polymer of natural amino acids and unnatural amino acids (a chemical analog, a modified derivative, or the like of a natural amino acid), or may be a polymer of unnatural amino acids. Unless otherwise specified, an amino acid sequence is described from the N-terminal side toward the C-terminal side.

The number of amino acid residues constituting the "peptide" or the "protein" is not particularly limited, and amino acid polymers having two or more amino acid residues are included as the "peptide" or the "protein". In the present specification, unless otherwise specified, one having a large number of amino acid residues (for example, 100 amino acid residues or more) is described as a "protein", and one having a small number of amino acid residues (for example, less than 100 amino acids) is described as a "peptide".

In the present specification, the terms "polynucleotide" and "nucleic acid" are used interchangeably and refer to nucleotide polymers in which nucleotides are bonded by a phosphodiester bond. The "polynucleotide" and the "nucleic acid" may be DNA or RNA, or may be composed of a combination of DNA and RNA. In addition, the "polynucleotide" or the "nucleic acid" may be a polymer of natural nucleotides, may be a polymer of natural nucleotides and unnatural nucleotides (an analog of a natural nucleotide) or a nucleotide (for example, a phosphorothioate skeleton) in which at least one moiety of a base moiety, a sugar moiety, and a phosphate moiety of a natural nucleotide is modified, or may be a polymer of an unnatural nucleotide. Unless otherwise specified, the nucleotide sequence is described from the 5' side toward the 3' side.

In the present specification, the term "gene" refers to a polynucleotide containing at least one open reading frame encoding a specific protein. The gene can contain both an exon and an intron.

In the present specification, the term "operably linked" that is used for a polynucleotide refers to a state where a first nucleotide sequence is located sufficiently close to a second nucleotide sequence and thus the first nucleotide sequence can influence a region that is under the regulation of the second nucleotide sequence or the second nucleotide sequence. For example, the description that a polynucleotide is "operably linked to a promoter" means that the polynucleotide is linked to be expressed under the regulation of the promoter.

In the present specification, the description "a promoter may function" means that the promoter can express a polynucleotide operably linked to the promoter in a target cell.

In the present specification, "expressible state" means a state in which a polynucleotide or a gene can be transcribed in a cell into which the polynucleotide has been introduced.

In the present specification, "expression vector" means a vector containing a target polynucleotide, which includes a system for making a target polynucleotide be in an expressible state in a cell into which the vector has been introduced.

In the present specification, "drug delivery composition" means a composition that is used to deliver a drug to any site (an organ, an organum, a tissue, a disease site, or the like) in a living body.

In the present specification, "drug carrier" means a carrier that is used to deliver a drug. The drug carrier may be any one of an organic substance or an inorganic substance. In a case where a drug carrier is composed of an organic substance, the drug carrier may be a cell.

In the present specification, the description that a cell "encloses a drug" means that the drug is present in the cell and/or the drug is present in the cell membrane. In a case where the drug is present in the cell, the drug may be present inside an organelle.

In the present specification, the description that a drug is "localized in a sac-shaped membrane structure" means that most of the drug is present inside the target sac-shaped membrane structure (inside a sac) or in a membrane (hereinafter referred to as "sac-shaped membrane") that forms the sac-shaped membrane structure. In a case where a drug is localized in a sac-shaped membrane structure included in a cell, it is not necessary for the entire drug enclosed in the cell to be present inside the sac-shaped membrane structure or in the sac-shaped membrane, and a part of the drug may be present outside the sac-shaped membrane structure. In a case where a drug is "localized in a sac-shaped membrane structure", the proportion of the drug present in the sac-shaped structure can be, for example, 50% or more of the total amount of the drug enclosed in the cell and is preferably 60% or more, more preferably 70% or more, and still more preferably 80% or more.

In the present specification, "low molecular weight compound" means a compound having a molecular weight of about 2,000 or less. However, a peptide and a nucleic acid, which have a molecular weight of 2,000 or less, are not included as "low molecular weight compounds".

In the present specification, "synthetic high molecular weight compound" means an unnatural compound having a molecular weight of 2,000 or more. "Unnatural compound" means a compound that is not present in nature. Examples of the synthetic high molecular weight compound include various synthetic polymers (polyolefins, polyesters, polyamides, polyethylene glycol, poly(2-oxazoline), and the like). An artificially chemically synthesized peptide, a protein, and a nucleic acid are not included as "synthetic high molecular weight compounds".

In the present specification, "exogenous substance" means a substance that is introduced from outside a cell or a substance produced in a cell from a substance that is introduced from outside the cell. Specific examples of the substance produced in a cell from a substance that is introduced from outside the cell include a transcript (an mRNA) and a translation product (a protein) of a foreign gene in a cell into which the foreign gene has been introduced; and an active metabolite (a drug that exhibits a desired medicinal effect) of a prodrug, in a cell into which the prodrug has been introduced. The exogenous substance is a substance different from the substance that is originally included in a cell (an endogenous substance).

In the present specification, "drug" means a substance that exhibits a beneficial activity in a living body. The beneficial activity exhibited by a drug is not particularly limited and includes a physiological activity, a pharmacological activity, a biological activity, a chemical activity useful for diagnosis, and the like. For example, the activity may include a pharmacological activity possessed by a compound known as an active component of a pharmaceutical product, and a chemical activity or a physiological activity possessed by a diagnostic agent administered to and used in the body. Examples of the activity include, but are not limited to, an immunity inducible activity, an immunostimulatory activity, an anti-cancer activity, a signal transduction inhibitory activity, a signal transduction promoting activity, an anti-metabolic activity, an analgesic activity, an anti-inflammatory activity, a bactericidal activity, an anti-viral activity, an anti-allergic activity, an enzyme inhibitory activity, a contrasting action, and a fluorescent activity. The drug may be a compound (a so-called prodrug) that releases a compound that exhibits beneficial activity in the living body.

In the present specification, the description "pharmaceutical product" includes a pharmaceutical product for medical application and a medicine in a broad sense taken for the treatment or prevention of a disease or for the promotion of health. It does not matter whether the "pharmaceutical product" is officially registered or not or whether the "pharmaceutical product" is used for medical application or for non-medical application.

In the present specification, "food" is used as a concept that includes general foods, health foods, nutritional supplementary foods, health supplementary foods, functional foods, beauty supplementary foods, supplements, and the like.

In the present specification, "mutant strain" means a cell strain in which the genome (including the nuclear genome, the chloroplast genome, and the mitochondrial genome; the same applies hereinafter) of an original cell strain is spontaneously or artificially mutated. An artificial method of causing a mutation in the genome is not particularly limited. Examples of the artificial method include ultraviolet irradiation, irradiation, chemical treatment with nitrous acid or the like, and a genetic engineering method such as gene translocation or genome editing.

In the present specification, "mutant strain of a YFU3 strain" refers to an algal strain in which the genome of the YFU3 strain is mutated, where the algal strain has a diploid cell morphology and a haploid cell morphology. "Mutant strain of an HKN1 strain" refers to an algal strain in which the genome of the HKN1 strain is mutated, where the algal strain has a diploid cell morphology and a haploid cell morphology.

In the present specification, "related species" refers to, for example, a cell strain in which the nucleotide sequence of the rbcL gene, the 18S rRNA gene, or the 16s RNA gene has 90% or more identity with the nucleotide sequence of the above gene of the original species. In a case where the species is an alga, the above target gene to be compared is preferably the rbcL gene or the 18S rRNA gene and is more preferably the rbcL gene. The identity of the nucleotide sequence between the rbcL gene of the original alga and the nucleotide sequence of the rbcL gene of the related algal species is preferably 95% or more, more preferably 97% or more, still more preferably 98% or more, and particularly preferably 99% or more. The nucleotide sequence of the rbcL gene possessed by algae can be obtained by a known method. For example, DNA is extracted from a target algal cell by a known method, a DNA fragment of the rbcL gene is amplified by a PCR method or the like, and the nucleotide sequence of the amplified DNA fragment is analyzed by a DNA sequencer, whereby the nucleotide sequence of the rbcL gene of the target alga can be obtained.

Drug Delivery Composition

In one embodiment, the present invention provides a drug delivery composition containing an acid-resistant cell that encloses a drug. In a preferred embodiment, the drug is localized in a sac-shaped membrane structure included in the acid-resistant cell.

Acid-Resistant Cell

In the present specification, "acid-resistant cell" means a cell that is resistant to acidic conditions. Specific examples of the acidic conditions include a pH condition of pH 1 to 3. The acid-resistant cell is preferably resistant to a pH condition of pH 1 to 4 and is more preferably resistant to a pH condition of pH 1 to 5.

The description "resistant" to acidic conditions means that cell rupture does not occur under acidic conditions and thus the elution of cell contents does not occur.

The acid-resistant cell may be a live cell or a dead cell; however, it is preferable that the cell morphology be maintained. It is preferable that the acid-resistant cell be a cell in which the cell membrane and/or the outer membrane thereof is not damaged and the cell contents are not eluted. In a case where the acid-resistant cell is a live cell, the cell can grow under acidic conditions.

The kind of the acid-resistant cell is not particularly limited. Examples of the acid-resistant cell include an acid-resistant algal cell. Preferred examples of such algal cells include a microalgal cell that is isolated from an acidic environment such as an acidic hot spring. Specific examples of such microalgae include algae that belong to the class Cyanidiophyceae.

Figure 7:
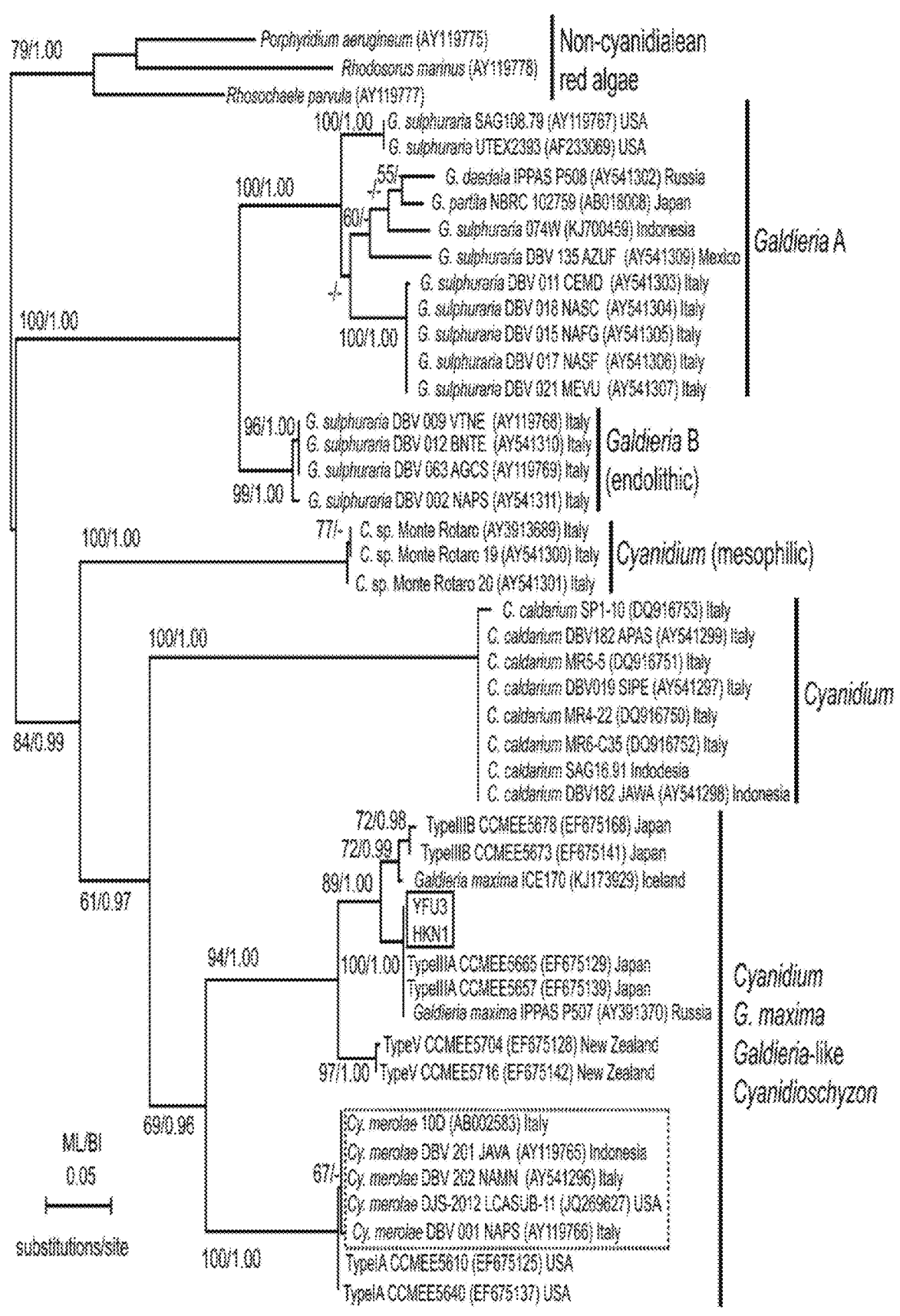
FIG. 7 shows a molecular phylogenetic tree of algae that belong to the class Cyanidiophyceae based on the chloroplast ribulose 1,5-bisphosphate carboxylase/oxygenase large subunit gene. The local bootstrap value according to the maximum likelihood method (only 50 or more is described, left) and the posterior probability according to the Bayes method (only 0.95 or more is described, right) are shown in the vicinity of each branch. The known *Cyanidioschyzon merolae* is surrounded by a dotted line, and a YFU3 strain and an HKN1 strain are surrounded by a solid line.

The class Cyanidiophyceae are taxonomically classified into the phylum Rhodophyta and the class Cyanidiophyceae. The class Cyanidiophyceae are currently classified into three genera: the genus *Cyanidioschyzon*, the genus *Cyanidium*, and the genus *Galdieria*. The acid-resistant cell may be algae that belong to any of these genera. Whether or not a certain alga belongs to the class Cyanidiophyceae can be determined by, for example, carrying out a phylogenetic analysis using the nucleotide sequence of the 18S rRNA gene or the chloroplast ribulose 1,5-bisphosphate carboxylase/oxygenase large subunit (rbcL) gene. The phylogenetic analysis may be carried out by a known method. A molecular phylogenetic tree based on the nucleotide sequence of the rbcL gene of algae that belong to the class Cyanidiophyceae is shown in FIG. 7.

Some algae that belong to the class Cyanidiophyceae have both diploid and haploid cell morphology. Haploid cell morphology can result from meiosis of the diploid cell morphology. Then, two haploid cells are considered to be conjugated to generate a diploid cell.

In the haploid cell, it is easy to prepare a transformant using the gene recombination technique as compared with the diploid cell. For this reason, as will be described later, in a case where a gene encoding a peptide as a drug is introduced into an acid-resistant cell, a haploid cell can be preferably used. In addition, in a case where a plurality of transformants into which any drug-encoding gene has been introduced are prepared using a haploid cell and these transformants are mated with each other, it is possible to prepare a diploid cell in which a plurality of drug-encoding genes are combined and a plurality of drugs are enclosed.

Whether the algae are diploid or haploid can be determined by checking the copy number of the same genetic locus. That is, in a case where the copy number of the same genetic locus is 1, it is determined to be a haploid. It is also possible to determine that the algae are haploid by using a next-generation sequencer or the like. For example, sequence reads of the entire genome are acquired by a next-generation sequencer or the like, the sequence reads are assembled, and then the sequence reads are mapped on the sequence obtained by the assembling. In the diploid, differences in nucleotides for each allele can be found in various regions on the genome; however, in the haploid, such a region cannot be found since only one allele is present.

Alternatively, cells are stained with a nuclear staining reagent such as DAPI and compared with a cell known to be haploid, and then the determination may be made in such a manner that a cell exhibiting the same fluorescence brightness as the haploid cell is determined to be haploid or a cell exhibiting about twice the fluorescence brightness of the haploid cell is determined to be diploid. Alternatively, cells are stained with a nuclear staining reagent such as DAPI and compared with a cell known to be diploid, and then the determination may be made in such a manner that a cell exhibiting the same fluorescence brightness as the diploid cell is determined to be diploid or a cell exhibiting about half the fluorescence brightness of the diploid cell is determined to be haploid.

The acid-resistant cell preferably has no strong cell wall in order to rapidly release a drug in the intestine. In the present specification, the description "have no strong cell wall" means that cell rupture occurs in any of the following cell rupture treatments (A) to (C).

(A) Cells are suspended in an isotonic solution having a pH of 7 or higher and left to stand for 1 week or longer.

(B) Cells are suspended in distilled water and left to stand for 1 minute or longer.

(C) Cells are subjected to drying treatment and suspended in an isotonic solution having a pH of 7 or higher.

In the above (A) to (C), in a case where the cells are cultured cells, the medium may be removed by centrifugation or the like and the algal cells may be washed with an isotonic solution or the like before each treatment.

In the above (A) and (C), examples of the isotonic solution include a pH 7 buffer solution containing 10% sucrose and 20 mM HEPES.

In the above (C), examples of the drying treatment include drying in a refrigerator (4° C.) and freeze-drying. In the drying treatment, a precipitate of algal cells collected by centrifugation is used. In the case of drying in a refrigerator, the drying treatment time depends on the quantity of cells; however, examples thereof include 3 days or more.

Whether or not cell rupture has occurred can be determined by centrifuging (1,500×g, 3 minutes) the cell suspension after the cell rupture treatment of the above (A) to (C) and determining the proportion of the amount of protein in the centrifugation supernatant to the total amount of protein in the cell suspension. Specifically, in a case where the rupture rate determined by the following expression is 20% or more, it can be determined that cell rupture has occurred.

$$\text{Rupture rate} = \frac{\text{Protein mass in centrifugation supernatant (mass, g)}}{\text{Total protein mass in cell suspension (mass, g)}} \times 100(\%) \quad (1)$$

Alternatively, cells in the cell suspension are observed with an optical microscope (for example, at a magnification of 600 times), and in a case where the proportion of cells that have undergone cell rupture is about 10% or more and preferably about 20% or more of the whole cells, it may be determined that cell rupture has occurred.

In a case where a cell does not have a strong cell wall, the cell wall is usually not observed by observation with an optical microscope (for example, at a magnification of 600 times). Whether or not cell rupture occurs in a mild hypotonic treatment under the condition of pH 6 or less does not affect the determination of whether or not the algae do not have a strong cell wall.

In the cell rupture treatment of the above (A) and (C), an isotonic solution having a pH of 7 or higher can be used, and thus it can be said that cells in which cell rupture occurs in the cell rupture treatment of any of the above (A) and (C) are cells that undergo cell rupture under the condition of pH 7 or higher. The acid-resistant cell is preferably a cell in which cell rupture occurs at pH 7 or higher in order to rapidly release a drug in the intestine.

Whether or not cells are the cells that rupture under the condition of pH 7 or higher can be determined by immersing the cells in a buffer solution having a pH of 7 or higher and observing for about 10 to 30 minutes to check whether or not the algal cells rupture.

Among the algae that belong to the class Cyanidiophyceae, examples of the acid-resistant cell having the above-described characteristics include *Cyanidioschyzon merolae*, a haploid of algae that belong to the genus *Galdieria*, and a haploid of algae that belong to the genus *Cyanidium*. These algae may be isolated from an acidic environment such as an acidic hot spring or may be obtained from a culture collection or the like. Examples of such a culture collection include Microbial Culture Collection at the National Institute for Environmental Studies (16-2 Onogawa, Tsukuba City, Ibaraki Prefecture, Japan) and the American Type Culture Collection (ATCC; 10801 University Boulevard Manassas, VA 20110 USA).

Examples of the haploid of algae that belong to the genus *Galdieria* include haploids of *Galdieria sulphuraria* and *Galdieria partita*, and haploids of related species, mutant strains, progeny, and the like thereof. For example, a diploid of algae that belong to the genus *Galdieria*, which is obtained from the culture collection or the like, is cultured until the quiescent phase is reached, and then the culture is continued for any period, whereby haploid cells appear in the culture solution. The haploid cells may be collected and used as acid-resistant cells.

Examples of the haploid of algae that belong to the genus *Cyanidium* include a haploid of a *Cyanidium* sp. YFU3 strain (FERM BP-22334) (hereinafter referred to as a "YFU3 strain"), a haploid of a *Cyanidium* sp. HKN1 strain (FERM BP-22333) (hereinafter referred to as an "HKN1 strain"), and related species, mutant strains, progeny, and the like thereof.

The YFU3 strain (a haploid) is a unicellular red alga isolated from high-temperature acidic water in a hot spring in Yufu City, Oita Prefecture, Japan. The YFU3 strain was deposited on May 30, 2017, at the Patent Microorganisms Depositary Center, the National Institute of Technology and Evaluation (2-5-8 Kazusakamatari, Kisarazu City, Chiba Prefecture, Japan) under the deposit number FERM P-22334, and then was transferred to the international deposit on Apr. 20, 2018 under the deposit number FERM BP-22334.

The HKN1 strain is a unicellular red alga isolated from high-temperature acidic water in a hot spring in Hakone-machi, Ashigarashimo-gun, Kanagawa Prefecture, Japan. The HKN strain (a haploid) was deposited on May 30, 2017, at the Patent Microorganisms Depositary Center, the National Institute of Technology and Evaluation under the deposit number FERM P-22333, and then was transferred to the international deposit on Apr. 20, 2018, under the deposit number FERM BP-22333.

The algae that belong to the class Cyanidiophyceae can be cultured using a medium for culturing microalgae. The medium is not particularly limited; however, examples thereof include an inorganic salt medium containing a nitrogen source, a phosphorus source, and trace elements (zinc, boron, cobalt, copper, manganese, molybdenum, iron, and the like). Examples of the nitrogen source include an ammonium salt, a nitrate, a nitrite, urea, and amines, and examples of the phosphorus source include a phosphate. Examples of such a medium include a 2×Allen medium (Allen M B. Arch. Microbiol. 1959, 32: 270 to 277.), an M-Allen medium (Minoda A et al. Plant Cell Physiol. 2004, 45: 667 to 671), and an MA2 medium (Ohnuma M et al. Plant Cell Physiol. 2008, January; 49 (1): 117 to 120.).

The algae that belong to the class Cyanidiophyceae can also be cultured in a medium using acidic hot spring waste water. "Acidic hot spring waste water" means acidic waste water discharged from a hot spring facility. The acidic hot spring waste water is not particularly limited; however, it preferably has a pH of 1.0 to 4.0 and more preferably a pH of 1.0 to 3.0. "Medium using acidic hot spring waste water" means a medium prepared by adding a nitrogen source, a phosphorus source, trace elements, and the like to the acidic hot spring waste water. The medium using acidic hot spring waste water is preferably a medium in which a nitrogen source is added to the acidic hot spring waste water and more preferably a medium in which a nitrogen source and a phosphorus source are added (for example, see Hirooka S and Miyagishima S. Y. (2016) Cultivation of Acidophilic Algae *Galdieria sulphuraria* and *Pseudochlorella* sp. YKT1 in Media Derived from Acidic Hot Springs. Front Microbiol. December 20; 7: 2022). Examples of the nitrogen source include an ammonium salt (ammonium sulfate or the like), urea, and a nitrate (sodium nitrate or the like); however, an ammonium salt or urea is preferable, and an ammonium salt is more preferable. Examples of the amount of the nitrogen source to be added include 1 to 50 mM in terms of the amount of nitrogen to be added. The amount of the nitrogen source to be added is preferably 5 to 40 mM and more preferably 10 to 30 mM in terms of the amount of nitrogen to be added. Examples of the phosphorus source include a phosphate (potassium dihydrogen phosphate or the like). The amount of phosphorus source to be added can be 0.1 to 10 mM in terms of the amount of phosphorus to be added, and the amount of phosphorus source to be added is preferably 0.5 to 5 mM and more preferably 1 to 3 mM. Since the algae that belong to the class Cyanidiophyceae can be cultured in a medium using acidic hot spring waste water, the acidic hot spring waste water can be effectively used and culture can be carried out at a low cost.

In a case where the algae that belong to the class Cyanidiophyceae are algae that belong to the genus *Galdieria*, the above-described nitrogen source is preferably an ammonium salt or urea and is more preferably an ammonium salt. In a case where the algae that belong to the class Cyanidiophyceae are algae that belong to the genus *Cyanidium*, the above-described nitrogen source is preferably an ammonium salt or a nitrate, and more preferably an ammonium salt.

As described above, the algae that belong to the class Cyanidiophyceae can be proliferated at a high density under a relatively wide range of culture conditions. Examples of the pH condition include pH 1.0 to 6.0, and pH 1.0 to 5.0 is preferable. In the case of culturing outdoors, it is preferable to carry out culture under the conditions of high acidity in order to prevent the proliferation of other organisms, and examples of such conditions include pH 1.0 to 3.0.

Examples of the temperature condition include 15° C. to 50° C., and 30° C. to 50° C. is preferable. In the case of culturing outdoors, it is preferable to culture at a high temperature in order to prevent the proliferation of other organisms, and examples of such conditions include 35° C. to 50° C.

Examples of the light intensity include 5 to 2,000 μmol/m$^2$s, and 5 to 1,500 μmol/m$^2$s is preferable. In the case of culturing outdoors, culture can be carried out in sunlight. In the case of culturing indoors, culture can be carried out in continuous light, or a light-dark cycle (10 L:14 D, and the like) may be provided.

Drug

The drug enclosed in the acid-resistant cell is not particularly limited and may be any drug. Examples of the drug include, but are not limited to, a low molecular weight compound, a peptide, a protein, a nucleic acid, a lipid, a sugar, a vitamin, a hormone, and a synthetic high molecular weight compound. Among these, the drug is preferably at least one drug selected from the group consisting of a low molecular weight compound, a peptide, a protein, and a nucleic acid.

As the low molecular weight compound, a low molecular weight compound known as an active component of a pharmaceutical product can be used without particular limitation. The low molecular weight compound may be a contrast agent, a fluorescent dye, or the like, which is used as a diagnostic agent. Examples of the low molecular weight compound include, but are not limited to, an immunostimulator, an anti-cancer agent, a signal transduction inhibitor, an antimetabolite, an analgesic, an anti-inflammatory agent, an antibiotic, an anti-allergic agent, a therapeutic agent for a central nervous system disease, a therapeutic agent for a circulatory organ disease, a therapeutic agent for a respiratory organ system disease, a therapeutic agent for a digestive organ system disease, a therapeutic agent for a urogenital organ disease, a contrast agent, and a fluorescent dye. The low molecular weight compound is not limited to an active component of a pharmaceutical product and may be a component (for example, a nutritional component such as an amino acid or a vitamin) in a food or a food additive (such as a flavoring agent).

Examples of the nucleic acid include nucleic acid molecules that are used as nucleic acid medicines (siRNA, miRNA, antisense RNA, an aptamer, a decoy, a CpG oligonucleic acid, and the like).

Examples of the synthetic high molecular weight compound include industrially produced high molecular weight compounds such as polyolefins, polyesters, and polyamides, which are granular or spherical. Some of these are expected to have an immunostimulatory action.

The drug may be a microcapsule containing a low molecular weight compound, where the microcapsule may be a sustained release microcapsule or a microcapsule that releases a drug in a manner dependent on the environment such as temperature, pH, or pressure.

As the peptide or the protein (hereinafter, also collectively referred to as the "drug peptide"), a peptide or a protein known as an active component of a pharmaceutical product can be used without particular limitation. Examples of the drug peptide include, but are not limited to, an antigen, a cytokine, a growth factor, a hormone, an enzyme, an antibody, an antibody fragment, a ligand, and a blood component protein.

Among them, the drug peptide is preferably one that has immunogenicity. The description that the drug peptide has "immunogenicity" means that it induces immunity to the drug peptide in the living body to which the drug peptide is administered. The immunity induced by the drug peptide may be cell-mediated immunity, humoral immunity, or both.

The drug peptide more preferably contributes to intestinal immunity. "Intestinal immunity" means a biological defense system for preventing the invasion of foreign substances from the intestinal tract into the body. The intestinal immune system is composed of lymphoid tissues such as Peyer's patch, immunocompetent cells of the lamina propria mucosae, intestinal tract epithelial cells, and lymphocytes present between the intestinal tract epithelial cells. A drug peptide that contributes to intestinal immunity can act on any one or more of these intestinal immune system constituents to strengthen the intestinal immune system.

Examples of the drug peptide that contribute to intestinal immunity include an immunogenic peptide or an immunogenic protein of pathogenic microorganisms or pathogenic viruses (hereinafter, collectively referred to as a "pathogen"). The immunogenic drug peptide can be appropriately selected depending on the infectious disease which affects a subject to which the drug delivery composition of the present embodiment is applied. The immunogenic peptide or the immunogenic protein is also referred to as an antigenic peptide or antigenic protein.

For example, in a case where the drug delivery composition of the present embodiment is applied to a human, an immunogenic peptide or immunogenic protein of a human pathogen can be used as the drug peptide. Examples of the human pathogen include, but are not limited to, rabies virus, rotavirus, influenza virus, AIDS virus, poliovirus, hepatitis A virus, hepatitis B virus, human papillomavirus, cholera vibrio, salmonella, tubercule bacillus, *Streptococcus pneumoniae*, anthrax bacillus, and Salmonella typhi.

For example, in a case where the drug delivery composition of the present embodiment is applied to livestock, an immunogenic peptide or immunogenic protein of a pathogen of the livestock can be used as the drug peptide. Examples of the livestock pathogen include, but are not limited to, rabies virus, bovine rotavirus, bovine corona virus, Akabane virus, bovine adenovirus, bovine parainfluenza virus, bovine salmonella, tubercule bacillus, porcine circovirus, porcine influenza virus, porcine parvovirus, porcine cholera vibrio, and porcine streptococcus.

The immunogenic peptide or the immunogenic protein can be designed using, for example, a full-length protein of a protein constituting the envelope or capsid of a pathogenic virus or a partial peptide thereof; or a full-length protein of a cell membrane protein of a pathogenic bacterium or a partial peptide thereof. For example, in a case where the pathogen is rabies virus, examples of the immunogenic protein include the full length of the glycoprotein (nucleotide sequence: SEQ ID NO: 1, amino acid sequence: SEQ ID NO: 2) or a partial peptide thereof.

Drug Localization to Sac-Shaped Membrane Structure

In cells of the acid-resistant cell, a drug is preferably localized in the sac-shaped membrane structure included in the acid-resistant cell. In the present specification, "sac-shaped membrane structure" means a structure partitioned in a sac shape by a biological membrane or a structure mimicking a biological membrane, and specific examples thereof include a cell membrane, an organelle, and an exogenous liposome. Examples of the organelle include, but are not limited to, a mitochondrion, a chloroplast, an endoplasmic reticulum, a vacuole, a cell nucleus, a peroxisome, and a Golgi apparatus. "Exogenous liposome" means a liposome that has been introduced into a cell from the outside.

In a case where a drug is localized in the sac-shaped membrane structure of the acid-resistant cell, it is possible to suppress the degradation of the drug by a degrading enzyme in the cytoplasm. As a result, the drug is protected from degradation by an enzyme in the cell until the acid-resistant cell is delivered to a predetermined site (for example, an intestine) in the body and the acid-resistant cell ruptures.

The method of localizing a drug in the sac-shaped membrane structure is not particularly limited; however, examples thereof include a method using a signal peptide (hereinafter referred to as a "translocation signal") that instructs the translocation to any sac-shaped structure or a protein (hereinafter referred to as a "translocation protein") that translocates to the corresponding sac-shaped structure. For example, in a case where a translocation signal or translocation protein that targets any sac-shaped structure is bound to a drug, and the drug is introduced into an acid-resistant cell, the drug can be localized in the corresponding sac-shaped structure. For example, in a case where a drug is localized in any one of a mitochondrion, a vacuole, a peroxisome, an endoplasmic reticulum, a cell membrane, a Golgi apparatus, or a cell nucleus, a translocation signal or translocation protein to a mitochondrion, a vacuole, a peroxisome, an endoplasmic reticulum, a cell membrane, a Golgi apparatus, or a cell nucleus can be bound to the drug. A translocation signal and a translocation protein can be selected from various known ones depending on the kind of the acid-resistant cell. Alternatively, a translocation signal or translocation protein to the corresponding sac-shaped membrane structure may be acquired by isolating a sac-shaped membrane structure, to which a drug is desired to be localized, from the acid-resistant cell with a cell fractionation method such as density gradient centrifugation and analyzing proteins in the sac-shaped membrane structure.

For example, in a case where *Cyanidioschyzon merolae* is used as the acid-resistant cell, the following can be used as the translocation signal or translocation protein, for example.

As the translocation protein to the chloroplast, it is possible to use a protein consisting of 130 residues on the N-terminal side (nucleotide sequence: SEQ ID NO: 5, amino acid sequence: SEQ ID NO: 6) of a chloroplast preprotein translocase SecA subunit (CMQ393C; nucleotide sequence: SEQ ID NO: 3, amino acid sequence: SEQ ID NO: 4) (Sumiya et al. 2016, Proc Natl Acad Sci USA. 113 (47): E7629-E7638; PMID: 27837024).

As the translocation signal to the mitochondrial matrix, it is possible to use a peptide consisting of 78 residues on the N-terminal side (nucleotide sequence: SEQ ID NO: 9, amino acid sequence: SEQ ID NO: 10) of EF-TU (CMS502C) (nucleotide sequence: SEQ ID NO: 7, amino acid sequence: SEQ ID NO: 8) (Imoto et al. 2013, BMJ. 300 (6735): 1316-1318; PMID: 2369666).

As the translocation protein to the vacuole, it is possible to use prenylated Rab acceptor PRA1 (CMJ260C) (base: SEQ ID NO: 7, amino acid sequence: SEQ ID NO: 8), ABC transporter (CMS401C) (nucleotide sequence: SEQ ID NO: 13, amino acid sequence: SEQ ID NO: 14), or o-methyl transferase (CMT369C) (nucleotide sequence: SEQ ID NO: 15, amino acid sequence: SEQ ID NO: 16), and the like (Yagisawa et al. 2009, Plant J. 60 (5): 882-893; PMID: 19709388).

As the translocation protein to the peroxisome, it is possible to use catalase (CMI050C) (nucleotide sequence: SEQ ID NO: 17, amino acid sequence: SEQ ID NO: 18) (Moriyama et al. 2014, Planta. 240 (3): 585-598; PMID: 25009310).

As the translocation protein to the endoplasmic reticulum, it is possible to use ACC1 (CMM188C) (nucleotide sequence: SEQ ID NO: 19, amino acid sequence: SEQ ID NO: 20), PAP (CMT239C) (nucleotide sequence: SEQ ID NO: 21, amino acid sequence: SEQ ID NO: 22), or ALA1 (CMR396C) (nucleotide sequence: SEQ ID NO: 23, amino acid sequence: SEQ ID NO: 24), (Mori et al. 2016, Front Plant Sci. 7: 958; PMID: 27446184).

As the translocation protein to the cell membrane, it is possible to use ALA1 (CMR396C) and the like (Mori et al. 2016, Front Plant Sci. 7: 958; PMID: 27446184). Since ALA1 (CMR396C) is also a translocation protein to the endoplasmic reticulum, a drug can be localized in both the cell membrane and the endoplasmic reticulum in a case of using ALA1 (CMR396C).

As the translocation protein to the Golgi apparatus, it is possible to use Got1 (CMI302C) (nucleotide sequence: SEQ ID NO: 25, amino acid sequence: SEQ ID NO: 26), and the like (Yagisawa et al. 2013, Protoplasma. 250 (4): 943 to 948; PMID: 23197134).

As the translocation protein to the cell nucleus, it is possible to use topoisomerase I type IB (CMM263C) (nucleotide sequence: SEQ ID NO: 27, amino acid sequence: SEQ ID NO: 28) and the like (Moriyama et al 2014, Genome Biol Evol. 6 (1): 228 to 237; PMID: 24407855).

In a case where the drug is a drug peptide, the drug peptide may be enclosed in the acid-resistant cell as a fusion protein with a translocation signal or a translocation protein. In a case where the drug peptide is made to be a fusion protein with a translocation signal or a translocation protein, the drug peptide can be localized in the sac-shaped membrane structure that is targeted by the corresponding translocation signal or the translocation protein.

For example, in a case where a gene (hereinafter, also referred to as a "fusion protein gene") encoding a fusion protein of a drug peptide and a translocation signal or a translocation protein is introduced into an acid-resistant cell, and the fusion protein is expressed in the acid-resistant cell, the fusion protein translocates to the sac-shaped membrane structure that is targeted by the translocation signal or the translocation protein. As a result, the drug peptide contained in the fusion protein is localized in the sac-shaped membrane structure. Accordingly, in a preferred embodiment, the acid-resistant cell is a cell into which a fusion protein gene encoding a fusion protein containing a translocation signal or translocation protein and a drug peptide is introduced in an expressible state and is a cell that has the fusion protein gene. In addition, in the preferred embodiment, the acid-resistant cell is a cell expressing the fusion protein gene.

The fusion protein gene may contain, in addition to the coding sequence of the drug peptide and the coding sequence of the translocation signal or translocation protein, a sequence encoding a peptide that enhances recognition by intestinal tract cells, and the like. Examples of the peptide that enhances recognition by intestinal tract cells include Co1 peptide (SEQ ID NO: 43) and the like.

The fusion protein gene of the drug peptide and the translocation signal or translocation protein is preferably operably linked to a promoter capable of functioning in the acid-resistant cell. The promoter is not particularly limited as long as it is capable of functioning in the acid-resistant cell; however, it is preferably a promoter of a housekeeping gene of which an expression level is high from the viewpoint of maintaining the amount of drug in the cells. For example, in a case where the acid-resistant cell is *Cyanidioschyzon merolae*, for example, the promoter of APCC (CMO250C) (for example, −600 to −1; where "−1" indicates the nucleotide immediately before the start codon), the promoter of CPCC (CMP166C), the promoter of catalase (CMI050C), or the like can be preferably used as a promoter. The promoter sequence of APCC of *Cyanidioschyzon merolae* is set forth in SEQ ID NO: 29, the promoter sequence of CPCC (CMP166C) of *Cyanidioschyzon merolae* is set forth in SEQ ID NO: 30, and the promoter sequence of catalase (CMI050C) of *Cyanidioschyzon merolae* is set forth in SEQ ID NO: 31. These promoters of *Cyanidioschyzon merolae* can also be used in other algae that belong to Cyanidiophyceae.

The gene encoding the above fusion protein is introduced into an acid-resistant cell in an expressible state, and for example, is introduced into an acid-resistant cell in the form of an expression vector. In addition to the fusion protein and the promoter, the expression vector may contain control sequences such as an enhancer, a poly A addition signal, a terminator, and 3' UTR, and marker genes such as a drug resistance gene. Examples of the terminator and 3' UTR include 3' UTR of β-tubulin.

The kind of vector is not particularly limited, and a commonly used expression vector can be appropriately selected and used depending on the kind of acid-resistant cell. The vector may be linear or circular, may be a non-viral vector such as a plasmid, may be a viral vector (for example, a retroviral vector such as a lentiviral vector), or may be a vector based on a transposon.

In a case where the acid-resistant cell is *Cyanidioschyzon merolae*, the URA5.3 gene (CMK046C) may be used as a selectable marker. *Cyanidioschyzon merolae* includes a *Cyanidioschyzon merolae* M4 strain, which is a uracil auxotrophic mutant strain (Minoda et al., Plant Cell Physiol. 2004 June; 45 (6): 667 to 671). The *Cyanidioschyzon merolae* M4 strain has a mutation in the URA5.3 gene and cannot synthesize uracil. For this reason, the *Cyanidioschyzon merolae* M4 strain cannot grow in a medium containing no uracil. Accordingly, in a case where the *Cyanidioschyzon merolae* M4 strain is used as a parent strain and the URA5.3 gene of the wild type strain is used as a selectable marker, a transformant into which a fusion gene has been introduced can be selected. More specifically, the fusion protein gene operably linked to a promoter is linked to the URA5.3 gene set of the wild type strain of *Cyanidioschyzon merolae* (for example, the 10D strain) and introduced into the *Cyanidioschyzon merolae* M4 strain. Then, by culturing in a medium containing no uracil, cells into which the fusion protein gene has been introduced can be obtained.

The method of introducing any fusion protein gene into an acid-resistant cell is not particularly limited, and a known method can be used. Examples of the gene transfer method include a polyethylene glycol method, a lipofection method, a microinjection method, a DEAE dextran method, a gene gun method, an electroporation method, and a calcium phosphate method.

The fusion protein gene may be present as a plasmid or the like in the acid-resistant cell or may be inserted into any one of the nuclear genome, the chloroplast genome, and the mitochondrial genome. In the case of being inserted into the genome, the fusion protein gene may be inserted at a specific position in the genome or may be randomly inserted into the genome.

Homologous recombination can be used as a method of inserting a fusion protein gene at a specific position in the genome. For example, in *Cyanidioschyzon merolae*, decoding of the entire genome sequence has been completed (Matsuzaki M et al., Nature. 2004 Apr. 8; 428 (6983): 653 to 657.), and thus it is possible to insert a fusion protein gene at the desired position in the genome. The insertion position of a fusion protein gene in *Cyanidioschyzon merolae* is not particularly limited, and examples thereof include a region between CMD184C and CMD185C.

In the fusion protein gene, the order of arranging a drug peptide and a translocation signal or translocation protein is appropriately selected depending on the kind of the translocation signal or translocation protein. Generally, the coding sequence of the translocation signal or translocation protein is located on the 5' side from the drug peptide coding sequence.

In a case where a gene encoding a drug peptide (hereinafter referred to as a "drug peptide gene") is inserted into the chloroplast genome or the mitochondrial genome, the drug peptide does not necessarily have to be a fusion protein with a translocation signal or translocation protein. For example, in a case where a drug peptide gene is operably linked to a promoter capable of functioning in the chloroplast and inserted into the chloroplast genome in an expressible state so that the drug peptide gene is expressed in the chloroplast, the drug peptide can be localized in the chloroplast. For example, in a case where a drug peptide gene is operably linked to a promoter capable of functioning in the mitochondrion and inserted into the mitochondrial genome in an expressible state so that the drug peptide gene is expressed in the mitochondrion, the drug peptide can be localized in the mitochondrion.

In the drug delivery composition of the present embodiment, the drug is preferably localized in the organelle and more preferably localized in the chloroplast. In addition, the drug is preferably a drug peptide and is preferably localized in the organelle, which is the target of the corresponding translocation signal or translocation protein, in the form of a fusion protein with the translocation signal or translocation protein. The translocation signal or translocation protein is more preferably a chloroplast translocation signal or chloroplast translocation protein.

Optional Component

The drug delivery composition of the present embodiment may contain other components in addition to the acid-resistant cell. Examples of the other components include, but are not limited to, a pharmaceutically acceptable carrier. "Pharmaceutically acceptable carrier" means a carrier that does not inhibit the function of the drug enclosed in the acid-resistant cell and does not exhibit substantial toxicity to an administration subject. The description "does not exhibit substantial toxicity" means that the component having toxicity does not exhibit toxicity to an administration subject at the ordinarily used dose. The pharmaceutically acceptable carrier is not particularly limited; however, examples thereof include an excipient, a binder, a disintegrant, a lubricant, an emulsifier, a stabilizer, a diluent, an oily base, a thickener, an antioxidant, a reducing agent, an oxidizing agent, a chelating agent, and a solvent. The pharmaceutically acceptable carrier may be used alone, or two or more kinds thereof may be used in combination. The pharmaceutically acceptable carrier is preferably one that does not damage the acid-resistant cell.

The drug delivery composition of the present embodiment can be appropriately mixed with other components to form a granule agent, a tablet, a jelly agent, a liquid agent, a capsule agent, and the like according to a conventional method. Among these drug forms, a drug form that does not damage the acid-resistant cell is preferable, and for example, a jelly agent, a liquid agent, a capsule agent, or the like is preferable. For example, as described in Examples which will be described later, the drug form may be a form of a solidified body of alginate, containing an acid-resistant cell. In addition to the alginate, a suspension containing an acid-resistant cell may be solidified using a thickener such as gelatin, agar, carrageenan, roast bean gum, guar gum, xanthan gum, pectin, gellan gum, tamarind seed gum, or gum arabic, or a gelling agent to be used as the drug delivery composition of the present embodiment. The medium that is used for suspending the acid-resistant cell is not particularly limited; however, it is preferably one that does not cause the cell rupture of an acid-resistant cell, and an isotonic solution having a pH of about 1 to 6 is preferable. Examples of the isotonic solution include a medium that is used for culturing an acid-resistant cell, a glucose isotonic solution and a sucrose isotonic solution which are prepared at about pH 1 to 6, and various buffer solutions (phosphate buffered saline, a HEPES buffer solution, a citric acid buffer, a Tris buffer, and the like). In one embodiment, the drug delivery composition is a solidified body of an acid-resistant cell, which is obtained by using a thickener or a gelling agent. The drying of the acid-resistant cell can be prevented in the case of a solidified body which is obtained by using a thickener and/or a gelling agent. The description "solidified body of an acid-resistant cell, which is obtained by using a thickener or a gelling agent" means one which is obtained by gelling and solidifying a suspension of an acid-resistant cell with a thickener or a gelling agent. In other words, the "solidified body of an acid-resistant cell, which is obtained by using a thickener or a gelling agent" is a gel composition containing an acid-resistant cell and at least one selected from the group consisting of a thickener and a gelling agent.

The route of administration of the drug delivery composition of the present embodiment is not particularly limited and may be oral administration or parenteral administration; however, oral administration is preferable. In the drug delivery composition of the present embodiment, since the drug is enclosed in the acid-resistant cell, it is possible to suppress the degradation of the drug by gastric acid. As a result, the drug delivery composition of the present embodiment is suitable for oral administration.

The drug delivery target of the drug delivery composition of the present embodiment is preferably the intestine (the intestinal tract) and more preferably the small intestine. In a case where the drug delivery composition of the present embodiment is orally administered, the drug is protected in cells of the acid-resistant cell and passes through the stomach. Then, in the case of reaching the intestine, the cell rupture of the acid-resistant cell occurs due to the neutral to weakly alkaline pH condition (pH 7 or higher) in the intestinal tract, and the drug is released into the intestinal tract. The drug released into the intestinal tract acts inside the intestinal tract and contributes to the enhancement of intestinal immunity. Further, other mucosal immunity and systemic immunity can be expected to be activated by the enhancement of intestinal immunity.

As described above, according to the drug delivery composition of the present embodiment, since the drug is enclosed in the acid-resistant cell, it is expected that the degradation of the drug will be suppressed in the stomach and thus the drug can be delivered to the intestine. In addition, due to being localized in the sac-shaped membrane structure in the acid-resistant cell, the drug is protected from degradation by a degrading enzyme in the cytoplasm.

Further, in a case where an acid-resistant cell into which a drug peptide gene or a fusion protein gene containing a coding sequence of a drug peptide has been introduced is used, acid-resistant cells that enclose a drug can be easily proliferated. In particular, the algae that belong to the class Cyanidiophyceae can be proliferated under conditions in which acidity is high and other organisms cannot survive, and thus outdoor culture is also possible on a large-scale. As a result, a reduction of production cost can be expected.
Feed In one embodiment, the present invention provides a feed containing the drug delivery composition of the above embodiment.

The kind of animal to which the feed of the present embodiment is fed is not particularly limited. Examples thereof include, but are not limited to, livestock (cattle, pigs, chickens, horses, sheep, goats, and the like), pets (dogs, cats, hamsters, rabbits, true parrots, tropical fishes, reptiles, amphibians, insects, and the like), aquatic animals (fishes, shellfishes, and the like), and experimental animals (mice, rats, guinea pigs, and the like).

The feed of the present embodiment may contain other components in addition to the drug delivery composition of the above embodiment. Examples of the other components include commonly used feeds (including a livestock feed, an aquatic feed, and a pet food). For example, the drug delivery composition of the above embodiment may be added to an existing feed as a feed additive. The feed to which the drug delivery composition of the above embodiment is added is not particularly limited and may be appropriately selected depending on the target animal. In a case where the drug delivery composition of the above embodiment is added to an ordinary feed, it is possible to feed an animal with a drug according to ordinary feeding behavior.

The drug delivery composition that is used for the feed of the present embodiment may have any form; however, it preferably has a form with which the cells of the acid-resistant cell are not damaged so that drug leakage from the acid-resistant cell is prevented. Examples of the form thereof include forms of the jelly agent and the capsule agent exemplified above and a form obtained by solidification with a gelling agent and/or a thickener. In a case where the drug delivery composition is added to a feed as the feed additive, for example, a solidified body of the drug delivery composition, which is obtained by using a thickener and/or a gelling agent, may be prepared to have an appropriate size and may be added to and mixed with the feed. Alternatively, the drug delivery composition may be added to and mixed with a feed, and then the mixture may be solidified by using a gelling agent and/or a thickener. The solidified body can be appropriately adjusted to have an appropriate size depending on the size of the animal. The drying of the acid-resistant cell can be prevented in the case of a solidified body which is obtained by using a thickener and/or a gelling agent.

The content of the drug delivery composition of the above embodiment in the feed of the present embodiment is not particularly limited, and the content thereof may be appropriately set depending on the kind of the feed. Examples of the content of the drug delivery composition in the feed include 0.01% to 80% by mass, and the content thereof is preferably 0.1% to 70% by mass, more preferably 0.1% to 60% by mass, and particularly preferably 0.1% to 50% by mass. Examples of the content of the acid-resistant cell in the feed include 0.1 to 100 mg (wet weight)/g, 0.5 to 80 mg (wet weight)/g, and 1 to 60 mg (wet weight)/g.

Since the feed of the present embodiment contains the drug delivery composition of the above embodiment, it is possible to feed an animal with any drug as a feed. As described above, according to the drug delivery composition, any drug can be protected from degradation in the stomach and can be delivered to the intestine. As a result, in a case where a drug that acts in the intestine is used in the drug delivery composition, the drug can efficiently act on the intestine of an animal. In addition, in a case where the drug is a drug peptide that has immunogenicity, intestinal immunity can be efficiently activated in an animal that has fed on the drug delivery composition. Further, it other mucosal immunity and systemic immunity can be expected to be activated by the activation of intestinal immunity.

In another aspect, the present invention provides a method of rearing an animal, including feeding an animal with a feed containing the drug delivery composition of the above embodiment.

In addition, in another aspect, the present invention provides a method of imparting intestinal immunity to an animal, including feeding an animal with a feed containing the drug delivery composition of the above embodiment.
Pharmaceutical Product In one embodiment, the present invention provides a pharmaceutical product containing the drug delivery composition of the above embodiment.

The pharmaceutical product of the present embodiment may be a pharmaceutical product for a human or a pharmaceutical product for an animal. In the case of the pharmaceutical product for an animal, the kind of animal to which the pharmaceutical product is applied is not particularly limited. Examples thereof include, but are not limited to, livestock (cattle, pigs, chickens, horses, sheep, goats, and the like), pets (dogs, cats, hamsters, rabbits, true parrots, tropical fishes, reptiles, amphibians, insects, and the like), aquatic animals (fishes, shellfishes, and the like), and experimental animals (mice, rats, guinea pigs, and the like).

The pharmaceutical product of the present embodiment may contain other components in addition to the drug delivery composition of the above embodiment. Examples of the other components include, but are not limited to, a pharmaceutically acceptable carrier. "Pharmaceutically acceptable carrier" means a carrier that does not inhibit the function of the drug and does not exhibit substantial toxicity to an administration subject. In addition, the description "does not exhibit substantial toxicity" means that the component having toxicity does not exhibit toxicity to an administration subject at the ordinarily used dose. The pharmaceutically acceptable carrier is not particularly limited; however, examples thereof include an excipient, a binder, a disintegrant, a lubricant, an emulsifier, a stabilizer, a diluent, an oily base, a thickener, an antioxidant, a reducing agent, an oxidizing agent, a chelating agent, and a solvent. The pharmaceutically acceptable carrier may be used alone, or two or more kinds thereof may be used in combination. The other components may be components other than those listed above, and for example, a pharmaceutical product additive that is generally used in pharmaceutical products can be used without particular limitation. In addition, the other components may be an active component other than the drug contained in the drug delivery composition. The active substance is not particularly limited; however, examples thereof include an intestinal regulator, an anti-inflammatory agent, an antibiotic, an antibacterial substance, a crude drug, a blood circulation promoting agent, an antipyretic agent, and an analgesic.

The drug form of the pharmaceutical product of the present embodiment is not particularly limited; however, it preferably has a form with which the cells of the acid-resistant cell are not damaged so that drug leakage from the acid-resistant cell is prevented. Examples thereof include a tablet, a granule agent, a jelly agent, a capsule agent, a liquid agent, and a syrup agent. For example, the pharmaceutical product of the present embodiment may contain a solidified body of an acid-resistant cell, which is obtained by using a thickener or a gelling agent.

The content of the drug delivery composition of the above embodiment in the pharmaceutical product of the present embodiment is not particularly limited, and the content thereof may be appropriately set depending on the kind of the drug contained in the drug delivery composition. Examples of the content of the drug delivery composition in the pharmaceutical product include 0.01% to 80% by mass, and the content thereof is preferably 0.1% to 70% by mass, more preferably 0.1% to 60% by mass, and particularly preferably 0.1% to 50% by mass. Examples of the content of the acid-resistant cell in the pharmaceutical product include 0.1 to 100 mg (wet weight)/g, 0.5 to 80 mg (wet weight)/g, and 1 to 60 mg (wet weight)/g.

The route of administration of the pharmaceutical product of the present embodiment is not particularly limited and may be oral administration or parenteral administration; however, oral administration is preferable. In the pharmaceutical product of the present embodiment, since the drug is enclosed in the acid-resistant cell, it is possible to suppress the degradation of the drug by gastric acid.

The drug delivery target of the pharmaceutical product of the present embodiment is preferably the intestine (the intestinal tract) and more preferably the small intestine.

Since the pharmaceutical product of the present embodiment contains the drug delivery composition of the above embodiment, any drug can be protected from degradation in the stomach and can be delivered to the intestine. As a result, in a case where a drug that acts in the intestine is used in the drug delivery composition, the drug can efficiently act on the intestine. In addition, in a case where the drug is a drug peptide that has immunogenicity, intestinal immunity can be efficiently activated in an animal that has fed on the drug delivery composition. Further, other mucosal immunity and systemic immunity can be expected to be activated by the activation of intestinal immunity.

As a result, the pharmaceutical product of the present embodiment can be used for the prevention and the treatment of human disease and human health promotion. In particular, it is suitably used for a drug that is desired to be absorbed in the intestine but not in the stomach, a drug of which absorption in the intestine is obstructed due to degradation or insolubilization by gastric acid, a pharmaceutical product for absorbing a plurality of drugs in the intestine at once, and the like.

In another aspect, the present invention provides a method of administering a drug, which includes orally administering a pharmaceutical product containing the drug delivery composition of the above embodiment to a subject.

Further, in another aspect, the present invention provides a method of imparting intestinal immunity to a subject, including orally administering a pharmaceutical product containing the drug delivery composition of the above embodiment to a subject.

Food

In one embodiment, the present invention provides a food containing the drug delivery composition of the above embodiment.

The food of the present embodiment may be a general food, a nutritional supplementary food, a functional food, a supplement, or the like. The drug delivery composition may be added to the food as a food additive.

In the food of the present embodiment, the kind of the food is not particularly limited; however, the food preferably has a form with which the cells of the acid-resistant cell are not damaged so that drug leakage from the acid-resistant cell is prevented and is preferably not a dry food. Examples of the food include, but are not limited to, drinks such as an Aojiru juice, a soft drink, a carbonated drink, a nutritional drink, a fruit drink, a vegetable drink, a fermented lactic drink, a milk drink, a sports drink, tea, and coffee; various soups such as curry roux, stew roux, and instant soup; frozen desserts such as ice cream, ice sherbet, and shaved ice; confectionery such as a candy, a jelly, a jam, and a cream; fishery and livestock processed foods such as boiled fish-paste, hanpen (a cake of ground fish), ham, and sausage; dairy products such as processed milk, fermented milk, butter, cheese, and yogurt; seasonings such as a sauce, a dressing, fermented soybean paste, soy sauce, and a dipping sauce; and other processed foods such as various retort foods.

In the food of the present embodiment, the content of the drug delivery composition is not particularly limited, and the content thereof may be appropriately set depending on the kind of the food. In consideration of the flavor of the food, examples of the content of the drug delivery composition in the food include 0.01% to 80% by mass, and the content thereof is preferably 0.1% to 70% by mass, more preferably 0.1% to 60% by mass, and particularly preferably 0.1% to 50% by mass. Examples of the content of the acid-resistant cell in the food include 0.1 to 100 mg (wet weight)/g, 0.5 to 80 mg (wet weight)/g, and 1 to 60 mg (wet weight)/g.

In the case of a functional food, a nutritional supplementary food, a supplement, or the like, the food may have the form of a general food as described above or may have the form of a granule agent, a tablet, a jelly agent, a drink agent, or the like. For example, the food of the present embodiment may contain a solidified body of an acid-resistant cell, which is obtained by using a thickener or a gelling agent.

Since the food of the present embodiment contains the drug delivery composition of the above embodiment, it is possible to feed on any drug as a food. As described above, according to the drug delivery composition, any drug can be protected from degradation in the stomach and can be delivered to the intestine. The food of the present embodiment is useful in a case where one or more specific nutritional components are desired to be absorbed in the intestine without being affected by gastric acid.

Drug Carrier

In one embodiment, the present invention provides a drug carrier containing an acid-resistant cell.

The acid-resistant cell contained in the drug carrier of the present embodiment is the same as the acid-resistant cell described in "Acid-resistant cell" of "Drug delivery composition" described above, and the same applies to the preferred example thereof. The acid-resistant cell is resistant to acids and is not damaged even in an acidic environment such as the stomach. Accordingly, in a case where a drug is enclosed in a cell, the cell can be used as an acid-resistant drug carrier. Examples of the method of enclosing a drug in a cell include the same method as the method described in "Drug delivery composition". The drug carrier of the present embodiment is preferably composed of an acid-resistant cell.

The drug carrier of the present embodiment can be suitably used for delivering a drug to the intestine and can be suitably applied to a pharmaceutical product to be orally administered, or a feed or food to be orally fed.

Drug Capsule

In one embodiment, the present invention provides a drug capsule in which a drug is enclosed in the drug carrier of the embodiment.

The acid-resistant cell encloses a drug in the cell, and as shown in Examples described later, the release of the drug hardly occurs in an acidic environment such as the stomach. For this reason, in the case of enclosing a drug in the cell of the acid-resistant cell, the drug carrier containing the acid-resistant cell can be used as an acid-resistant drug capsule. The drug capsule of the present embodiment can be used as an oral drug capsule for the intended purpose of delivering the drug to the intestine.

Acid-Resistant Cell

In one embodiment, the present invention provides an acid-resistant cell that encloses a drug in a cell. In a preferred embodiment, the drug is localized in the sac-shaped membrane structure included in an acid-resistant cell.

The acid-resistant cell of the present embodiment is the same as the acid-resistant cell contained in the drug delivery composition of the above embodiment, and the same applies to the preferred example thereof. Alternatively, the drug is localized outside the sac-shaped membrane structure included in the acid-resistant cell. When a drug is localized outside the sac-shaped membrane structure, the drug is present in the cytoplasm of the acid-resistant cell.

The drug is not particularly limited; however, it is preferably at least one drug selected from the group consisting of a low molecular weight compound, a peptide, a protein, and a nucleic acid. For example, in the case of a drug that is affected by a degrading enzyme or the like in the cytoplasm, the drug is preferably localized in the sac-shaped membrane structure. In the case of being localized in the sac-shaped membrane structure, the drug is protected from the influence of a degrading enzyme or the like in the cytoplasm. As a result, the drug can be efficiently delivered to a predetermined site in the living body. For example, in a case where a drug is a peptide, a protein, or a nucleic acid, the drug is easily affected by a protease or a nuclease in the cytoplasm. For this reason, the drug is preferably localized in the sac-shaped membrane structure. On the other hand, in the case of a drug (for example, a low molecular weight compound) that is not easily affected by a degrading enzyme or the like in the cytoplasm, the drug may be localized outside the sac-shaped membrane structure.

Further, in one embodiment, the present invention provides an acid-resistant cell containing an exogenous substance.

The acid-resistant cell of the present embodiment is the same as the acid-resistant cell described in "Acid-resistant cell" of "Drug delivery composition" described above, and the same applies to the preferred example thereof.

The exogenous substance is not particularly limited, and examples thereof include, but are not limited to, a drug, a poison, a dye, a flavoring agent, and a compound having unknown effects on the living body. The method of introducing the exogenous substance into an acid-resistant cell is not particularly limited; however, examples thereof include a method of binding the exogenous substance to a cell-permeable substance (a cell-permeable peptide or the like) and a method of enclosing the exogenous substance in a cell-permeable micelle. In addition, in a case where the exogenous substance is a drug, examples thereof include the same method as that described in "Drug delivery composition".

The acid-resistant cell of the present embodiment can be used, for example, for delivering an exogenous substance. More specifically, the acid-resistant cell of the present embodiment can be applied to an oral composition for delivering an exogenous substance to the intestine.

In another aspect, the present invention provides a feed containing the acid-resistant cell.

In another aspect, the present invention provides a pharmaceutical product containing the acid-resistant cell.

In another aspect, the present invention provides a food containing the acid-resistant cell.

In addition, in another aspect, the present invention provides a method of administering the exogenous substance, which includes orally administering the acid-resistant cell to a subject.

In another aspect, the present invention provides a method of rearing an animal, including feeding an animal with the acid-resistant cell.

In another aspect, the present invention provides a method of imparting intestinal immunity, including orally administering the acid-resistant cell.

Method of Producing Acid-Resistant Cell

In one embodiment, the present invention provides a method of producing an acid-resistant cell in which a drug is enclosed, where the method includes a step of introducing into the acid-resistant cell a gene encoding a fusion protein that contains a peptide or protein as a drug and contains a peptide or protein localizable to a cell membrane or an organelle.

The producing method of the present embodiment can be carried out as described in "Drug localization to sac-shaped membrane structure" of "Drug delivery composition" of "Acid-resistant cell".

EXAMPLES

The present invention will be described with reference to examples; however, the present invention is not limited to Examples below.

Example 1

Preparation of GAPDH-GP-sfGFP Expressing Strain

First, for inserting a DNA fragment of GAPDH-GP-sfGFP downstream of CMD184C (gene number) of the chromosome of *Cyanidioschyzon merolae* 10D, a plasmid pD184-HSp-GAPDH-GP-sfGFP was prepared as follows.

This plasmid was designed so that the following sequences were arranged in order at the multicloning sites of a pQE80 plasmid (a plasmid for maintenance and replication in *E. coli*; manufactured by QIAGEN). The sequences are arranged in order from the 5' side, the latter half of the CMD184C gene (773 bp to 2,773 bp of the gene reading frame (ORF) and the downstream 25 bp containing the stop codon), the heat shock (HS) promoter (the upstream 200 bp sequence adjacent to the start codon of the HSP20/CMJ101C gene; Sumiya et al. 2014, PLoS One. 22; 9 (10): e111261; PMID: 25337786), GAPDH (1 bp to 1,209 bp of the CMJ042C gene reading frame; GAPDH is described in Moriyama et al. 2014, Planta. 240 (3): 585 to 598; PMID: 25009310), the rabies virus glycoprotein gene GP (1 to 1,572 bp of the ORF full length, UniProtKB accession No. P19462), the β-tubulin terminator (the downstream 200 bp containing the stop codon of the β-tubulin/CMN263C gene), the URA selection marker, and the downstream of the CMD185 gene (the nucleotide sequence from 28 bp to 1,880 bp downstream of the stop codon). The HS promoter is required to warm a medium and induce the expression of GAPDH-GP-sfGFP. The URA selection marker is required for the selection of the GAPDH-GP-sfGFP strain. The latter half and downstream sequences of CMD184C and the downstream of the CMD185C gene are required to insert a DNA fragment downstream of CMD184C by homologous recombination.

First, in order to prepare the plasmid pD184-HSp-GAPDH-GP-sfGFP, each of the following DNA fragments (1), (2), (3), (4), and (5) was prepared.

(1) The PCR method was carried out using a plasmid pD184-APCCp-EGFP-URA$_{Cm-Cm}$ (including pQE80 (SEQ ID NO: 32), the latter half of CMD184C (SEQ ID NO: 33), the APCC promoter (SEQ ID NO: 34), EGFP (SEQ ID NO: 35), the β-tubulin terminator (SEQ ID NO: 36), the URA selection marker (SEQ ID NO: 37), and the DNA sequence downstream of the CMD185C gene (SEQ ID NO: 38); Fujiwara et al. 2013, PLoS One. 8 (9): e73608; PMID: 24039997) as a template and using a primer set [#1 d184(+25)R/#2 bT3'(+1)F], whereby a DNA sequence of the portion excluding the APCC promoter and EGFP was amplified. The nucleotide sequence of the DNA fragment of (1) is set forth in SEQ ID NO: 31.

(2) The PCR method was carried out using the genomic DNA of *C. merolae* 10D as a template and using a primer set [#3 HS(−200)Fd184/#4 HS(−1)R], whereby a DNA sequence of the HS promoter (SEQ ID NO: 39) was amplified.

(3) The PCR method was carried out using the genomic DNA of *C. merolae* 10D as a template and using a primer set [#5 J042(1)Fhs/#6 J042(1209)R-link3], whereby a GAPDH gene reading frame (SEQ ID NO: 40) was amplified.

(4) The PCR method was carried out using a DNA sequence of GP which had been chemically synthesized according to the codon usage frequency of *C. merolae* as a template, and using a primer set [#7 GP(1)F-link3/#8 GP(1572)R-linker2], whereby the DNA sequence of GP (SEQ ID NO: 41) was amplified.

(5) The PCR method was carried out using pAPCC-promoter-sfGFP-pmE2F-URA (Miyagishima et al. 2014, Nat Commun. 5: 3807; PMID: 24806410) as a template and using a primer set [#9 sfGFP(1)F-linker2/#10 sfGFP(714)Rbt], whereby sfGFP (SEQ ID NO: 42) was amplified.

The DNA fragments of the above (1), (2), (3), (4), and (5) were mixed, fused using In-Fusion (registered trade mark) HD Cloning Kit (product code: 639648, Takara Bio Inc.), and the HS promoter, GAPDH, GP, and sfGFP were inserted into pD184-APCCp-EGFP-URA$_{Cm-Gs}$ so that the portions of the APCC promoter and EGFP were replaced. After the In-Fusion reaction, the plasmid was introduced into *Escherichia coli* competent cells and amplified to obtain pD184-HSp-GAPDH-GP-sfGFP. Next, the PCR method was carried out using this as a template and using a primer set [#11 D184(1200)F/#12 D184(+1400)R], whereby a DNA fragment in which the latter half of the CMD184 gene (1,200 bp to 2,737 bp of the gene ORF and the downstream 25 bp containing the stop codon), the HS promoter, GAPDH, GP, sfGFP, β-tubulin terminator, URA selection marker, and the downstream of the CMD184C gene (the nucleotide sequence from 28 bp to 1,440 bp downstream of the stop codon) were linked was amplified.

This DNA fragment was introduced into a uracil auxotrophic strain M4 (Minoda et al. 2004, Plant Cell Physiol. 45 (6): 667 to 671.; PMID: 15215501) of *C. merolae* by the PEG method (Ohnuma et al. 2008, Plant Cell Physiol. 49 (1): 117 to 120; PMID: 18003671), and selection was carried out with an MA2 solid medium containing no uracil, whereby a GAPDH-GP-sfGFP expressing strain was obtained.

Evaluation of Degradation of GAPDH-GP-sfGFP Protein By Proteasome

The GAPDH-GP-sfGFP expressing strain of *C. merolae* (hereinafter referred to as the "GAPDH-GP-sfGFP expressing strain") obtained as described above was subcultured in 60 mL of an MA2 medium in an Erlenmeyer flask at a cell concentration of OD750=0.2, and subjected to swirling culture under light irradiation (50 μmolm$^{-2}$s$^{-1}$) at 40° C. for 2 days (before expression). Next, 20 mL of this culture solution was transferred to two Erlenmeyer flasks. In order to induce the GAPDH-GP-sfGFP gene expression by heat stimulation, the two Erlenmeyer flasks were transferred to an incubator at 50° C. and subjected to swirling culture under light irradiation for 1 hour. Immediately before transferring to 50° C., a proteasome inhibitor MG-132 was added to one of the two Erlenmeyer flasks to a final concentration of 100 μM to inhibit proteolysis by the proteasome (MG-132 (+)) (Nishida. et al. 2005; Mol Biol Cell. 16 (5): 2493 to 2502; PMID: 15772156). As a control, 40 μL of DMSO, which is the solvent of MG-132, was added to the other Erlenmeyer flask (MG-132 (−)). The expression of the GAPDH-GP-sfGFP protein was checked by immunoblotting, and the effect of proteasome inhibition was verified by comparing band patterns. An anti-GFP antibody (clone JL-8, product code: 632381, Takara Bio Inc.) was used to detect the GAPDH-GP-sfGFP protein.

The result of the immunoblotting is shown in FIG. 1. In MG-132 (−), the band of the GAPDH-GP-sfGFP protein was thinner than that in MG-132 (+). From this result, it was shown that the GAPDH-GP-sfGFP protein is partially degraded by the proteasome after expression.

Analysis of Intracellular Localization of GAPDH-GP-sfGFP Protein

In order to analyze the intracellular localization of the GAPDH-GP-sfGFP protein, the GAPDH-GP-sfGFP expressing strain was cultured under light irradiation at 50° C. in the presence of MG-132 for 1 hour, and then the fluorescence of the GAPDH-GP-sfGFP protein was observed under the fluorescence microscope.

Figure 2:
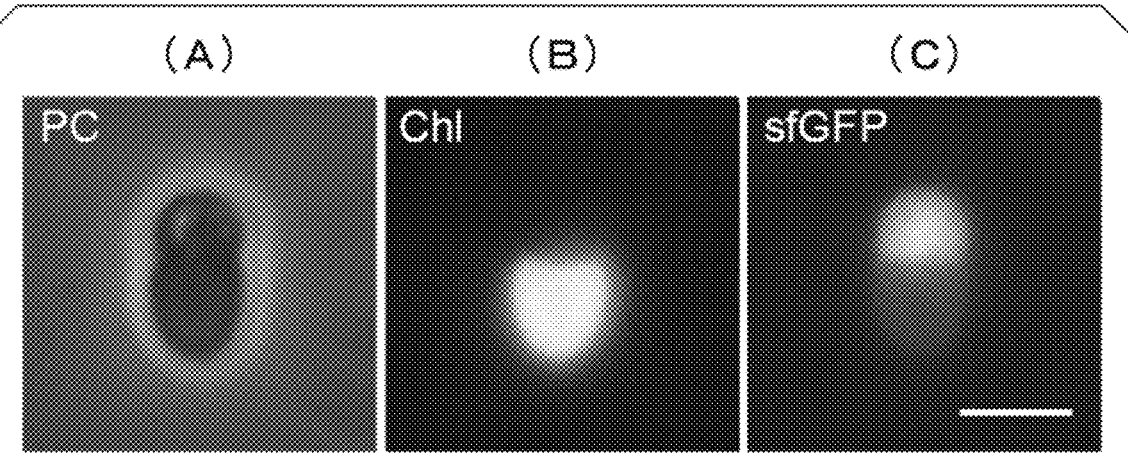
FIG. 2 is fluorescence microscope images of the GAPDH-GP-sfGFP expressing strain. (A) PC: phase-contrast microscope image showing cell outline; (B) Chl: autofluorescence image of chloroplast; (C) sfGFP: fluorescence image of sfGFP.

Fluorescence microscope images of the GAPDH-GP-sfGFP expressing strain are shown in FIG. 2. The fluorescence signal of sfGFP showed that the GAPDH-GP-sfGFP protein was localized in the cytoplasm. The image (PC) of FIG. 2 (A) is a phase-contrast microscope image showing the outline of a cell, the image (Chl) of FIG. 2 (B) is an autofluorescence image of a chloroplast, and the image (sfGFP) of FIG. 2 (C) is a fluorescence image of sfGFP.

Example 2

Preparation of Chl-TP-3HA-GP-Co1 Expressing Strain

Figure 3:
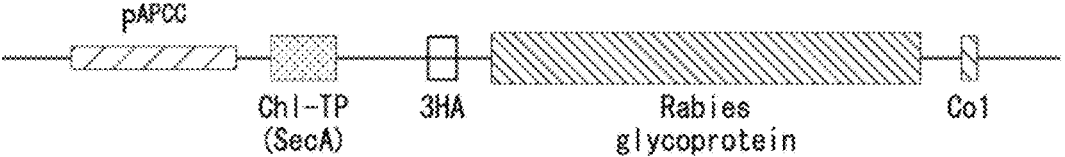
FIG. 3 is a diagram showing a structure of a DNA fragment used for preparing a Chl-TP-3HA-GP-Col expressing strain in Example 2.

First, for inserting a DNA fragment for expressing Chl-TP-3HA-GP-Co1 (see FIG. 3) downstream of CMD184C (gene number) of the chromosome of *C. merolae* 10D, a plasmid pD184-APCCp-Chl-TP-3HA-GP-Co1 was prepared as follows.

This plasmid was designed so that the following sequences were arranged in order from the 5' side at the multicloning sites of a pQE80 plasmid. The sequences are arranged in order from the 5' side, the latter half of the CMD184C gene (773 bp to 2,737 bp of the gene ORF and the downstream 25 bp containing the stop codon), the APCC promoter (the upstream sequence 600 bp adjacent to the start codon of the APCC/CMO250C gene), the chloroplast translocation signal Chl-TP (1 bp to 390 bp of the SECA/CMQ393C gene ORF; Sumiya et al. 2016, Proc Natl Acad Sci USA. 113 (47): E7629-E7638; PMID: 27837024), a sequence encoding a 3×HA tag (for confirming expression with the anti-HA antibody), the rabies virus glycoprotein gene GP (1,572 bp, UniProtKB accession No. P19462), a sequence encoding Co1 peptide (the Co1 peptide: SFHQL-PARSPLP (SEQ ID NO: 43), a peptide that improves antigen recognition of the M cell involved in intestinal immunity; Kim et al. 2010, J Immunol. 185 (10): 5787 to 5795; PMID: 20952686), the β-tubulin gene terminator (the downstream 200 bp containing the stop codon of the β-tubulin/CMN263C gene), the URA$_{Cm-Gs}$ selection marker, and the downstream of the CMD185 gene (the nucleotide sequence from 28 bp downstream of the stop codon to 880 bp). The latter half and downstream sequences of CMD184C and the downstream of the CMD185 gene are required to insert a DNA fragment downstream of CMD184C by homologous recombination. The APCC promoter is required for constitutive expression of Chl-TP-HA-GP-Co1 (Watanabe et al. 2011, J Gen Appl Microbiol. 57 (1): 69 to 72; PMID: 21478650). The URA$_{Cm-Gs}$ selection marker is required to select a transformant into which Chl-TP-3HA-GP-Co1 has been inserted (Imamura et al. 2010, Plant Cell Physiol. 51 (5): 707 to 717; PMID: 20375110), and it is possible to increase the protein expression level by making multiple copies of the gene (Fujiwara et al. 2013, PloS One 8 (9): e73608; PMID: 24039997).

In order to prepare the plasmid pD184-APCCp-Chl-TP-HA-GP-Co1, the following DNA fragments (1), (2), (3), and (4) were prepared.

(1) The PCR method was carried out using a plasmid pD184-APCCp-EGFP-URA$_{Cm-Gs}$ (including pQE80 (SEQ ID NO: 32), the latter half of CMD184C (SEQ ID NO: 33), the APCC promoter (SEQ ID NO: 34), EGFP (SEQ ID NO: 35), the β-tubulin terminator (SEQ ID NO: 36), the URA$_{Cm-Gs}$ selection marker (SEQ ID NO: 44), and the DNA sequence downstream of the CMD185 gene (SEQ ID NO: 38); Fujiwara et al. 2013, PLoS One. 8 (9): e73608; PMID: 24039997) as a template and using primers [#13 APCC(-1)R/#14bT3' (+1)], whereby a DNA sequence of the portion excluding EGFP was amplified.

(2) The PCR method was carried out using the genomic DNA of *C. merolae* 10D as a template and using a primer set [#15 SecA(1)Fapcc/#16 SecA(390)R-linker-ha], whereby a DNA sequence of Chl-TP (SEQ ID NO: 45) was amplified.

(3) The PCR method was carried out using a plasmid DNA, pBSb-THA (Ohnuma et al. 2008, Plant Cell Physiol. 49 (1): 117 to 120; PMID: 18003671) containing 3×HA, as a template and using a primer set [#17 HA(1)F/#18 HA(90)R], whereby 3×HA (SEQ ID NO: 46) was amplified.

(4) The PCR method was carried out using an ORF of GP which had been chemically synthesized according to the codon usage frequency of *C. merolae* as a template, and using a primer set [#19 GP(1)Fha/#20 Co1-GP (1680)Rbt], whereby the ORF of GP (SEQ ID NO: 40) was amplified.

The DNA fragments of the above (1), (2), (3), and (4) were mixed, fused using In-Fusion (registered trade mark) HD Cloning Kit (product code: 639648, Takara Bio Inc.), and the Chl-TP, 3×HA, and the rabies virus glycoprotein ORF were inserted into pD184-APCCp-EGFP-URA$_{Cm-Gs}$ so that the portion of EGFP was replaced. After the In-Fusion reaction, the plasmid was introduced into *Escherichia coli* competent cells and amplified to obtain pD184-APCCp-Chl-TP-3HA-GP-bt-URACm-Gs. Next, the PCR method was carried out using this as a template and using primers [#11 D184(1200)F/#12 D184(+1400)R], whereby a DNA fragment in which the latter half of the CMD184C gene (1,200 bp to 2,737 bp of the gene ORF and the downstream 25 bp containing the stop codon), the APCC promoter, Chl-TP, 3×HA, GP, the Co1 peptide, the β-tubulin terminator, URA$_{Cm-Gs}$ selection marker, and the downstream of the CMD185C gene (the nucleotide sequence from 28th bp to 1,440th bp) were linked was amplified.

This DNA fragment was introduced into a uracil auxotrophic strain M4 (Minoda et al. 2004, Plant Cell Physiol. 45 (6): 667 to 671.; PMID: 15215501) of *C. merolae* by the PEG method (Ohnuma et al. 2008, Plant Cell Physiol. 49 (1): 117 to 120; PMID: 18003671), and selection was carried out with an MA2 solid medium containing no uracil, whereby a Chl-TP-3HA-GP-Co1 expressing strain was obtained.

Evaluation of Degradation of Chl-TP-3HA-GP-Co1 Protein By Proteasome

The ChlTP-sfGFP-HA-GP-Co1 expressing strain of *C. merolae* (hereinafter referred to as "Chl-TP-3HA-GP-Co1 expressing strain") obtained as described above and the wild type strain (WT) as a negative control were each subcultured in 60 mL of an MA2 medium in an Erlenmeyer flask at a cell concentration of OD750=0.2, and subjected to swirling culture under light irradiation (50 $\mu$molm$^{-2}$s$^{-1}$) at 40° C. for 2 days. Next, 20 mL of the culture solution of each strain was transferred to two Erlenmeyer flasks. A proteasome inhibitor MG-132 was added to one of the two Erlenmeyer flasks to a final concentration of 100 $\mu$M to inhibit proteolysis by the proteasome (MG-132 (+)) (Nishida et al. 2005; Mol Biol Cell. 16 (5): 2493 to 2502; PMID: 15772156). As a control, 40 $\mu$L of DMSO, which is the solvent of MG-132, was added to the other Erlenmeyer flask (MG-132 (−)). The expression of the ChlTP-sfGFP-HA-GP-Co1 protein was checked by immunoblotting, and the effect of proteasome inhibition was verified by comparing band patterns. An anti-HA antibody (clone 16B12, product code: 901503, Biolegend) was used to detect the ChlTP-sfGFP-HA-GP-Co1 protein.

Figure 4:
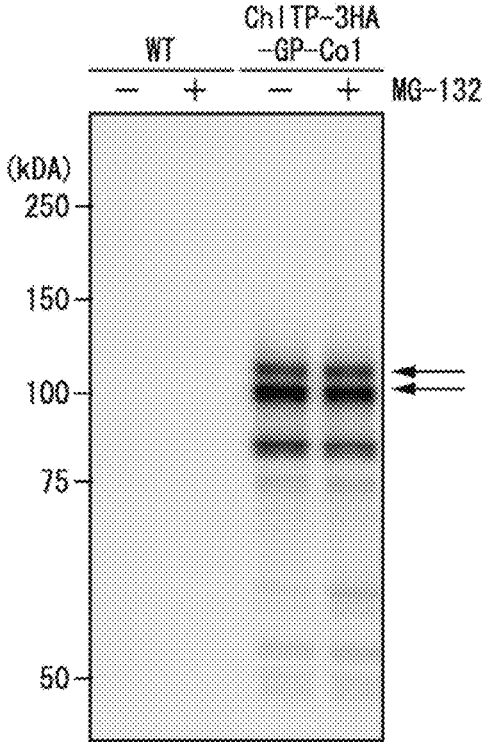
FIG. 4 is a figure showing a result of immunoblotting using an anti-HA antibody in a Chl-TP-3HA-GP-Col expressing strain cultured in the presence and absence of MG-132. In the figure, arrowheads indicate bands of a Chl-TP-3HA-GP-Col protein.

The result of the immunoblotting is shown in FIG. 4. No difference in the band pattern of the ChlTP-sfGFP-HA-GP-Co1 protein was observed between MG-132 (−) and MG-132 (+). From this result, it was shown that the ChlTP-sfGFP-HA-GP-Co1 protein is not degraded by the proteasome.

Figure 5:
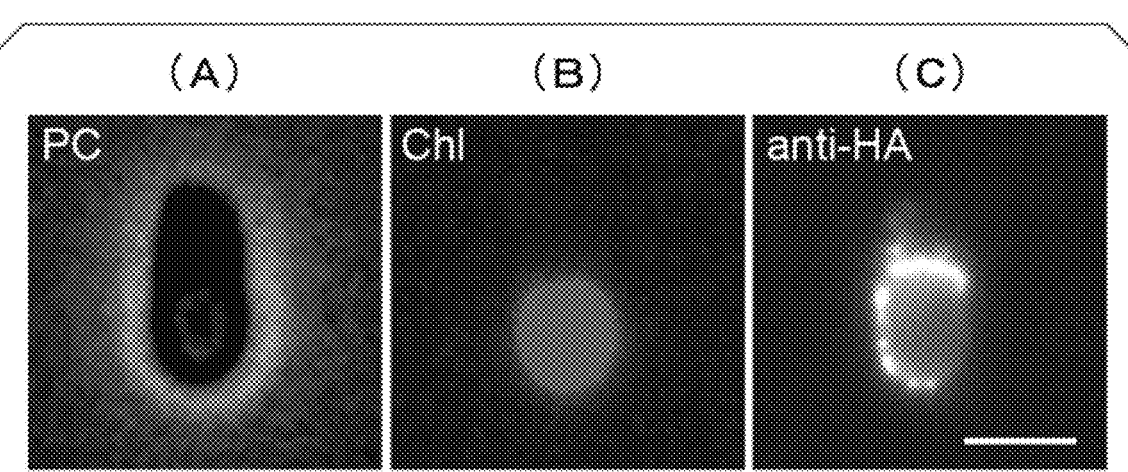
FIG. 5 is fluorescence microscope images of the Chl-TP-3HA-GP-Co1 expressing strain. (A) PC: phase-contrast microscope image showing cell outline; (B) Chl: autofluorescence image of chloroplast; (C) anti-HA: immunofluorescence staining image with an anti-HA antibody.

(Chl) of FIG. 5 (B) is an autofluorescence image of a chloroplast, and the image (anti-HA) of FIG. 5 (C) is an immunofluorescence staining image with an anti-HA antibody. The localization of the ChlTP-sfGFP-HA-GP-Co1 protein to the chloroplast, which is detected by the anti-HA antibody, can be confirmed.

The sequences of the primers used in Example 1 and Example 2 are shown in Table 1.

TABLE 1

| Sequences of the primers used in Example 1 and Example 2 | | |
| --- | --- | --- |
| Primer | Sequence | SEQ ID NO |
| #1 d184 (+23) R | CGTCACCCTCGGGACTTGATGTTTACGTTC | 47 |
| #2 bT3 (+1) F | TAAACTAGCTATTTATCTGGTACATATCATTCATAAGCACATG | 48 |
| #3 HS (-200) Fd184 | gtcccgagggtgacgCTTATAGCTTACGTGGCGGATTCG | 49 |
| #4 HS (-1) R | GAATCCCTGGTTCTCTCACAGG | 50 |
| #5 J042 (1) Fhs | gagaaccagggattcATGGTGTTTACGTGTGCTGC | 51 |
| #6 J042 (1209) R-link3 | ggcgcctgcaccggatccGAAATGCTGCGCTATGTAGTTGG | 52 |
| #7 GP (1) F-linker3 | tccggtgcaggcgccATGGTTCCACAAGCACTGTT | 53 |
| #8 GP (1572) R-linker2 | tccaccgcctccaccAAGGCCTGTTTCGCCAC | 54 |
| #9 sfGFP (1) F-linker2 | ggtggaggcggtggaggcATGAGCAAGGGCGAGGA | 55 |
| #10 sfGFP (714) Rbt | taaatagctagtttaCTTGTACAGCTCGTCCATGC | 56 |
| #11 D184 (1200) F | CGCCTTCTCCTGGACGAGTACGCATTGG | 57 |
| #12 D184 (+1400) R | CCAGAGCCCTACCGGCACGCC | 58 |
| #13 APCC (-1) R | GGTCAACGAACGAAGAAACACAG | 59 |
| #14 bT3' (+1) | TAAACTAGCTATTTATCTGGTACATATCATTCATAAGCACATG | 60 |
| #15 SecA (1) Fapcc | cttcgttcgttgaccATGTTCCATGTGACGTACCC | 61 |
| #16 SecA (390) R-linker-ha | atcgtatgggtacatCCCGGTGAACAGCTCCTCGCCCTTGCTCATACCACCACCTCCGCCACCTCTGAGTTCATCGCTTTTGAGTTGTTC | 62 |
| #17 HA (1) F | ATGTACCCATACGATGTTCCTGACTATGCGGG | 63 |
| #18 HA (90) R | AGCGTAATCTGGAACGTCATAAGGGTATCCTG | 64 |
| #19 GP (1) Fha | gttccagattacgctATGGTTCCACAAGCACTGTTGC | 65 |
| #20 Col-GP (1680) Rbt | taaatagctagtttaTGGGAGCGGCGAGCGCGCCGGCAGCTGGTGGAAGCTAAGGCCTGTTTCGCCACC | 66 |

Analysis of Intracellular Localization of ChlTP-sfGFP-HA-GP-Co1 Protein

In order to analyze the intracellular localization of the ChlTP-sfGFP-HA-GP-Co1 protein, the Chl-TP-3HA-GP-Co1 expressing strain that had been cultured in the absence of MG-132 under light irradiation for 2 days at 40° C. was fixed and subjected to immunofluorescence staining using an anti-HA antibody.

The results of immunofluorescence staining are shown in FIG. 5. From the anti-HA antibody signal, it was shown that the ChlTP-sfGFP-HA-GP-Co1 protein is localized in the chloroplast (between the thylakoid in the central part and the envelope). The image (PC) of FIG. 5 (A) is a phase-contrast microscope image showing the outline of a cell, the image Example 3

Administration of GAPDH-GP-sfGFP Expressing Strain to Mouse

The GAPDH-GP-sfGFP expressing strain was suspended in a 300 mM glucose solution (an isotonic solution) so that the concentration thereof was $1.3 \times 10^8$ cells/mL (OD750=4), and 250 μL of the suspension was directly delivered to the stomach of a mouse (an ICR strain) using a sonde. Then, after 0, 0.5 and 1.0 hours, the stomach, the upper part of the small intestine, and the lower part of the small intestine were excised, and each of the excised organs was suspended in 1 mL of a 300 mM glucose solution. After centrifuging the suspension, the supernatant was separated and subjected to an ELISA assay for sfGFP, and the absorbance at 450 nm was measured.

Table 2 shows the measurement results of the relative concentration of sfGFP (the absorbance at 450 nm by ELISA assay) in each of the organs. sfGFP was hardly detected in the stomach and was detected in the small intestine immediately after the administration. This result indicates that the algal cells migrated from the stomach to the intestine immediately after the administration and did not rupture in the stomach but ruptured in the intestine.

TABLE 2

| Measurement results of the relative concentration of sfGFP in each of the organs | | | |
|---|---|---|---|
| Time after administration (hours) | Abs450 | | |
| | Stomach | Upper part of small intestine | Lower part of small intestine |
| 0 | −0.003 | 0.433 | 0.034 |
| 0.5 | −0.009 | 0.041 | 0.013 |
| 1 | 0.003 | 0.019 | −0.011 |

Example 4

Feeding of Mice with Alginate Solidified Feed Containing sfGFP Expressing Strain The cells (the sfGFP expressing strain) of *C. merolae* 10D (Sumiya et al. 2014, PLoS One. 9 (10): e111261; PMID: 25337786), in which sfGFP was expressed in the cytoplasm and labeled, were mixed with a commercially available feed (CLEA Rodent Diet CE-2, CLEA Japan, Inc.) and solidified with the alginate to prepare a feed sample as follows.

27 mL of a 300 mM glucose solution (an isotonic solution) in which the sfGFP expressing strain was suspended (OD750=4) was centrifuged at 3,000 g for 10 minutes, and the precipitated cells were collected. The cells of the sfGFP expressing strain and 1.12 g of the commercially available feed (CE-2) were suspended in 10 mL of a 2.5% sucrose solution containing 1% sodium alginate. Then, the suspension was added dropwise to a 10% calcium chloride solution to obtain a feed sample of an alginate solidified body containing the sfGFP expressing strain and the commercially available feed. The content of the sfGFP expressing strain in the feed sample is 4.6 mg wet weight/g (80 to 110 mg per grain).

Mice (an ICR strain) were allowed to feed on the above feed sample for 4 hours and then were reared ordinarily. 4, 8, 24, and 48 hours after the start of feeding, the bowel, the upper part of the small intestine, and the lower part of the small intestine of the mice were excised. Each of the excised organs was suspended in a 300 mM glucose solution and centrifuged at 1,000 g, and then the supernatant was collected and used as a sample for measuring the extracellular concentration of sfGFP. After the supernatant was collected, the precipitate was resuspended by adding distilled water (DW) having an amount equal to the amount of the collected supernatant and centrifuged at 1,000 g, and then the supernatant was collected and used as a sample for measuring the intracellular concentration of sfGFP. The amounts of sfGFP in the extracellular concentration measurement sample and the intracellular concentration measurement sample were quantified by a commercially available ELISA kit (GFP ELISA kit; cat no. ab171581, Abcam plc), and individually used as the extracellular concentration and the intracellular concentration.

Table 3 shows the measurement results of the relative concentration of sfGFP (the absorbance at 450 nm by ELISA assay) in each of the organs. Regarding both extracellular and intracellular concentrations, sfGFP was detected at a high concentration in the small intestine as compared with the stomach. In addition, the sfGFP concentration was high in the lower part of the small intestine as compared with the upper part of the small intestine, and the ratio of the intracellular concentration to the extracellular concentration was also increased. This result indicates that the algal cells ruptured in the small intestine and sfGFP was incorporated into the small intestine cells.

TABLE 3

| Measurement results of the relative concentration of sfGFP in each of the organs | | | | | | |
|---|---|---|---|---|---|---|
| Time after start of feeding (hours) | Stomach | | Upper part of small intestine | | Lower part of small intestine | |
| | Extracellular | Intracellular | Extracellular | Intracellular | Extracellular | Intracellular |
| | | | Abs450 | | | |
| 4 | 0.022 | 0.013 | 0.050 | 0.013 | 0.116 | 0.060 |
| 8 | −0.005 | −0.002 | 0.086 | 0.033 | 0.118 | 0.057 |
| 24 | 0.003 | 0.005 | 0.101 | 0.027 | 0.103 | 0.057 |
| 48 | 0.010 | 0.005 | 0.051 | 0.044 | 0.106 | 0.083 |

Example 5

Administration Experiment and Serum Collection

For the "control suspension administration group", the GAPDH-GP-sfGFP expressing strain was suspended in a 300 mM glucose solution (an isotonic solution) so that the concentration thereof was $1.3 \times 10^8$ cells/mL (OD750=4), and 300 µL of the suspension was directly delivered to the stomach of a mouse (an ICR strain; three mice) using a sonde. The same amount was orally administered 6 times every other week, and serum was taken 2 weeks after the final administration.

For the "suspension administration group", the Chl-TP-3HA-GP-Co1 expressing strain (the ChlTP-sfGFP-HA-GP-Co1 protein expressing strain of *C. merolae*) was suspended in a 300 mM glucose solution so that the concentration thereof was $1.3 \times 10^8$ cells/mL (OD750=4), and 300 µL of the suspension was directly delivered to the stomach of a mouse (an ICR strain; four mice) using a sonde. The same amount was orally administered 6 times every other week, and serum was taken 2 weeks after the final administration.

For the "alginate solidified feed administration group", 27 mL of a 300 mM glucose solution in which the Chl-TP-3HA-GP-Co1 expressing strain (the ChlTP-sfGFP-HA-GP-Co1 protein expressing strain of *C. merolae*) was suspended (OD750=4) was centrifuged at 3,000 g for 10 minutes, and the precipitated cells were collected. The cells of the Chl-TP-3HA-GP-Co1 expressing strain and 1.12 g of the commercially available feed (CE-2) were suspended in 10 mL of a 2.5% sucrose solution containing 1% sodium alginate. Then, this suspension was added dropwise to a 10% calcium chloride solution to obtain a feed sample of an alginate solidified body containing the Chl-TP-3HA-GP-Co1 expressing strain and the commercially available feed. The content of the Chl-TP-3HA-GP-Co1 strain is 4.6 mg wet weight/g (80 to 110 mg per grain). Mice (an ICR strain; four mice) were allowed to feed on the feed sample and then were reared ordinarily. The feeding of the feed sample was carried out 6 times every other week, and serum was taken 2 weeks after the final feeding.

Evaluation of Anti-GP Protein Antibody Production

The production of an anti-GP protein antibody was checked by immunoblotting. First, in order to fuse a 6×histidine tag sequence to the amino terminal of the GP protein of rabies virus, the ORF of the GP gene was cloned into a pQE80 vector (including the 6×histidine tag sequence, product code: 32923, QIAGEN) to construct a plasmid. This plasmid was introduced into *Escherichia coli* to express a 6×histidine tag-fused GP protein (protein size: about 50 kDa). This was concentrated using a nickel column (product code: 17531901, GE Healthcare). Next, the 6×histidine tag-fused GP protein concentrate was separated by electrophoresis by the SDS-PAGE method. Proteins were transferred from the gel after electrophoresis to a polyvinylidene fluoride (PVDF) membrane (product code: IPVH00010, Merck KGaA). This was immersed in a diluted solution of the serum collected from each of the mice and incubated at room temperature for 1 hour. The diluted solution of the serum was adjusted by diluting serum to ⅟₅₀₀ in a Tris buffer (pH 7.5, containing 0.1% Tween 20). The presence or absence of the anti-GP protein antibody contained in the serum was determined according to the presence or absence of an antibody reaction to the GP protein positioned near 50 kDa.

Result

Figure 6:
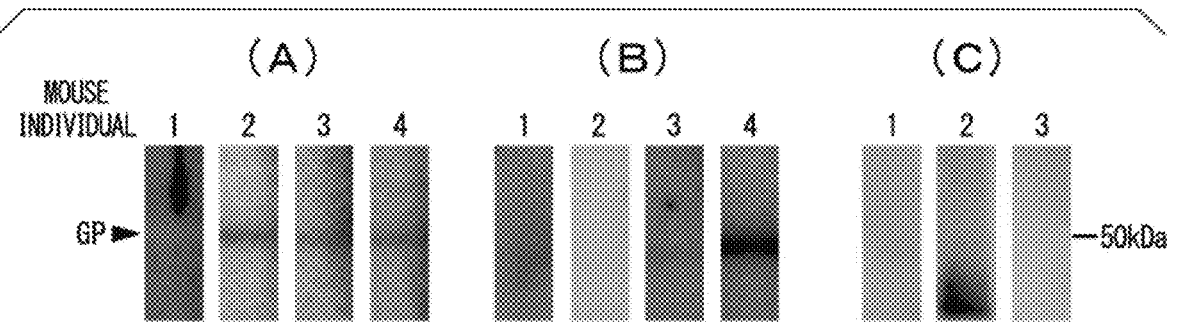
FIG. 6 is figures showing results of evaluating, by immunoblotting, the production of an anti-GP protein antibody in mice to which a suspension of an sfGFP expressing strain (a control suspension administration group), a suspension of a Chl-TP-3HA-GP-Co1 expressing strain (a suspension administration group), or an alginate solidified feed of the Chl-TP-3HA-GP-Co1 expressing strain (an alginate solidified feed administration group) is administered. (A): alginate solidified feed administration group; (B) suspension administration group; (C) control suspension administration group. Numbers 1 to 4 indicate individual numbers of mice.

The results of the immunoblotting are shown in FIG. 6. No band was detected at the position of about 50 kDa, which is the molecular weight size of the rabies GP protein, in the diluted solution of the serum of each of the mouse individuals 1, 2, and 3 in the "control administration group (liquid)" which was the negative control (FIG. 6 (C)). On the other hand, in the mouse individuals 2, 3, and 4 (FIG. 6 (A)) of the "alginate solidified feed administration group" and the mouse individuals 3 and 4 (FIG. 6 (B)) of the "suspension administration group", a band was detected at the position of about 50 kDa. From these results, mice fed with the suspension of *C. merolae*, in which the rabies GP protein had been expressed, or the alginate solidified feed were shown to produce the anti-GP protein antibody.

Discussion

In the mouse individual 2 of the "control suspension administration group", a band having a size smaller than the predicted size of the 6×histidine tag-fused GP protein was detected, which is presumed to be because an antibody possessed by the individual mouse reacted non-specifically with a protein contained in the 6×histidine tag-fused GP protein concentrate, where the protein is derived from *Escherichia coli* regardless of the administration of the GP protein.

From the series of examples, it has been confirmed that an antigenic protein that is appropriately introduced using the acid-resistant cell that is used in the present invention can be delivered to a site posterior to the upper part of the small intestine. Further, it has been confirmed that even in a case where the acid-resistant cells of the present invention, into which the antigenic protein has been introduced, are mixed in the feed in a form that can be used in the ordinary livestock industry and aquaculture industry, the antigenic protein can be similarly delivered to the target site. Further, it has been confirmed that the antigenic protein delivered in such a manner as described above also drives the intestinal immune system, whereby an antibody is produced in the blood as well.

What is claimed is:

1. A drug delivery composition comprising an acid-resistant cell that encloses a drug,
   wherein the acid-resistant cell is a cell in which cell rupture is caused at pH 7, and the acid-resistant cell is a haploid cell of algae that belong to the class Cyanidiophyceae.

2. The drug delivery composition according to claim 1, wherein the drug is localized in a sac-shaped membrane structure included in the acid-resistant cell.

3. The drug delivery composition according to claim 2, wherein the sac-shaped membrane structure is at least one selected from the group consisting of an exogenous liposome, a cell membrane, and an organelle.

4. The drug delivery composition according to claim 3, wherein the organelle is at least one selected from the group consisting of a mitochondrion, a chloroplast, an endoplasmic reticulum, a vacuole, a cell nucleus, a peroxisome, and a Golgi apparatus.

5. The drug delivery composition according to claim 1, wherein the drug is at least one selected from the group consisting of a low molecular weight compound, a peptide, a protein, and a nucleic acid.

6. The drug delivery composition according to claim 1, wherein the drug is a drug that acts in an intestine.

7. The drug delivery composition according to claim 1, wherein the drug is a drug that has immunogenicity.

8. The drug delivery composition according to claim 1, wherein the acid-resistant cell is a cell that is resistant to acidic conditions of pH 1 to 3.

9. A feed comprising the drug delivery composition according to claim 1.

10. A pharmaceutical product comprising the drug delivery composition according to claim 1.

11. A food comprising the drug delivery composition according to claim 1.

12. An acid-resistant cell that encloses a drug in the cell, wherein the acid-resistant cell is a cell in which cell rupture is caused at pH 7, and the acid-resistant cell is a haploid cell of algae that belong to the class Cyanidiophyceae.

13. An acid-resistant cell that encloses a drug in the cell, wherein the drug is localized in a sac-shaped membrane structure included in the acid-resistant cell, and the acid-resistant cell is a cell in which cell rupture is caused at pH 7, and the acid-resistant cell is a haploid cell of algae that belong to the class Cyanidiophyceae.

14. A method of producing the acid-resistant cell of claim 13, the method comprising:
   introducing a gene encoding a fusion protein that contains a peptide or protein as the drug and contains a peptide or protein localizable to a cell membrane or an organelle, into the acid-resistant cell.

15. A drug carrier comprising an acid-resistant cell, wherein the acid-resistant cell is a cell in which cell rupture is caused at pH 7, and the acid-resistant cell is a haploid cell of algae that belong to the class Cyanidiophyceae.

16. The drug carrier according to claim 15, wherein the acid-resistant cell is a cell that is resistant to acidic conditions of pH 1 to 3.

17. An acid-resistant cell comprising an exogenous substance, wherein the acid-resistant cell is a cell in which cell rupture is caused at pH 7, and the acid-resistant cell is a haploid cell of algae that belong to the class Cyanidiophyceae.

18. The acid-resistant cell according to claim 17, wherein the exogenous substance is localized in a sac-shaped membrane structure included in the acid-resistant cell.

* * * * *